US009545520B2

(12) United States Patent
Matos

(10) Patent No.: US 9,545,520 B2
(45) Date of Patent: Jan. 17, 2017

(54) METHOD AND APPARATUS FOR CONTROLLING AN IMPLANTABLE MEDICAL DEVICE

(76) Inventor: Jeffrey A. Matos, New Rochelle, NY (US)

(*) Notice: Subject to any disclaimer, the term of this patent is extended or adjusted under 35 U.S.C. 154(b) by 1929 days.

(21) Appl. No.: 12/657,155

(22) Filed: Jan. 14, 2010

(65) Prior Publication Data
US 2011/0172740 A1 Jul. 14, 2011

(51) Int. Cl.
A61N 1/08 (2006.01)
A61N 1/372 (2006.01)
H04L 1/00 (2006.01)

(52) U.S. Cl.
CPC ......... A61N 1/37264 (2013.01); H04L 1/0003 (2013.01); H04L 1/0013 (2013.01); H04L 1/0015 (2013.01); H04L 1/0026 (2013.01); A61N 1/08 (2013.01)

(58) Field of Classification Search
None
See application file for complete search history.

(56) References Cited

U.S. PATENT DOCUMENTS

2001/0039375 A1* 11/2001 Lee et al. ............... 600/301
2004/0077995 A1* 4/2004 Ferek-Petric et al. ..... 604/66
2008/0300659 A1* 12/2008 Matos ..................... 607/60

* cited by examiner

Primary Examiner — Carl H Layno
Assistant Examiner — Jon Eric C Morales
(74) Attorney, Agent, or Firm — Karl F. Milde, Jr.; Eckert Seamans Cherin & Mellott, LLC

(57) ABSTRACT

A system and methods of maintaining communication with a medical device for exchange of information, instructions, and programs, in a highly reliable manner. Apparatus and methods for accomplishing this task include:

1) The inclusion of a locating device in the system, in close proximity to an implanted device, but which does not drain the implanted device battery. The locating device may be implanted or external to the body.
2) The use of motion detection and global positioning system devices to locate elements within a communicating system for the medical device;
3) The assessment of received signal quality by elements of the system;
4) The use of a notification system for a device user who is moving out of range of communications; and
5) Documenting the absolute and functional integrity of instructions received by the medical device.

56 Claims, 72 Drawing Sheets

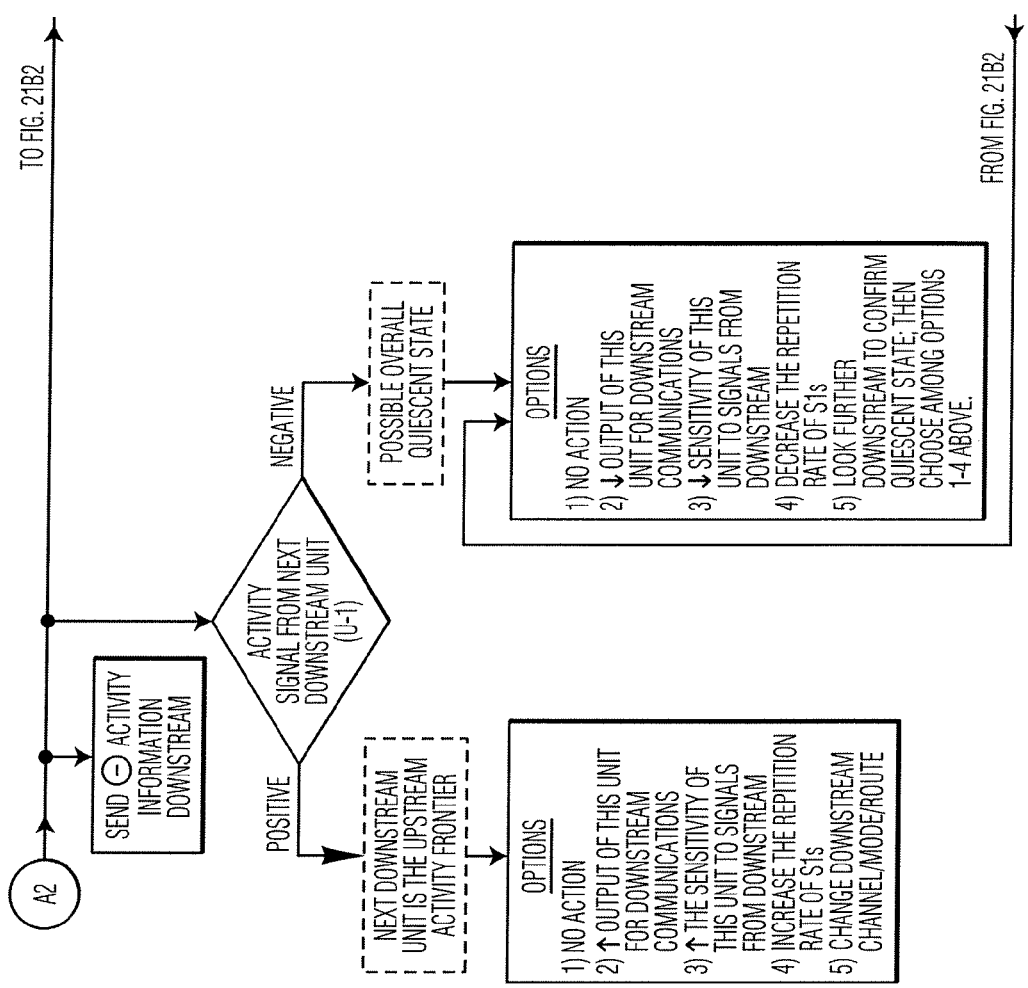
FIG. 21B1

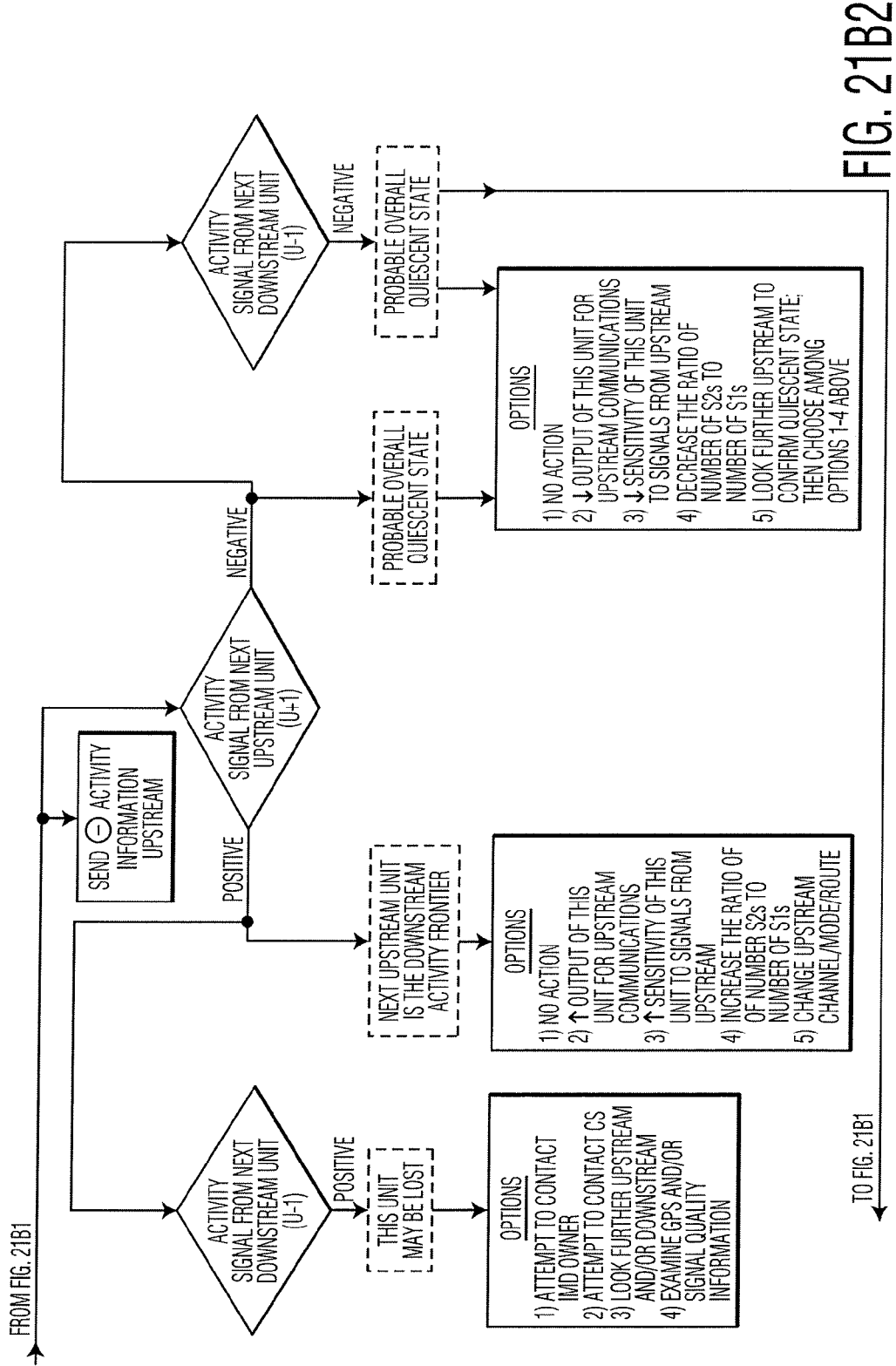
FIG. 21B2

| | |
|---|---|
| FIG. 22A | FIG. 22B |

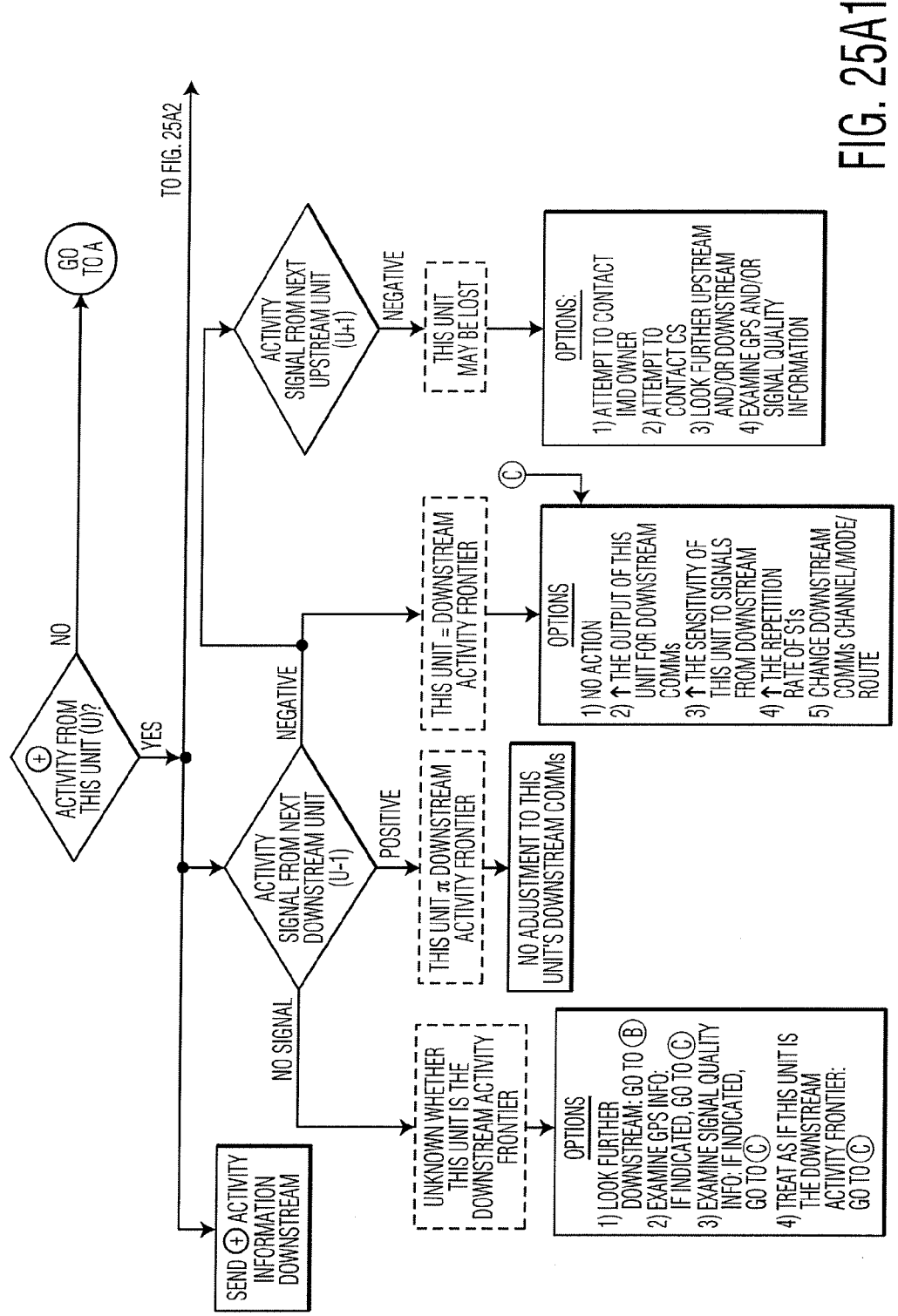
FIG. 25A1

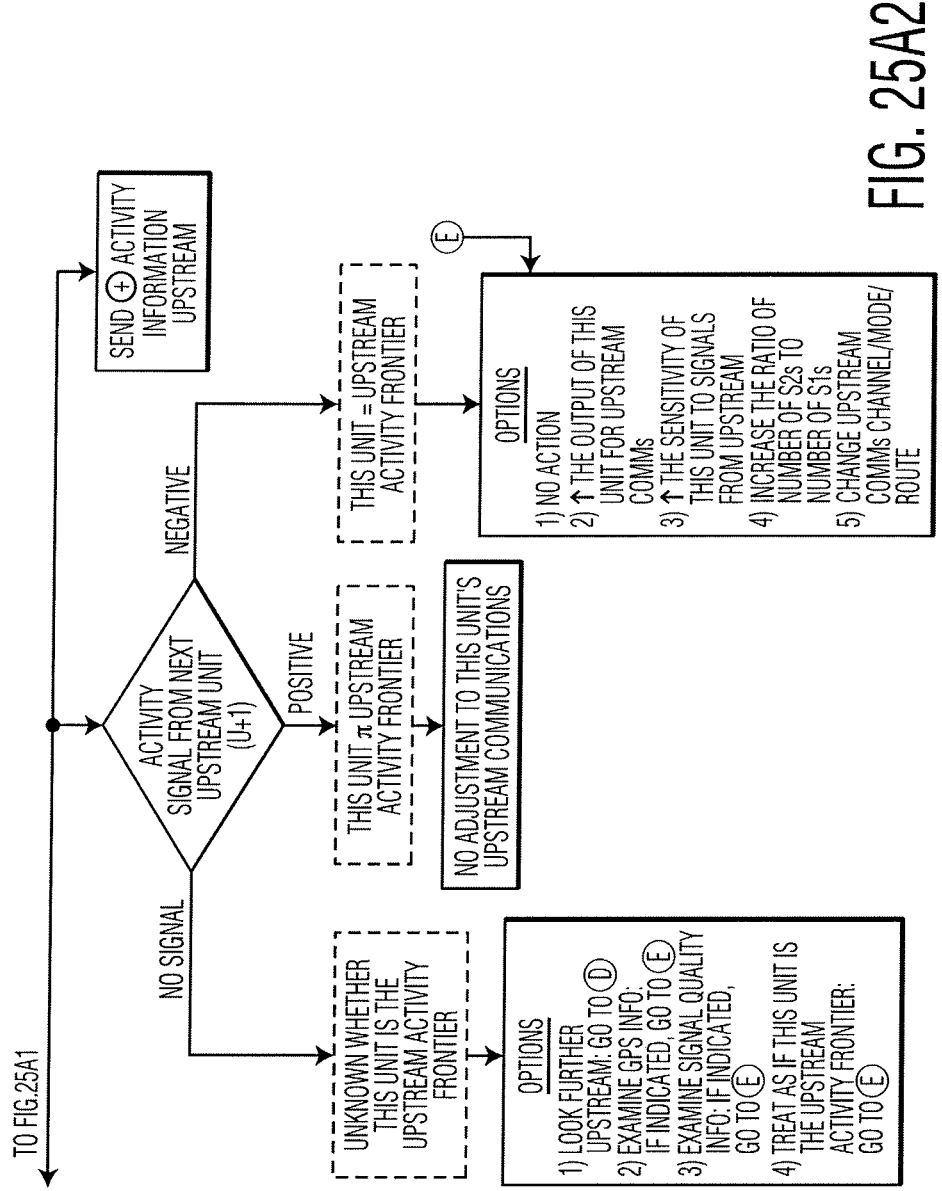
FIG. 25A2

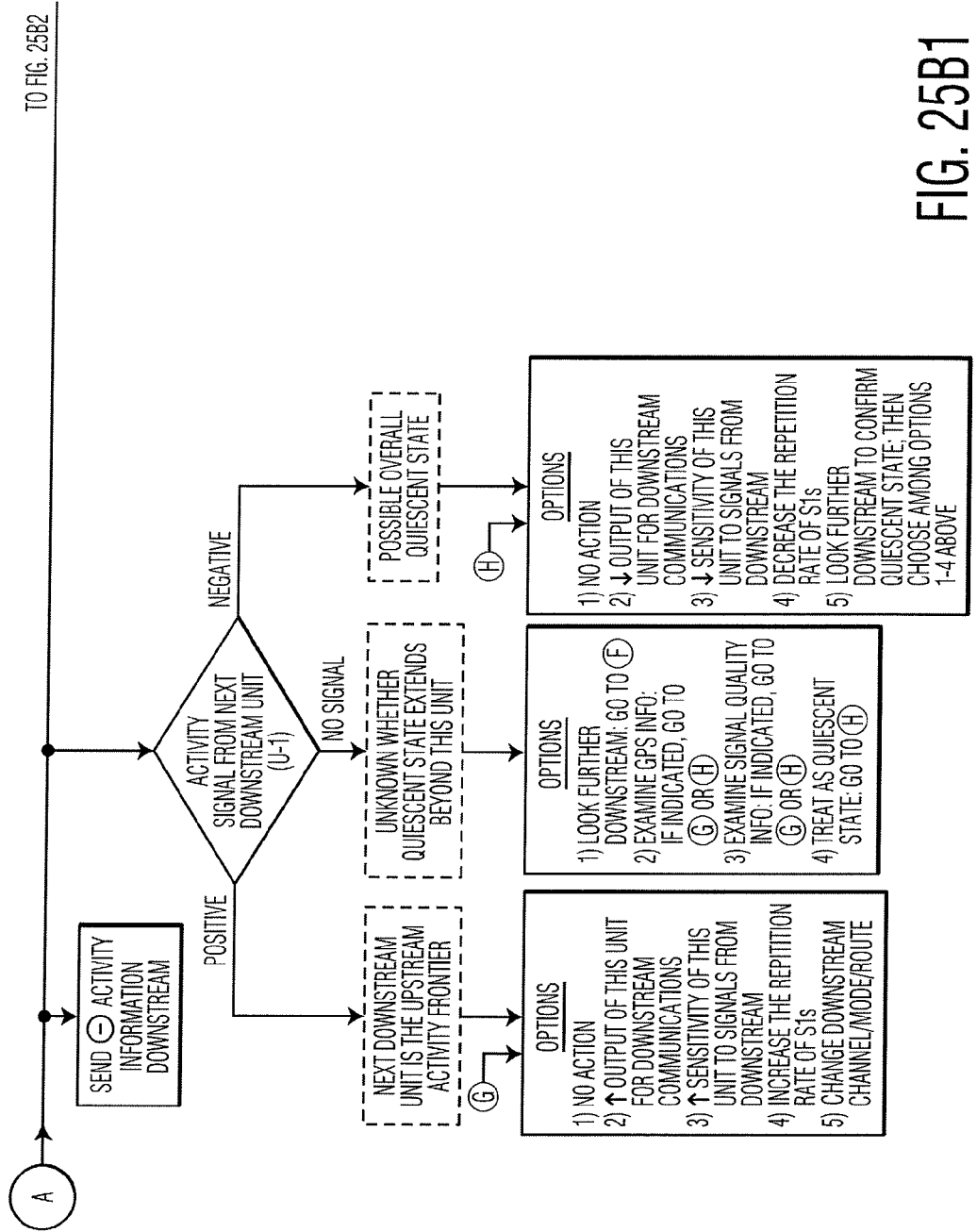
FIG. 25B1

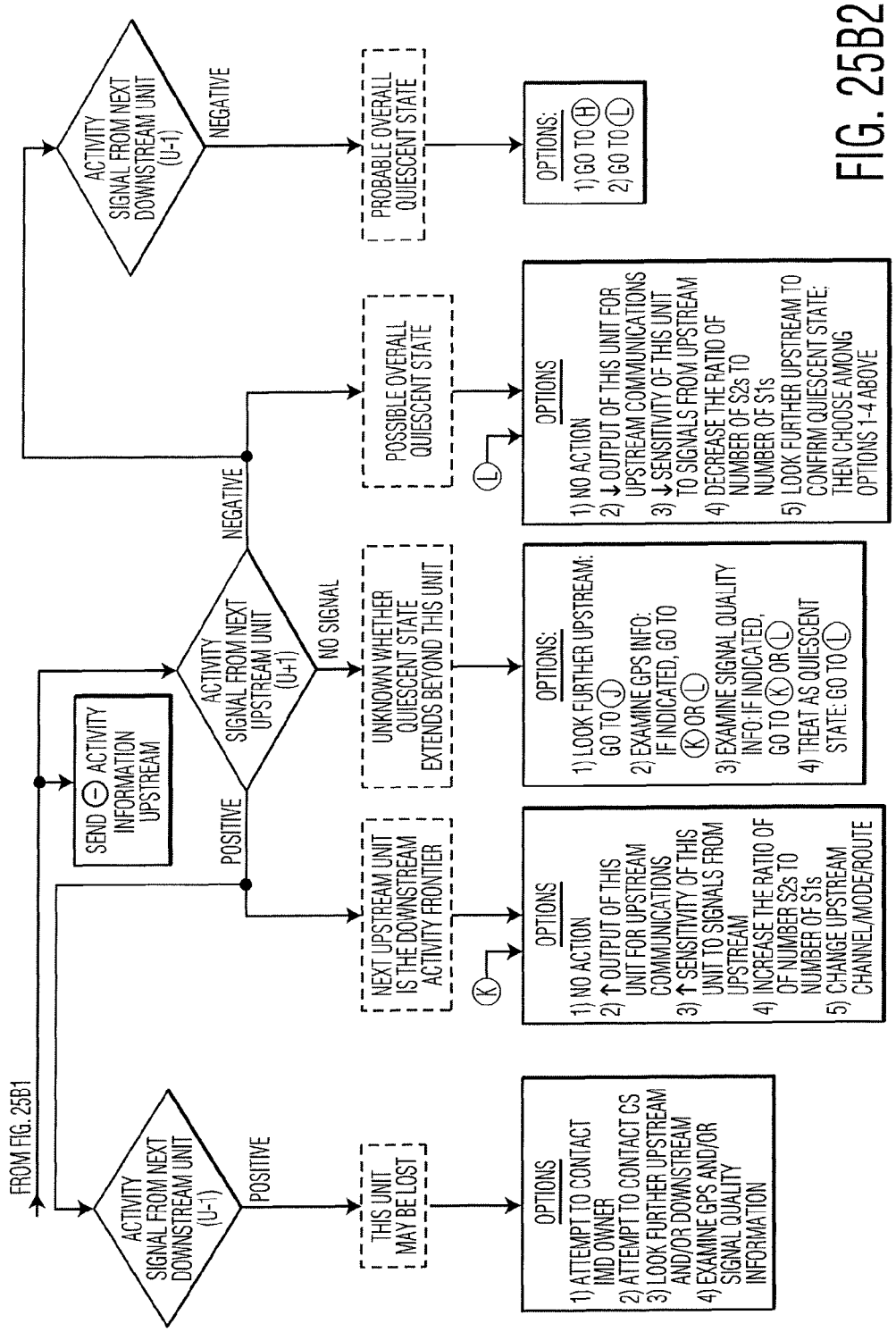
FIG. 25B2

|   | U | U+1A | U+1B | U+2A | U+2B | U+3 |
|---|---|------|------|------|------|-----|
| U+3    |      | K*   | N*   | Q*   | R*   |      |
| U+2B   | F*   | J*   | M*   | P*   |      | R    |
| U+2A   | E*   | H*   | L*   |      | P    | Q    |
| U+1B   | D*   | G*   |      | L    | M    | N    |
| U+1A   | C*   |      | G    | H    | J    | K    |
| U      |      | C    | D    | E    | F    |      |

FIG. 29B

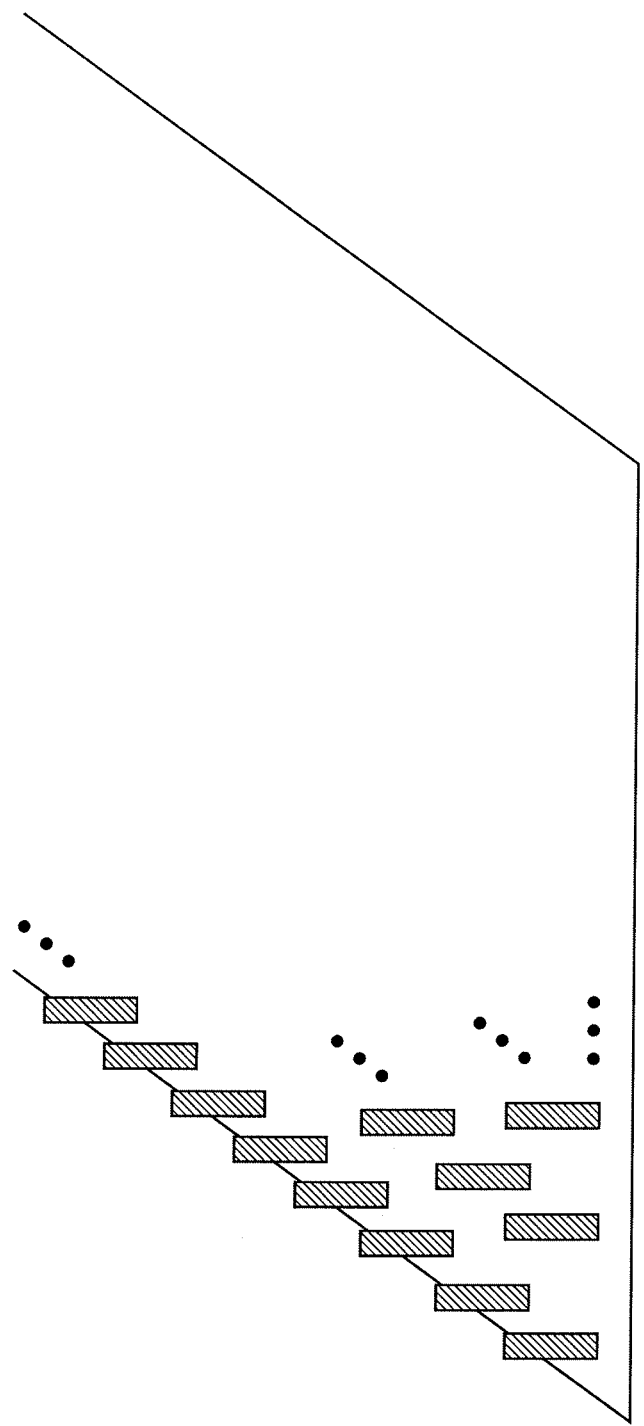

METHOD AND APPARATUS FOR CONTROLLING AN IMPLANTABLE MEDICAL DEVICE

CROSS-REFERENCE TO RELATED APPLICATIONS

The subject matter of this application is related to that of:
1) U.S. patent application Ser. No. 10/460,458, published on Dec. 18, 2003 as U.S. Patent Publication No. US/2003/0233129, now U.S. Pat. No. 7,277,752;
2) U.S. patent application Ser. No. 11/502,484, published on Feb. 2, 2007 as U.S. Patent Publication No. US/2007/0043585A1, now allowed;
3) U.S. patent application Ser. No. 11/893,897, published on Dec. 27, 2007 as U.S. Patent Publication No. US/2007/0299473, now U.S. Pat. No. 7,769,465;
4) U.S. patent application Ser. No. 11/895,934, published on Mar. 6, 2008 as U.S. Patent Publication No. US/2008/0058884, now U.S. Pat. No. 8,214,043;
5) U.S. patent application Ser. No. 12/154,079, published on Dec. 4, 2008 as U.S. Patent Publication No. US/2008/0300659, now U.S. Pat. No. 8,473,065;
6) U.S. patent application Ser. No. 12/455,940, published on Nov. 5, 2009 as U.S. Patent Publication No. US/2009/0276013, now U.S. Pat. No. 7,840,277; and
7) Provisional Application No. 61/204,957, filed Jan. 13, 2009, priority of which is hereby claimed.

The aforementioned U.S. Patent and published Patent Applications are incorporated herein by reference.

BACKGROUND OF THE INVENTION

Implantable medical devices ("IMDs") exhibit growth in terms of:
a) the development of new devices which perform functions not previously performed;
b) the development of more sophisticated devices that replace previous simpler models; and
c) the number of implanted units per unit time.

Some devices perform "mission critical" functions—i.e. they stimulate heart, or brain, or deliver powerful drugs.

The devices are designed to function largely autonomously. That is, they interact with the patient in whom they are implanted ("the IMD owner"), and interact with an MD only on the infrequent occasions when the MD is present.

From time to time, the actions of these devices may result in unintended and/or harmful consequences due to:
a) improper or suboptimal programming of the device by a physician or technician;
b) a change in the condition of a patient, such that what was appropriate programming in the past, is no longer appropriate given the patients altered medical condition;
c) malfunction of the device itself;
d) malfunction of a sensor which provides information to the device; and
e) electromagnetic interference.

Under these circumstances, it is desirable to have a means of very rapidly addressing a malfunction or pseudo-malfunction [e.g. suboptimal programming], e.g. by reprogramming the device so that in the short term, one or more undesirable actions are prevented. Though the patient may go to a physician's office or seek help in an Emergency Room, these actions may require hours to days to execute. On the other hand, the ability to remotely communicate with an implantable device, and to control its function remotely, can provide a solution that is available in minutes or seconds, and can provide real-time corrections as well.

The present application addresses various aspects of the communications between an IMD and a remotely located medical professional. Whereas the preferred embodiment of the invention is an IMD, the inventive concepts described herein may be applied to other devices—medical and non-medical—as well.

ABBREVIATIONS AND DEFINITIONS

Adjacent—two communication units which may communicate directly

Alpha Unit—a communications unit which is upstream from a beta unit

Beta Unit—a communications unit which is downstream from an alpha unit

CCSI—composite communication status information

CPD—cell phone device

CS—central station

Downstream—refers to a communications unit which is linked to the IMD by fewer hops than a corresponding upstream unit. The upstream unit relays a signal originating in the CS to the downstream unit.

EID—external RFID device

GPS—global positioning system

ICD—implantable cardioverter-defibrillator

IID—implantable RFID device

IMD—implantable medical device

IMD owner—the person in whom an IMD is implanted

MD/A/P—motion detecting accelerometer/piezoelectric crystal

MDC—motion detecting capability

PM—Pacemaker

Quiescent—a state in which mobile communicating units are not moving

RFID—radiofrequency identification device

SU—stationary unit

"Transmitting" may mean (a) as an RF signal, (b) over the telephone system, (c) via modem to the internet or (d) over a private carrier Upstream—refers to a communications unit which is linked to the central station by fewer hops than a corresponding downstream unit. The upstream unit relays a signal originating in the CS to the downstream unit.

WD—wrist device

SUMMARY OF THE INVENTION

Among the complexities of remotely controlling an IMD are the need for extremely reliable communications with the IMD, the need to not excessively drain the battery of the IMD, and the need for communications security. To accomplish these goals, one must create an environment in which the IMD owner is, at all times (or as close to 'all times' as possible) near one or more communications repeater units. Ideally, at least one of the units would be either (a) very near the IMD owner, (b) carried by the IMD owner (e.g. a cell phone device, as discussed hereinbelow), (c) touching the IMD owner's body (e.g. a wrist device, as discussed hereinbelow), (d) worn by the IMD owner or even implanted in the IMD owner. Redundancy among these communication units increases the reliability of the system. By designating one or more of the units as a locator unit, i.e. a unit which is very likely to be in the same location as the IMD owner at virtually all times, the communication system may be optimized on a frequent basis without draining the IMD battery; i.e. optimization then involves elements of the system communicating with the locator unit, rather than with the IMD. By creating a system in which one repeater unit is very near the IMD owner, then at such times that communication with the IMD is necessary, IMD power output can be low, and thus IMD battery drain can be similarly low.

In the event that the system finds itself incapable of establishing a robust communications link between the IMD owner and a central station, then a means of notifying one or more individuals who can rectify the situation is desirable. The notified individual could be the IMD owner, a person living or working with or near the IMD owner, or a system administrator who handles the task of seeking out the IMD owner. Notification may be via one or more of the devices in the IMD owner's environment which also serve as a repeater unit, e.g. the WD or the CPD. Among the short term remedies for the IMD owner are (a) movement to a more optimal location, (b) recharge or replace the battery of a repeater unit whose battery has depleted, or (c) no action. The longer term options may entail an alteration in the environment, e.g. placing a more powerful stationary unit in a location frequented by the IMD owner which repeatedly poses a communications challenge (e.g. his basement).

IMD communication networks are possible which are:
(a) self organizing—i.e. each repeater unit optimizes communications with two or more neighbors;
(b) globally organized—i.e. a single unit optimizes the entire system of communicating units; or
(c) locally organized—i.e. two or more units each optimize communications among a local group (e.g. the CPD optimizes communications in the environment of the IMD and another upstream organizing unit optimizes communications at a point between the CPD and the CS.

Devices that have been referred to as "cell phones" now are increasingly sophisticated, with substantial and increasing bandwidth access, memory, computational and advanced communication features. Such devices, suitably modified from a commercial off-the-shelf version, or a version which is initially designed for an IMD owner, could function as a repeater unit, a notification unit and a local or global communication system manager. Although such a unit could also be designated as the unit closest to the IMD-owner, a wearable or implantable device might do better.

Besides communications management, sophisticated information management techniques are required for a remote management of an IMD. The invention described herein addresses the need for verification that instruction(s)/program(s) sent to the IMD are properly received/installed, and that the IMD functions properly after receipt of the instruction(s)/program(s). Robust encryption/decryption techniques to prevent unauthorized access to the IMD, are also described herein. In conjunction with outside access to the IMD, optional IMD owner consent methods are also described.

FEATURES OF THE INVENTION

1) A multi-repeater communications system/network which allows for (a) maximization of signal quality on a dynamic basis, (b) maximization of user freedom and (c) minimization of IMD battery drain.
2) Implantable communications repeater units are a possibility.
3) Wearable Repeater Units (e.g. WD) are a possibility.
4) RFIDs as locating device and/or repeater device are a possibility, including (but not limited to) the battery-less type of RFID; including but not limited to implantable RFIDs and RFIDs embedded in clothing and personal items (wallet, "pocket book," "handbag" etc.).
5) Cell phone as communications repeater unit is a possibility.
6) Repeater Units with loss/misplacement detection, based on patterns of motion, GSR analysis and temperature analysis.
7) IMD owner notification in the event of an actual or a potential communications fault. One or more of the repeater units may also include a notification function, (or notification may be via a stand-alone notification device).
8) Interactive IMD owner notification system.
9) Use of motion detection apparatus in PMs and ICDs for communications management.
10) Use of MD/A/P in repeater units for communications management.
11) Multimodal motion detection including (a) signal quality, (b) GPS and (c) MD/A/P and use of the position/motion/acceleration information, signal quality information and handshake information to optimize communications.
12) Handshake format which manages communications, for use with the system.
13) Architectures are possible with repeater units (a) in series, (b) in parallel, (c) in a network with both series and parallel elements.
14) Dynamic communication system architecture: As needed, a communications unit can be bypassed, a communications route can be altered, a channel can be switched, a communications mode can be altered. Both series and parallel communication elements may be incorporated into the communications network.
15) Communication systems are possible with:
a) local communications management: i.e. each communications unit co-manages itself and its neighbors;
b) global communications management: i.e. one communications unit manages all others; and
c) regional communications management: i.e. two or more communications units each manage a group of local communicating units.
16) Use of battery capacity for communications management decisions.
17) System for verification of proper transmission of an instruction/program from CS to IMD
18) Systems for verification of proper functioning of an IMD with a new instruction/program.
19) Static systems for highly secure encryption/decryption key generation and maintenance for the management of IMDs which are remotely accessible.
20) Dynamic systems for highly secure encryption/decryption key generation and maintenance for the management of IMDs which are remotely accessible.
21) IMD owner notification in the event an instruction/program needs to be installed, and an IMD owner permission granting algorithm.

BRIEF DESCRIPTION OF THE DRAWINGS

FIG. 29B is a matrix of 28 values which indicate communication conditions between certain pairs of the communication elements shown in FIG. 29A.

FIG. 36 is a representational diagram showing an array of portable memory units, each of which contains an encryption/decryption key for one IMD.

DETAILED DESCRIPTION OF THE PREFERRED EMBODIMENTS

Figure 1:
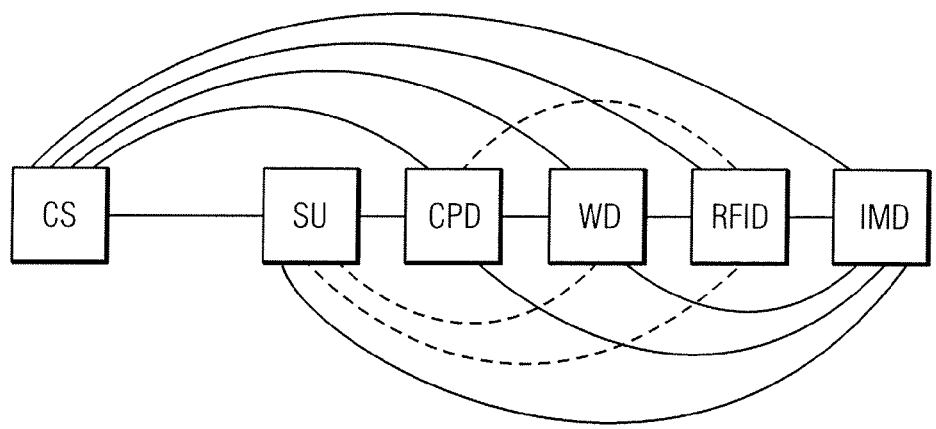
FIG. 1 is a block diagram of a system of repeater units linking a central station to an implantable medical device.

FIG. 1 shows a block diagram which shows the possible routes of communication between a central station (CS) and an implanted medical device (IMD). Four relay units are shown between the CS and the IMD including a stationary unit (SU), cell phone device (CPD), a wrist device (WD) and a radiofrequency identification device (RFID). The solid and broken lines between the units indicate the path of a signal which links the CS and the IMD.

The four relay units are shown by way of example, and numerous other examples are possible including those with a) more relay units, b) fewer relay units, c) with more of one kind of unit, d) fewer or none of another kind, and e) in which the sequence of relay units differs. Stationary units are in a fixed location and may have a hard-wired connection to a public telephone system or a connection (hard-wired or not) to an internet-based telephone system.

Cell phone devices are not hard wired and may be a commercial off-the-shelf unit with capability to simultaneously communicate with two other units. Alternatively, it may be a modified cellular phone unit, optimized for function in the capacity discussed hereinabove and hereinbelow. The cell phone's special value is that the likelihood that it is near to a person at any one time is greater than would be the case for a stationary unit (e.g. a SU located in the patient's home).

The wrist device (which may be located on other patient body parts other than the wrist—e.g. ankle, chest, etc.), also is of value because of the high likelihood of patient proximity. Because it may be even closer to the patient than a cell phone, the energy expenditure for communicating with it from a downstream device (i.e. a device which is the IMD, or and RFID) may be even less than that required for communication between the downstream device and the cell phone.

A variety of RFIDs are possible including a) external RFIDs, and b) internal RFIDs. The RFID may be a passive unit, a semi-passive one, an active one or a beacon type. These are intended to be in very close proximity to the IMD, and therefore to result in very minimal drain on the IMD battery if communication is required between the IMD and the RFID. Furthermore, RFIDs allow the system to locate an IMD by assessing the location of the IMD-companion (i.e. the RFID, or a wrist device). This approach also avoids draining the IMD battery during locating efforts.

The communication route from CS to IMD need not be the same as that from IMD to CS. Furthermore, the route of either or both legs may vary during the course of one communication session.

Any particular device may provide a locator function, a relay function or both. For example, in one embodiment of the invention, an RFID may perform a locator function in conjunction with an SU, while the same SU communicates with the IMD via the CPD.

The table below shows examples of systems with 1, 2 and 3 repeater units. In the example in the table, the RFID may function as a repeater unit.

Examples of IMD-CS Communication System Elements with One to Three Repeaters

| Patient Unit | First Repeater | Second Repeater | Third Repeater | Control Unit |
| --- | --- | --- | --- | --- |
| IMD | RFID | | | CS |
| IMD | WD | | | CS |
| IMD | CPD | | | CS |
| IMD | SU#1 | | | CS |
| IMD | SU#2 | | | CS |
| IMD | RFID | WD | | CS |
| IMD | RFID | CPD | | CS |
| IMD | RFID | SU#1 | | CS |
| IMD | RFID | SU#2 | | CS |
| IMD | WD | CPD | | CS |
| IMD | WD | SU#1 | | CS |
| IMD | WD | SU#2 | | CS |
| IMD | CPD | SU#1 | | CS |
| IMD | CPD | SU#2 | | CS |
| IMD | RFID | WD | CPD | CS |
| IMD | RFID | WD | SU#1 | CS |
| IMD | RFID | WD | SU#2 | CS |
| IMD | RFID | CPD | SU#1 | CS |
| IMD | RFID | CPD | SU#2 | CS |
| IMD | WD | CPD | SU#1 | CS |
| IMD | WD | CPD | SU#2 | CS |

Figure 2:
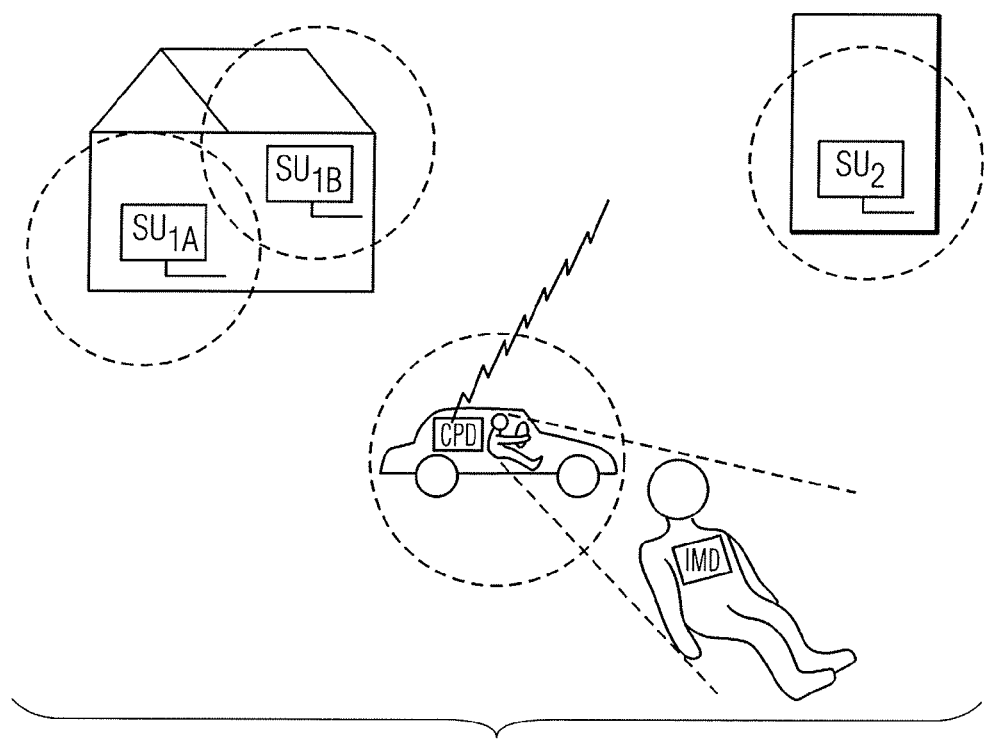
FIG. 2 is a representational diagram showing stationary and mobile repeater units in the environment of the IMD patient.

FIG. 2 shows a patient with an IMD, his home which contains SU-1A and SU-1B, and his office with another stationary unit, SU-2. The patient (with IMD seen in detailed view) is in a car and his CPD is in the car with him. The figure is intended to illustrate the concept that by populating the patient's environment with enough stationary and mobile communication devices, the patient's IMD may be within very close range of a communications device at all times.

Figure 3:
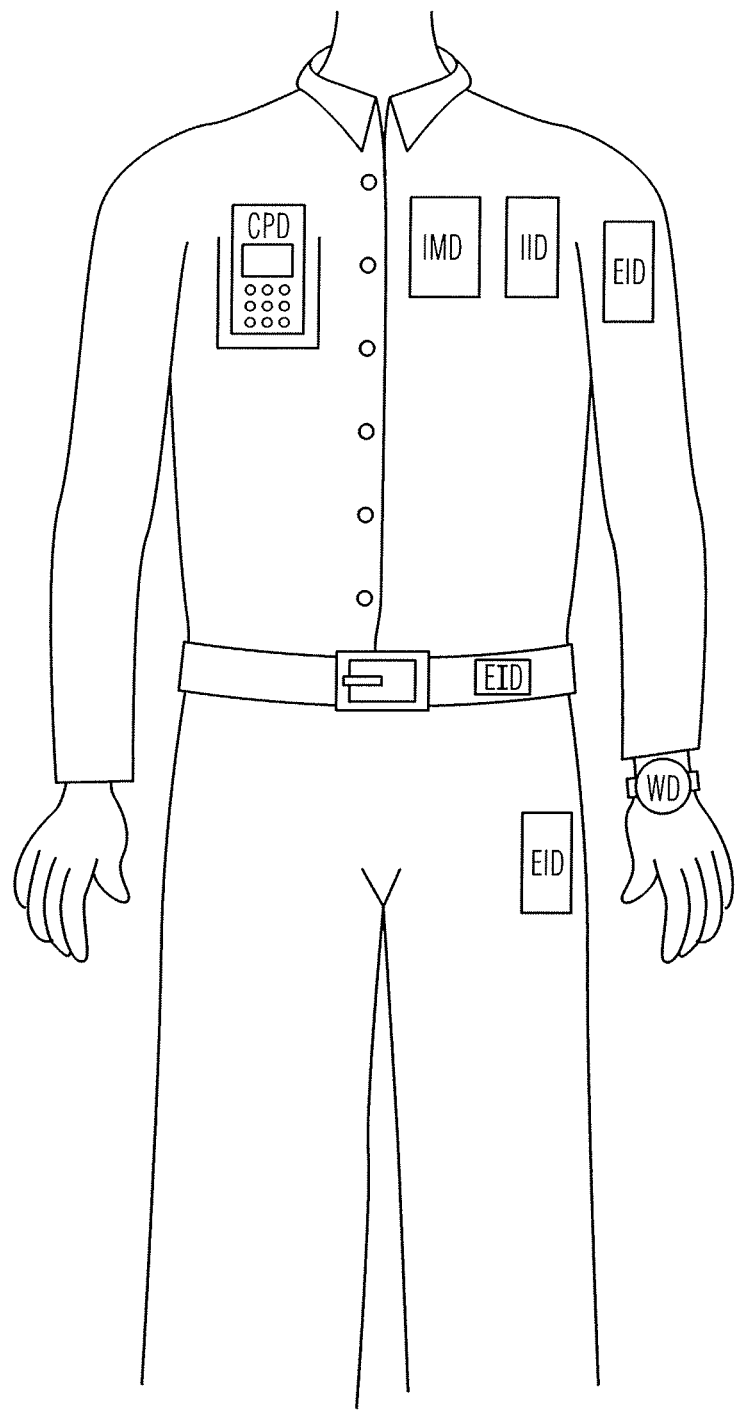
FIG. 3 is a representational diagram showing a patient with an IMD, an internal repeater unit, and multiple external repeater units.

FIG. 3 illustrates the same concept, but does so for the very immediate environment of the patient. A cell phone device is in the patient's shirt pocket. EIDs (external RFIDs) are shown on or in the patient's belt, on or in a shirt and pants. In the case of a female patient, they could be in a blouse or skirt, if desired. In addition, an IID (an implanted RFID) is also shown. The IID could be part of the IMD, could be separate from the IMD but in close proximity to it (or touching it) or could be implanted elsewhere in the body of the IMD owner the person in whom the IMD is implanted). For example it can be adapted to be implanted subcutaneously in the body whereas IMD is implanted at a deeper level than the subcutaneous layer. In addition, a wrist device is shown on the patient's wrist. This is an exemplary figure, and it is unlikely that any one person would have or need the large number of relay devices shown in the figure. Other possible locations for communication devices include an ankle bracelet, a device in a patient's wallet, a device in a handbag, pocketbook, fanny-pack, necklace, eyeglasses or hearing aid.

Figure 4:
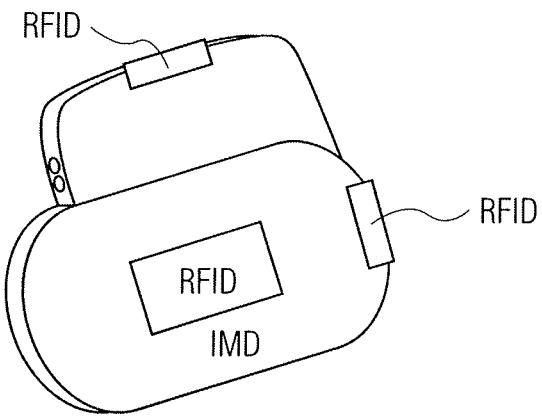
FIG. 4 is a representational diagram showing an IMD with attached RFIDs.

FIG. 4 shows an example of an IMD with three RFIDs attached to it. The intention of the figure is to illustrate a number of possible RFID locations. The RFID would not be powered by the device; Communication circuits which are directly powered by the IMD are considered to be part of the IMD. If the IMD is an ICD, the following additional considerations obtain:

Care would be taken to prevent damage to the RFID at the time of defibrillator discharge;

Care would be taken to prevent the IMD from effectively decreasing the conductive surface area of the can of the ICD to the extent that the transcardiac voltage and current gradients would be meaningfully altered; and It might be possible for the IMD to passively obtain some energy for self supply at the time of an ICD discharge.

Figure 5:
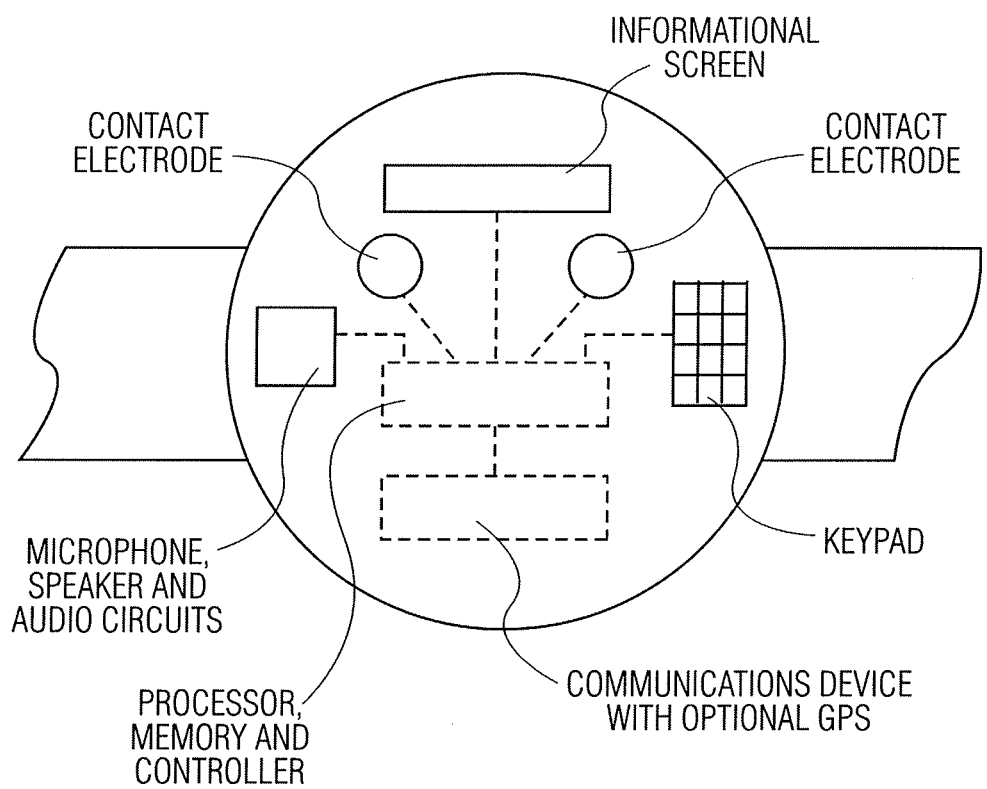
FIG. 5 is a representational diagram showing a wrist communications device.
Figure 6:
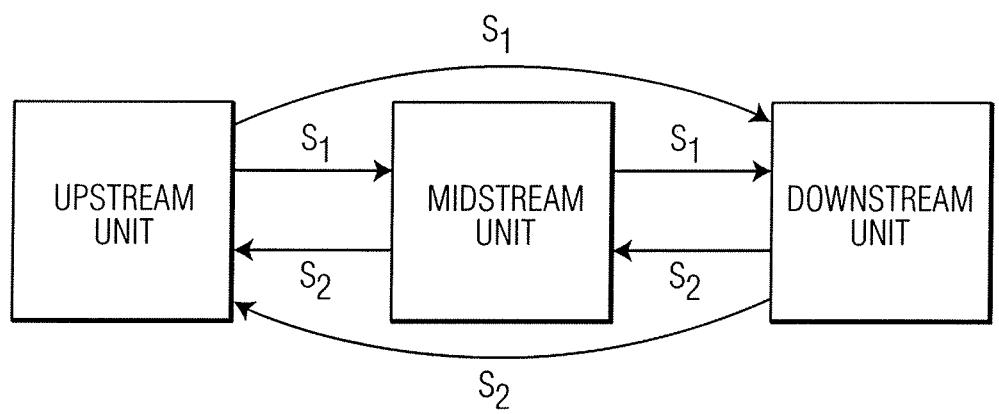
FIG. 6 is a block diagram showing handshake signals exchanged between communication units of the system.

FIG. 5 shows a wrist device. On the upper surface, a keypad and information screen are shown. The keypad function may be incorporated into the screen via touch-sensitive screen technology. A communications unit allows the WD to function as both a relay device and as a patient locator device. An optional GPS device could assist with the locator function. The contact electrodes assure that the device is being worn by the patient. In the absence of contact, the device itself may signal the patient (e.g. with a sound), or the device may communicate with another device in the patient's environment (e.g. CPD) to let the patient know that the WD is not being worn. The processor/memory/controller controls the transmitter, the receiver, the information screen and the audio circuits, may store partially or completely transmitted information being sent in either the upstream or the downstream direction, may store encryption/decryption information, monitors and tests WD performance and performs other functions familiar to those skilled in the art. The microphone and speaker allow audio communication between the device and the wearer [e.g. a) to tell the patient that he is moving out of range of reliable communications, b) to allow a medical professional in a CS to speak with the patient, and c) to notify the wearer of a need for service of the WD itself]. Embodiments of the WD with fewer of these functions are possible. Proper communication between CS and IMD is monitored and enhanced by a number of features discussed in conjunction with FIGS. 6 through 24B. The exchange of beacon or handshake signals between adjacent or non-adjacent units is shown in FIG. 6, and is discussed in the specifications of U.S. Pat. No. 7,277,752 and U.S. patent application Ser. Nos. 11/502,484, 11/895,934, and 12/154,079. Referring to FIG. 6, the word "upstream" refers to the direction from the IMD to the CS, and the word "downstream" refers to the direction from the CS to the IMD. Using this terminology, for example, the CPD is downstream from the SU but upstream from the IMD. One therefore may refer to three communication units that lie between the CS and the IMD (and which may include the CS and the IMD) as upstream, midstream and downstream, where the word "midstream" refers to a communications unit which lies between an upstream and a downstream unit. An example of an upstream, midstream and downstream unit is an SU, a CPD and a WD, respectively. Another example is the CS, a SU and a CPD, respectively. At times, hereinbelow, an upstream unit is referred to as an "alpha" unit and a downstream unit is referred to as a beta unit.

In the terminology used herein, S1 signals are beacon or handshake signals sent from any unit to another further downstream, requesting a response from the downstream unit, while S2 signals are the response. The signals may involve adjacent units (e.g. the upstream and midstream unit), or non-adjacent units (the upstream and downstream units). There may be a 1:1 relationship between the number of S1s and the number of S2s (the format of U.S. Pat. No. 7,277,752), or a many to one relationship (discussed herein). Other types of communication informational signals (discussed hereinbelow) may be exchanged as part of the process of communications enhancement (e.g. downstream unit indicates to upstream unit that S1 intensity is declining). Other types of communication management protocols and numerous variations will be familiar to those skilled in the art.

Figure 7:
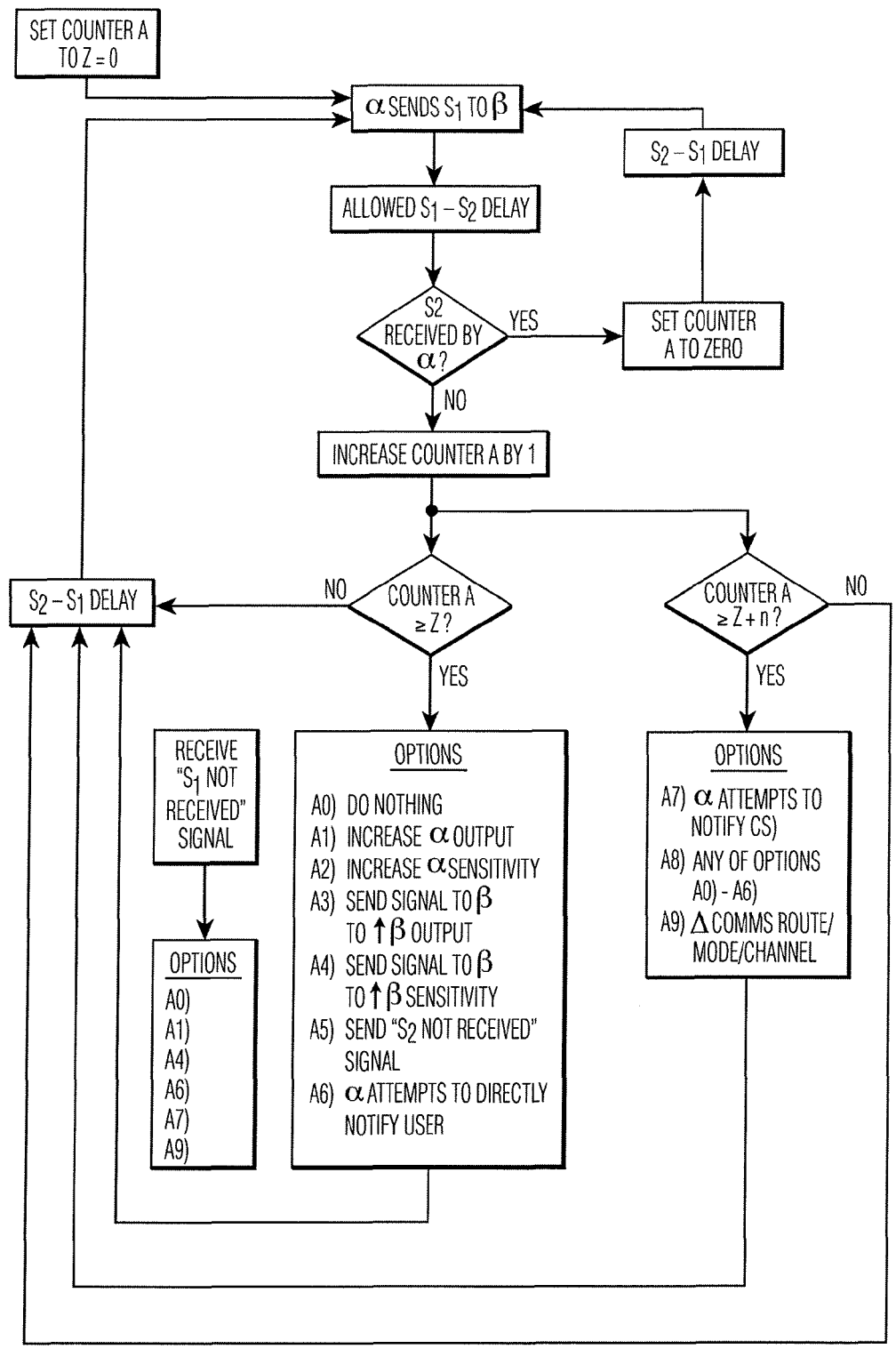
FIG. 7 is a flow diagram showing communication management by an upstream unit using a counter.

FIG. 7 shows an example of an algorithm for handshake management at an upstream communications unit, in one format for communication between an upstream and a downstream communication unit: Beacon signals—referred to herein as "S1"s—are emitted by the upstream unit, after which the upstream unit determines whether a response to the S1—by the emission of an "S2" signal by a downstream unit which has received the S1 signal—has occurred. In the FIG. 7 algorithm, a satisfactory response to the repetitive S1 beacon signals is the receipt of at least one S2 out of every Z emitted S1s, where Z is an integer. The "allowed S1-S2 delay" in the figure determines the extent of time allowed for an S2 response after an S1 is emitted. The S1-S1 frequency may be determined by either:

a) the sum of the allowed S1-S2 delay and the "S2-S1 delay"; or b) the sum of the actual S1-S2 interval and the S2-S1 delay.

Possible management options for non-response after Z and after Z+n S1s are shown in FIG. 7.

Other algorithms are possible with which:

a) there are fewer or more options in each "tier" or group of options, where the first tier in the current algorithm is defined as the regime wherein the value of counter A ranges from Z up to Z+n−1, and the second tier in the current algorithm is defined as the regime wherein the value of counter A is greater than or equal to Z+n;

b) some of the options listed for the first tier (value of counter A being>the number Z), are instead listed for the second tier (value of counter A being>or equal to the number Z+n);

c) option A7 is instead listed for the first tier;

d) Z is the number "1", in which case one S2 is expected for each S1;

e) Z is a non-fixed number, whose value may depend on one or more other parameters (e.g. GPS related information, the importance of a transmission as indicated by the sender, recent communication history details etc.);

f) n is a non-fixed number, whose value may depend on one or more other parameters (e.g. GPS related information, the importance of a transmission as indicated by the sender, recent communication history details etc.); and/or g) there are fewer or more tiers.

FIG. 7 also indicates possible responses to an "S1 not received" signal from a downstream unit.

Figure 8:
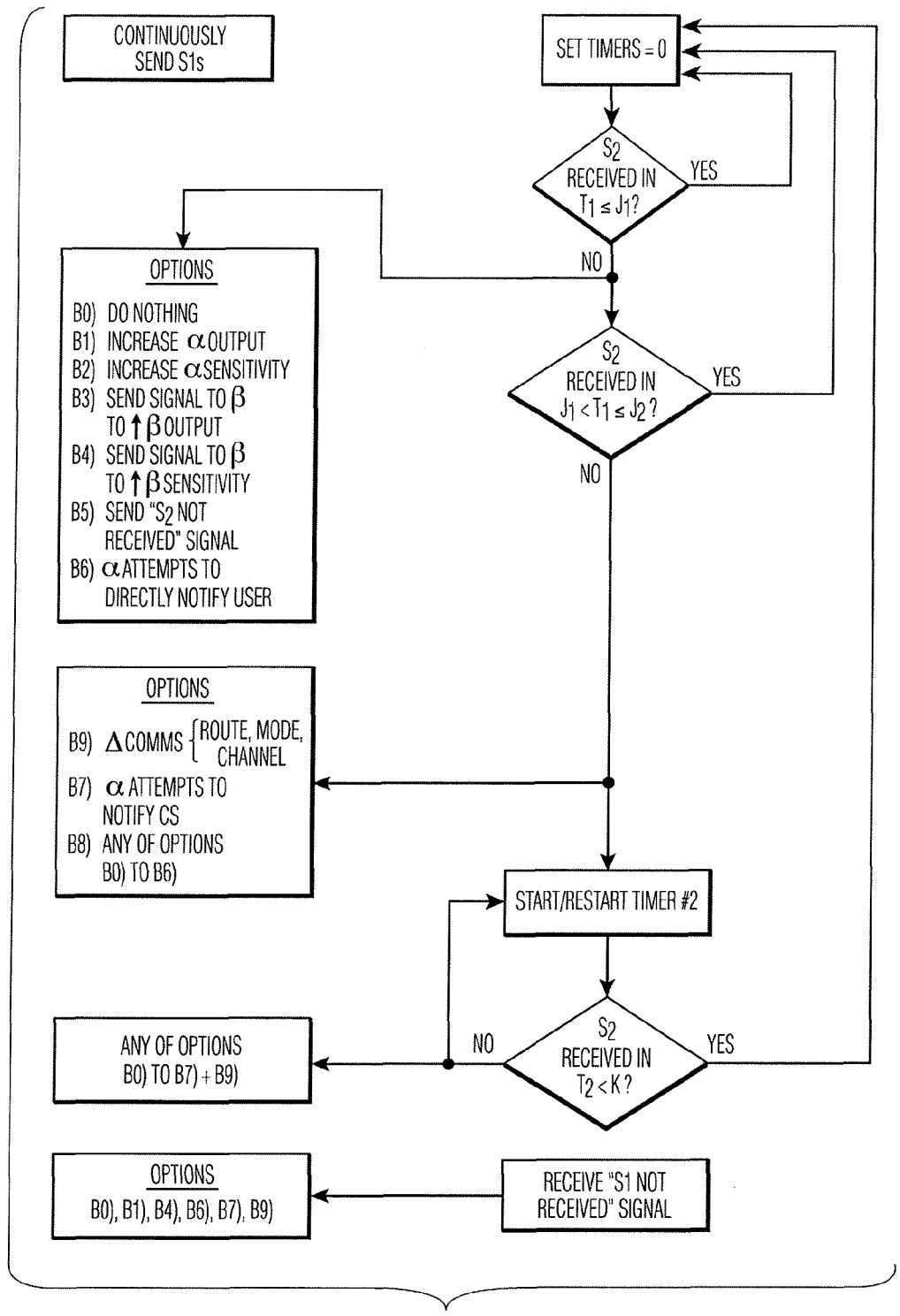
FIG. 8 is a flow diagram showing communication management by an upstream unit using a timer.

FIG. 8 shows an example of an algorithm for handshake management at an upstream communications unit, in another format for communication between an upstream and a downstream communication unit: In this format, a handshake interruption is indicated at the upstream unit by non-receipt of an S2 response after a certain amount of time (as opposed to the case shown in FIG. 7, i.e. non-receipt of an S2 response after a given number of S1s). S1s are continuously emitted. When received downstream; the downstream communications unit returns an S1.

If an S2 is not received within the ordinarily expected interval (designated $J_1$ in the figure), options B0 to B6 are possible choices. If an S2 is still not received by time $J_2$ then options B7, B8 and B9 are possible choices. If an S2 is still not received after an additional interval of K, then any of options B0 to B7, and B9 are possible, and each may be repeated every K seconds thereafter until an S2 is received.

Other Algorithms are Possible with:

a) fewer or more options in each "tier", where the definition of tier is analogous to that of FIG. 7, i.e. a group of options available for a given contingency, e.g. options B0 through B6;

b) some of the options listed for the first tier are instead listed for the second tier;

c) one or more of options B7 and B9 are instead listed for the first tier;

d) The value of $J_1$ is equal to the value of the S1-S1 interval, so that one S2 is expected for each S1;

e) $J_1$ is a non-fixed value, which changes from circumstance to circumstance, whose value depends on one or more other parameters (e.g. GPS related information, the importance of a transmission as indicated by the sender, recent communication history details etc.);

f) $J_2$ is a non-fixed value, which changes from circumstance to circumstance, whose value depends on one or more other parameters (e.g. GPS related information, the importance of a transmission as indicated by the sender, recent communication history details etc.);

g) K is a non-fixed value, which changes from circumstance to circumstance, whose value depends on one or more other parameters (e.g. GPS related information, the importance of a transmission as indicated by the sender, recent communication history details etc.); and/or h) fewer or more tiers.

FIG. 8 also indicates possible responses to an "S1 not received" signal from a downstream unit.

Figure 9:
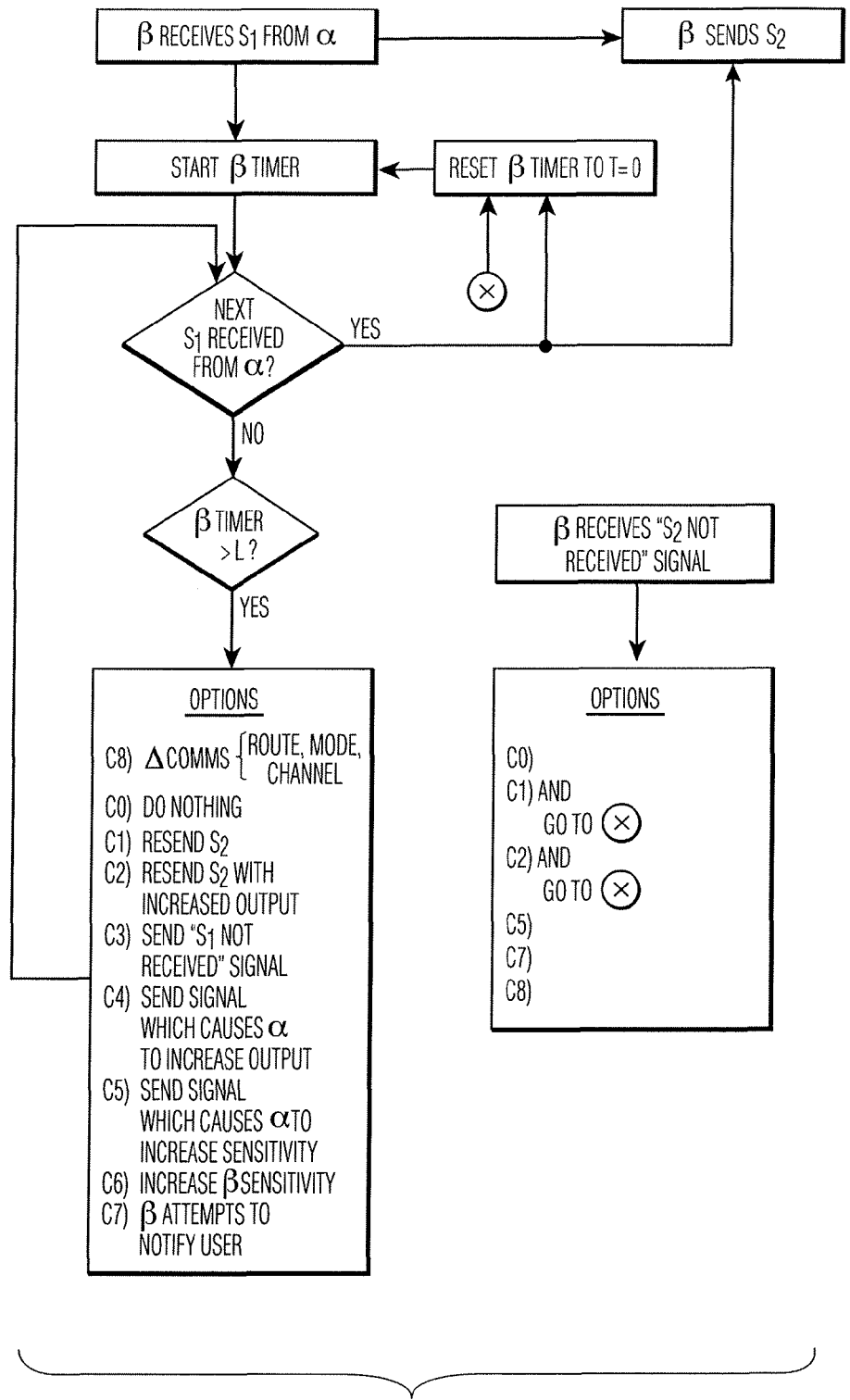
FIG. 9 is a flow diagram showing communication management by an downstream unit using a timer.

FIG. 9 shows an example of an algorithm for handshake management at a downstream communications unit, in a format for communication between an upstream and a downstream communication unit which is complementary to that of FIG. 8 (i.e. FIG. 8 shows a complementary upstream algorithm which could be used with the downstream algorithm described herein).

In this format, a handshake interruption is indicated at the downstream unit by non-receipt of an S1 after a certain amount of time since the last received S1. S1s are continuously emitted by the upstream unit. When an S1 is received downstream; the downstream communications unit returns an S2, and also starts a timer which allows for determination of whether the next S1 is received within an interval L which equals the S1-S1 interval. (The S1-S1 interval may be an industry standard or may be signaled to the downstream unit previously by the upstream unit.) If the next S1 is received within the time L, the timer of this downstream unit is reset; if not, options C0 to C8 are possibilities.

Other Algorithms are Possible with:

a) fewer or more options in the event of a non-received S2;

b) L is a non-fixed value, which changes from circumstance to circumstance, whose value depends on one or more other parameters (e.g. GPS related information, the importance of a transmission as indicated by the sender, recent communication history details etc.); and/or c) more tiers.

FIG. 9 also indicates possible responses to an "S2 not received" signal from an upstream unit.

Figure 10:
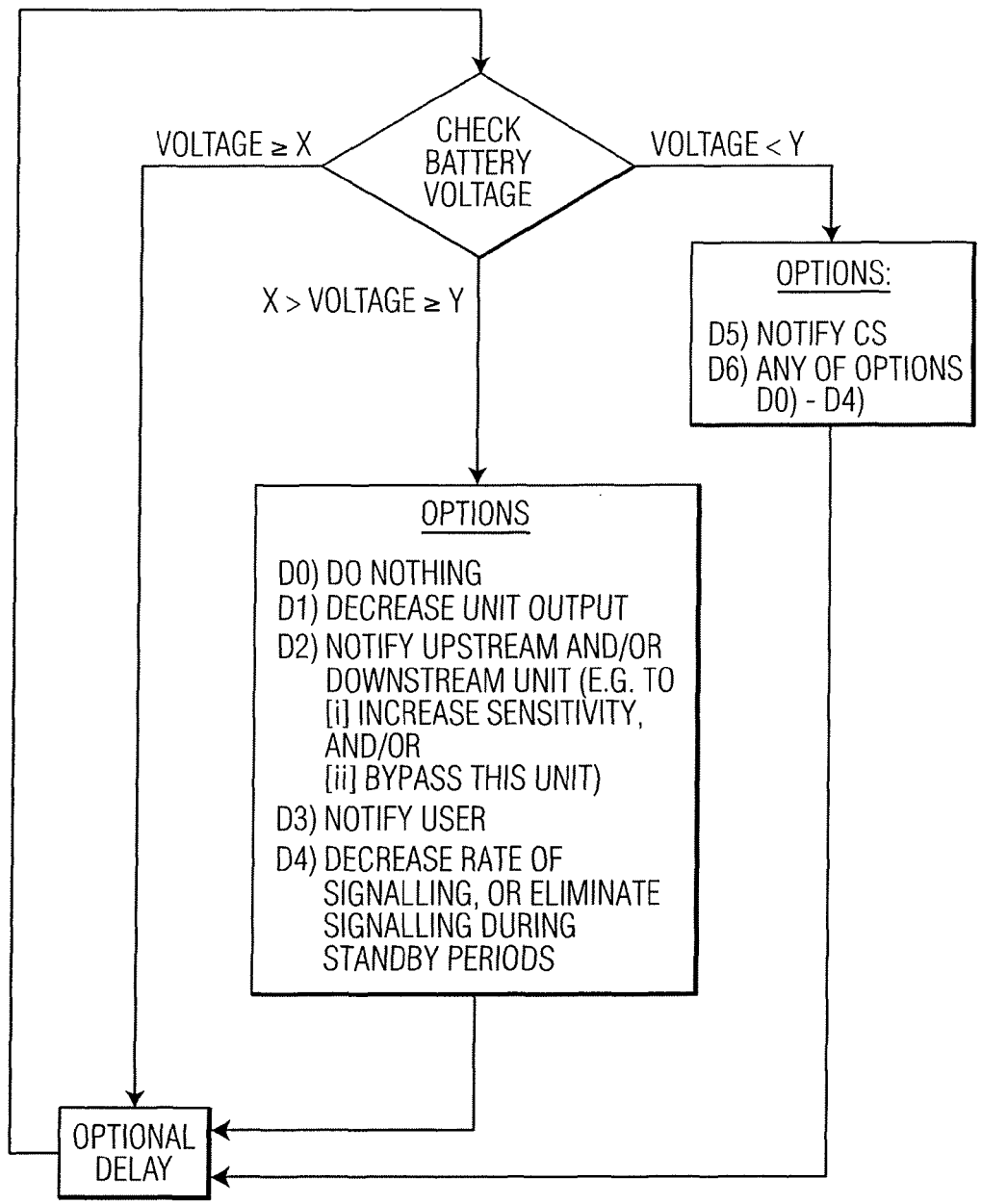
FIG. 10 is a flow diagram showing the use of battery reserve assessment to manage communications.

Careful management of the energy which remains in the battery or batteries of a portable device, and especially careful management of the energy which remains in the battery or batteries of an implanted device are important to maximize the duration of use of these devices (before recharge, battery replacement, or device replacement is necessary). Such management is one of the subjects of the patent and applications incorporated herein by reference. FIG. 10 herein shows an algorithm that allows for using measurements of battery reserve to:

a) decrease power consumption, if possible, b) notifying the IMD owner and/or the CS of a declining level of power reserve, and c) if necessary, bypassing a communications unit with a failing battery.

The algorithm calls for the monitoring of "battery voltage" but other parameters of battery reserve could be used including:

a) the impedance of one or a combination of the individual batteries, if there is more than one;

b) the duration of time since the battery was either charged, replaced or installed; and c) a summation of current drain (as a function of time) multiplied by the time of such current drain, i.e. to generate an estimate of the number of amp-hours that a battery has been used while taking into account that current drain is not constant.

Furthermore, voltage details could be examined including:

a) the voltage of one or a combination of the individual batteries, if there is more than one;

b) the voltage at times that the unit is quiescent, or relative so; and c) the voltage at times of relatively high power drain (e.g. during high voltage capacitor charging of an ICD, or at times that transmitter power is maximal).

FIG. 10 shows a two tiered approach to using battery reserve information for device/system management. Power consumption may be managed by decreasing the power output during transmissions or decreasing the rate at which handshake or other "housekeeping" signals are exchanged. Other methods of power savings include less storage and analysis of non-essential information. The user may be notified by either a message delivered (see hereinbelow in conjunction with FIG. 14) from the device with the declining battery reserve, or by a message sent from the device with the low reserve to another device which performs the notification function (e.g. a wrist device with declining battery voltage notifies the cell phone device of same, which in turn notifies the user). The purpose of the optional delay is shown in the figure to modulate the frequency of notification of low voltage or reaction to it.

Embodiments of the invention are possible with:

a) fewer or more tiers than the number shown in the figure;

b) no monitoring of battery reserves;

c) a substantially continuous relationship between battery reserve and power consumption, rather than a stepwise one; and d) sharing the information about battery reserves with either (i) the adjacent communication units [defined hereinbelow in conjunction with FIG. 18], (ii) a communication unit which has been designated as either the local communications controller or the system communications controller [see hereinbelow].

Other techniques for battery conservation and management will be apparent to those skilled in the art.

Figure 11:
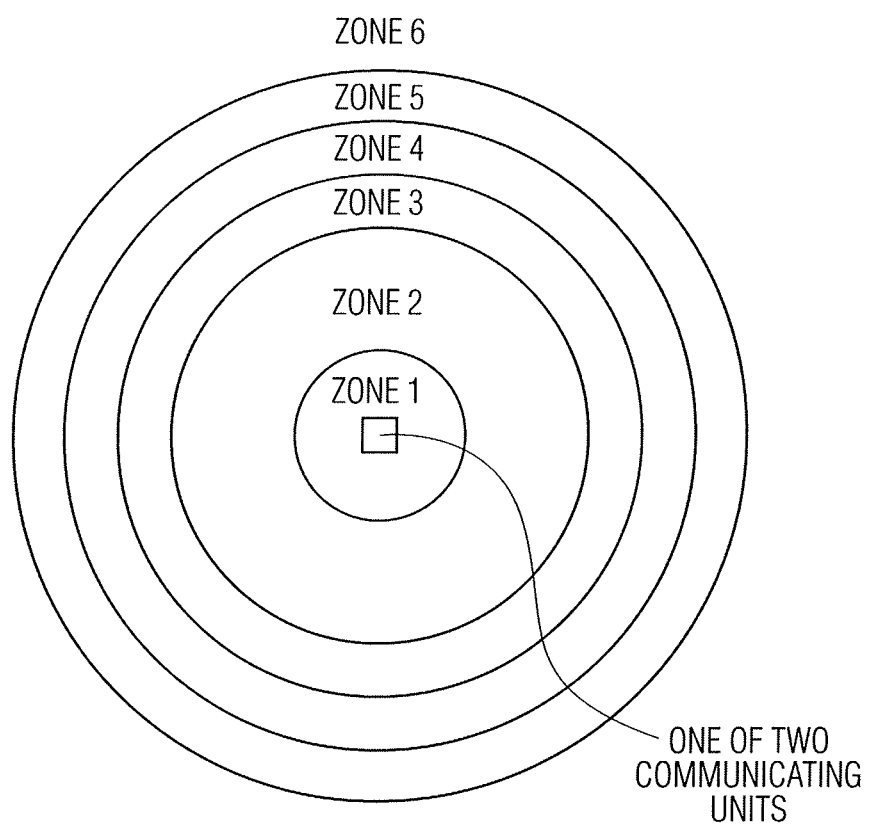
FIG. 11 is a representational diagram showing a possible geometric relation between the distance from a signal source and the quality of the received signal.
Figure 12:
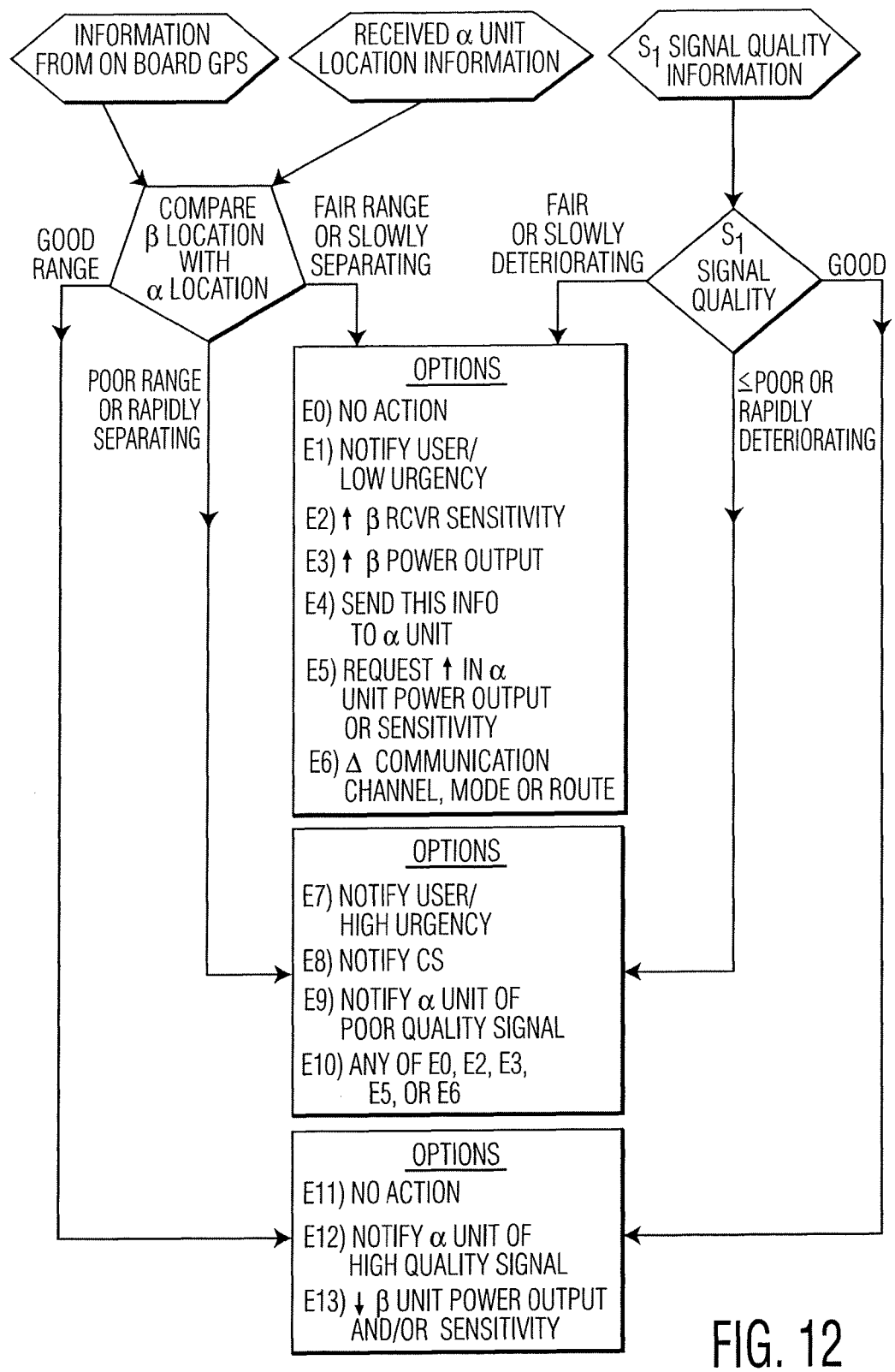
FIG. 12 is a flow diagram showing the use of GPS information, and information about the quality of a signal which originates upstream, to manage communications at the downstream end.
Figure 13:
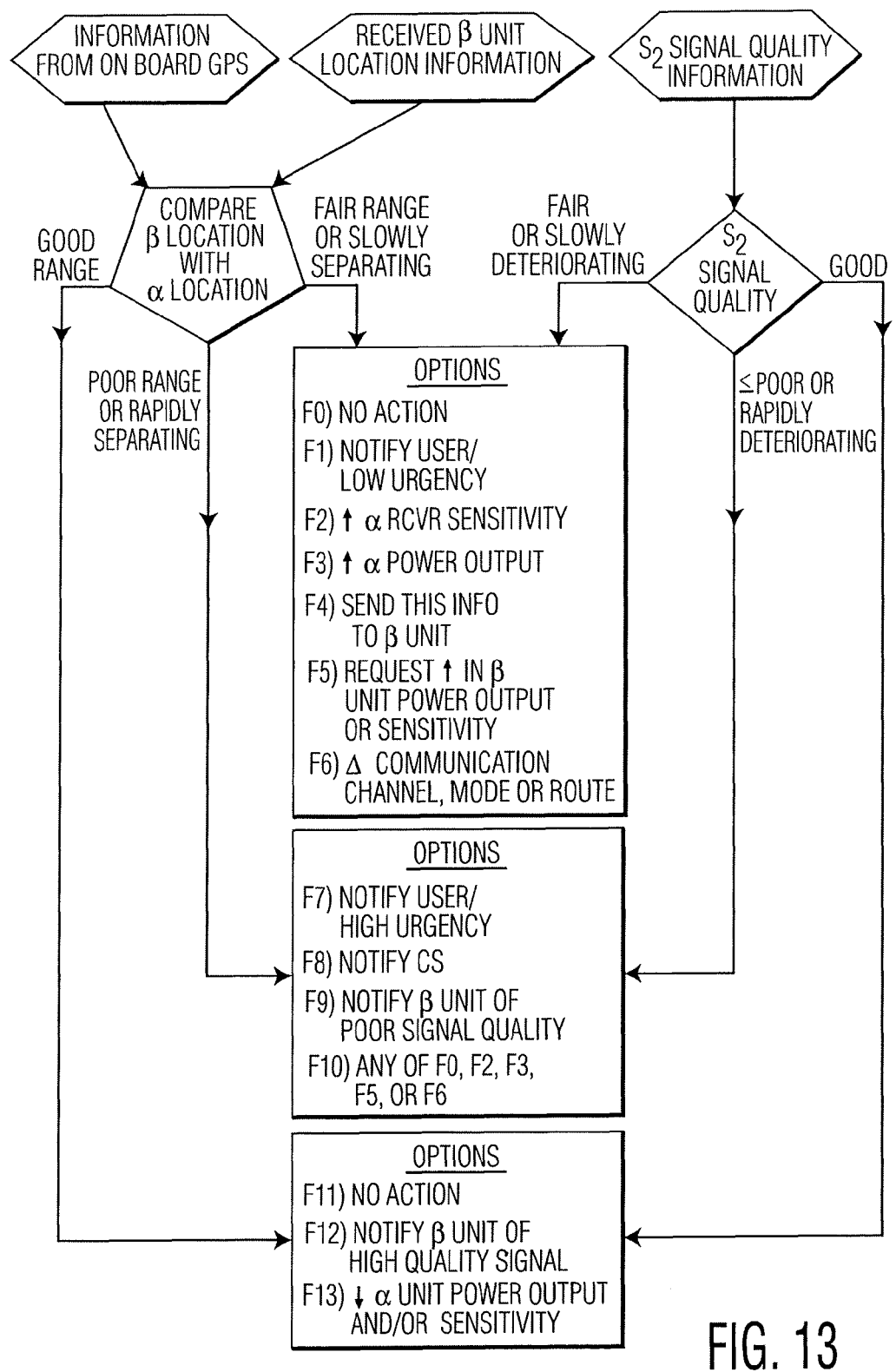
FIG. 13 is a flow diagram showing the use of GPS information, and information about the quality of a signal which originates downstream, to manage communications at the upstream end.

FIGS. 11-13 show how the analysis of:

a) the relative positions of two communicating units;

b) relative movement of two communicating units;

c) the strength of the received signal at each respective unit; and/or d) the rate of change in signal strength.

may be used to optimize communications between the two units.

FIG. 11 shows an example of a method of categorizing the relative positions of two communicating or potentially communicating units. The location of one such unit is indicated by the square in the center of the figure. If the location of the second such unit is within Zone 1, i.e. near the first unit, then one expects that signal quality at each of the two units should be good. If the second unit is in Zone 2, one expects less signal strength at each of the two receivers than is the case for the second unit being in Zone 1; etc. for Zones 3, 4, 5 and 6. FIG. 11 shows one of an essentially infinite number of possible examples. Variations include:

a) a greater or lesser number of zones;

b) a substantially continuous relationship between the distance between communicating units and a parameter (e.g. output power) which is adjusted based on distance;

c) zones which may all be the same width, zone widths which bear an algebraic relationship to distance (e.g. width of zone decreases as the square or cube of the distance); or zone widths which have a non-algebraic relationship to distance, or no relationship to distance;

d) zone shapes which may not be radially symmetric, and some or all zones which are shaped differently than other (or all other) zones; and e) zone shapes and/or sizes which are constant in time vs. zone shapes and/or sizes which vary with time (e.g. variation as battery reserve falls or variation as the device/device antenna orientation varies, as weather varies, as sunspot conditions vary and/or as obstacles vary).

In one or more embodiments of the invention, a zone-based and/or distance [between communicating units]-based format:

a) may not be used at all (e.g. a format based on signal strength or change in signal strength may be used);

b) may be used intermittently; or c) may be used as one of a number of parameters which are inputted in the optimization of communications.

FIG. 12 shows an algorithm which uses both GPS information and signal strength information to optimize communications at the downstream or beta end of a communicating pair of devices (e.g. IMD and WD). Algorithms are possible which use only GPS information, only signal strength information, both, or either one or both plus additional information (e.g. battery reserve, urgency of transmission, etc.). For both position and signal strength, algorithms are possible in which the rate of change of either of these parameters:

a) is used along with the parameter itself;

b) is used instead of the primary parameter; or c) is not used at all.

Algorithms are also possible in which a higher order derivative of either parameter is used, e.g. acceleration (i.e. the second derivative of position with respect to time) alone, or in addition to the other parameters mentioned herein.

Signal quality has been divided into "good", "fair" and "poor". In addition a slowly deteriorating signal has been classified as fair, and a rapidly deteriorating one has been classified as poor. Similarly, distance has been classified as good, fair and poor; and a slowly increasing distance has been classified as fair, while a rapidly increasing distance as poor. Algorithms are possible in which the information concerning rates of change of position and signal strength are used in different ways than in the algorithm in the example; many such approaches will be obvious to those skilled in the art.

The pentagon symbol in FIGS. 12 (and 13) is conceptually similar to that of a diamond-shaped object in a flow diagram: It indicates three possible choices (the lower three corners) where the choice is made by comparing a) information inputted at the upper left corner with b) information inputted at the upper right corner. Thus, the pentagon shape in FIG. 12 indicates that the information from the onboard GPS (i.e. the beta unit's GPS) is compared with information which was transmitted from the upstream (alpha unit's) GPS: If the comparison shows that the relative positions are in a good range, then the left-most corner of the pentagon leads to options E11 through E13. If the comparison shows that the relative positions are in a fair range (or are slowly separating), then the right-most corner leads to options E0 through E6. If the comparison shows that the relative positions are in a poor range (or are rapidly separating), then the lower-most corner leads to options E7 through E10.

Algorithms are possible with:

a) a greater number of tiers of classification and therapy;

b) a lesser number of tiers of classification and therapy;

c) the same "curative" options differently distributed among the tiers;

d) a smaller or larger number of curative options; and/or e) different curative options.

FIG. 13 shows an algorithm which uses both GPS information and signal strength information to optimize communications at the upstream or alpha end of a communicating pair of devices (e.g. IMD and WD). The differences, therefore between FIGS. 12 and 13 are related only to this, and reflect the complementary nature of the two. For example, the inputs are reciprocally different, e.g. in FIG. 12, the downstream unit looks at the signal strength of the S1, while in FIG. 13, the upstream unit looks at the signal strength of the S2. For the same reasons, some remedies are changed reciprocally—e.g. FIG. 12 has option E3 as an increase beta unit's power output, while FIG. 13 has an increase alpha unit's power output as option E3. Embodiments of the invention in which the algorithms are not reciprocally related are possible, e.g. in which the options for poor signal quality at the alpha unit are different than the options for poor signal quality at the beta unit.

Referring to both FIGS. 12 and 13, options E1, E7, F1 and F7 involve "user" (i.e. the IMD owner) notification, and are further discussed hereinbelow, in conjunction with FIG. 14. Options E8 and F8 involve notification of the central station (and perhaps, thereafter, the user/IMD owner). Options E2-E5, E9, E12, E13, F2-F5, F9, F12 and F13 involve modification of communications with one of the two adjacent communicating units. Options E6 and F6 involve changes which may affect one or both adjacent units (e.g. bypassing a unit, as shown hereinbelow in FIG. 19A and discussed in conjunction with the associated specification), or even changes that affect units which are more distant than the adjacent ones.

In the event of either:
  a) deteriorating communication conditions (the deterioration likely to concern the less robust
    links, i.e. one or more of the links in the vicinity of the IMD), or
  b) an inability to communicate between IMD and one of the repeater units in its vicinity,
then a means of notifying the IMD owner [i.e. the person in whom the IMD is implanted] is desirable.

Notification is discussed generally first, and an exemplary algorithm is discussed hereinbelow in conjunction with FIG. 14.

The notification itself may be delivered:
  a) by a phone call to the IMD owner's CPD;
  b) by a verbal announcement coming from a WD or CPD (e.g. a previously stored voice prompt);
  c) by a tone, chime, vibration, screen message, flashing light source, etc. from a WD or CPD; or
  d) by a tone, chime, buzzing, computer screen message, television screen message, flashing light source, etc. from a stationary source in the IMD owner's home, workplace, motor vehicle, or any other place likely to be frequented by the IMD owner; or
  e) by any device or means which will attract the attention of the IMD owner.

Alternatively (or if none of the above means is successful in obtaining the attention of the IMD owner), notification of a spouse, other family member (who preferably but not necessarily live with or near the IMD owner), neighbor or colleague in the workplace may be attempted.

FIGS. 7-12 hereinabove each indicate contingencies in which the notification of the IMD owner may be desirable:
  a) a handshake failure between communication units detected at an upstream unit, e.g.:
    i) option A6 [FIG. 7], due to counter A equaling exceeding the value of Z;
    ii) option A8 [FIG. 7], due to counter A equaling or exceeding the value of Z+N;
    iii) option A7 [FIG. 7] (exercised via the CS), due to counter A equaling or exceeding the value of Z+N;
    iv) option B6 [FIG. 8], due to timer #1 exceeding the value of J;
    v) option B8 [FIG. 8], due to timer #2 exceeding the value of K; or
    vi) option B7 [FIG. 8] (exercised via the CS), due to timer #2 exceeding the value of K;
  b) a handshake failure between communication units detected at a downstream unit, e.g. option C7 [FIG. 9] due to beta timer exceeding the value L;
  c) a fall in battery voltage at the communications unit which includes the notification mechanism, e.g. options D3 [FIG. 10] and D5 [FIG. 10] (exercised via the CS);
  d) a fall in signal quality at the notification device, e.g. options E1 [FIG. 11], E7 [FIG. 11] and E8 [FIG. 11] (exercised via the CS);
  e) a fall in signal quality at the communications unit which is upstream from the notification device, e.g. options F1 [FIG. 12], F7 [FIG. 12] and F8 [FIG. 12] (exercised via the CS);
  f) a determination by the communications unit which includes the notification device that the distance between it and the upstream communications unit (as determined by GPS) is suboptimal, e.g.:
    option E1 [FIG. 11], due to distance slowly increasing or in a somewhat marginal range;
    option E7 [FIG. 11], option E8 [FIG. 11] (exercised via the CS) due to distance rapidly increasing or in a very marginal range; and
  g) a determination by the communications unit which includes the notification device that the distance between it and the downstream communications unit (as determined by GPS) is suboptimal, e.g.:
    option F1 [FIG. 12], due to distance slowly increasing or in a somewhat marginal range;
    option F7 [FIG. 12], option F8 [FIG. 12] (exercised via the CS) due to distance rapidly increasing or in a very marginal range;

If a medical professional in the CS or elsewhere wishes to remotely access the IMD, and the arrangement with the IMD owner is that the IMD owner's permission is required for such access (see hereinbelow), then the notification device may inform the IMD owner of a permission request. The medical professional may indicate the level of urgency, which may influence the quality of the notification (see hereinbelow).

Other contingencies in which the notification of the IMD owner may be desirable include:
  a) a fall in battery voltage at a communications unit either upstream or downstream from the unit which includes the notification mechanism [and reported to the unit which includes the notification mechanism];
  b) the receipt of a signal by the communications unit which includes the notification device that the distance is suboptimal between two communicating communication units, neither of which is that of the notification device; and
  c) the receipt of a signal indicating that the IMD owner's wrist device is no longer in contact with the IMD owner's wrist, as assessed by (i) a change in impedance between two contact electrodes, or (ii) a change in temperature sensed by the device.

Figure 14:
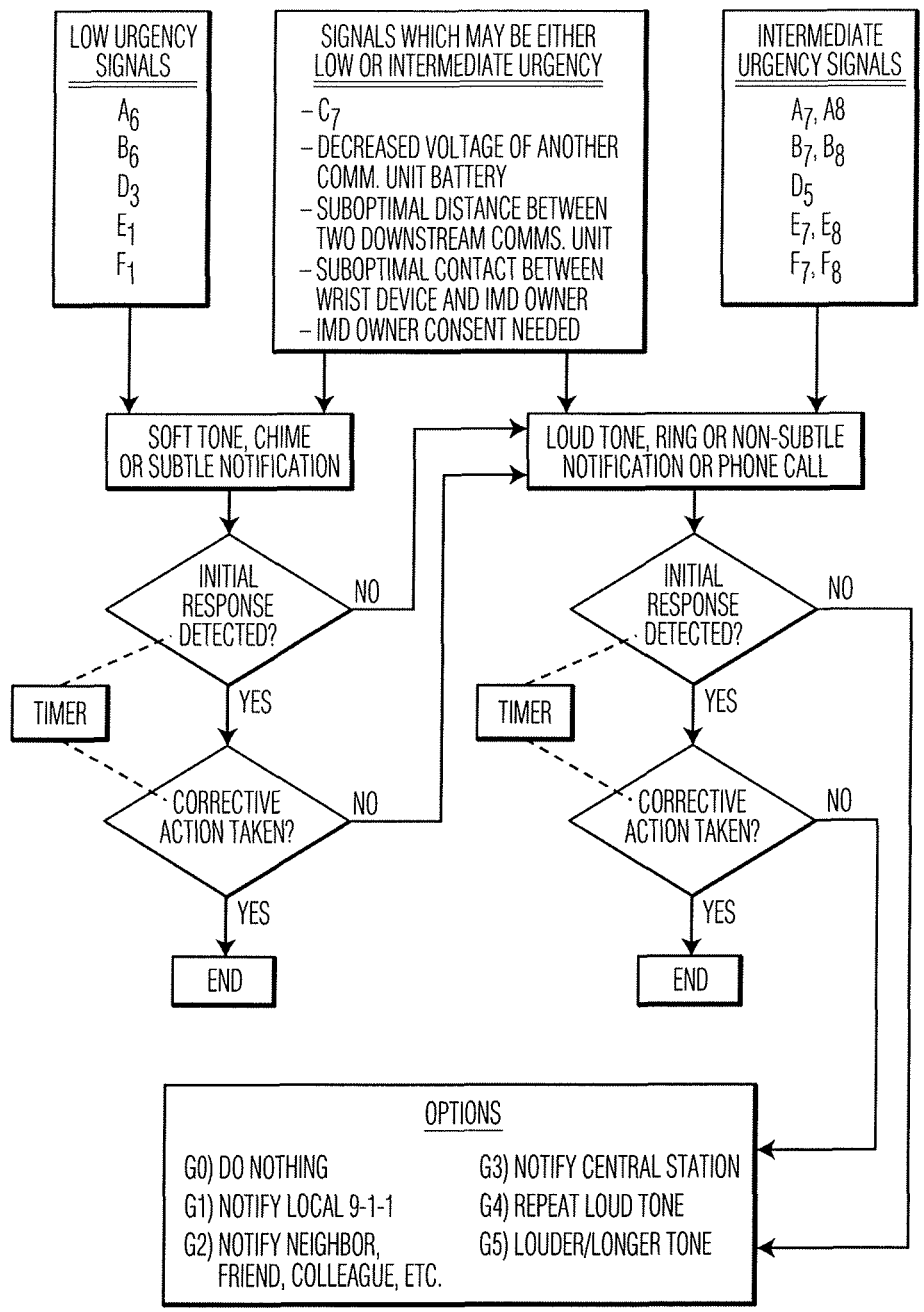
FIG. 14 is a flow diagram showing notification of patient, neighbor, central station administrator etc. in the event of suboptimal communication quality.

FIG. 14 shows an algorithm in which a signal indicating one of the aforementioned contingencies requiring notification results in a gradually more aggressive attempt to notify the device owner or, if necessary, the central station. In the approach shown in FIG. 14, there are two levels of urgency of initial notification, with different types of notification for the low level of urgency (e.g. soft tone) and for an intermediate level of urgency (e.g. loud tone).

The notification algorithm illustrated by FIG. 14 calls for an upgrade of the level of notification from low to intermediate in the event that either:

a) there is no response by the IMD owner to a low level notification; or
b) there is no correction of the low level fault by the IMD owner within a certain time interval.

The notification algorithm calls for an upgrade of the level of notification from intermediate to high in the event that either:
a) there is no response by the IMD owner to an intermediate level notification; or
b) there is no correction of the intermediate level fault by the IMD owner within a certain time interval.

IMD owner notification for a consent is indicated as either low or intermediate urgency, because in a state of high urgency, it is possible or likely that IMD owner consent might be bypassed. Nevertheless, consent formats (see hereinbelow) are possible in which the IMD owner must agree to any and all outside access to his unit; With this format, a consent request of high urgency would be possible. An option such as G5 (louder longer tone) could be employed right from the start in such a circumstance.

Embodiments of the Device are Possible with:
a) a greater number of levels of urgency (and with an equal number of corresponding qualities of notification);
b) a lesser number of levels of urgency;
c) an algorithm in which the quality or type of notification at one level of urgency may be the same as that of another level (e.g. the intermediate level results in production of the same tone as that of the low level), and
d) different sensory effects than the sounds stated in the figure.

The algorithm may be modified to allow either the IMD owner or the CS to:
a) turn off an alarm (e.g. in a situation in which it repeats frequently);
b) modify the criteria for triggering the alarm;
c) modify the quality of the alarm; or
d) modify the amount of time before an alarm occurs (four such intervals shown in the figure).

Many other notification algorithms are possible, and will be obvious to those skilled in the art.

FIGS. 15-27C concern apparatus and methods for using the detection of motion of the IMD owner to reduce battery consumption. The concept is: If at one particular time, the communication quality between the two units of the communication chain between IMD and CS is high, then, if neither of the two units moves, the communication quality is likely to remain high. On the other hand, if one unit is moving with respect to the other, then if the movement results in an increased distance between units that communicate only over a short range, the communication quality may decrease. In a no movement state, the reassessment of communication integrity (e.g. the strength of a received signal, and/or the response to a handshake signal) could occur on a less frequent basis, or might be able to be carried out with a reduction in output power. On the other hand, in a state characterized by movement, it may be desirable to increase the output power or the frequency of reassessment of communication integrity, in anticipation of a possible increase in distance between communicating units.

The case of communication between the CS and an SU is a trivial one, since neither is likely to move. (By definition, an SU does not move, and only limited examples of a mobile CS [e.g. certain peripheral CSs, as defined in U.S. patent application Ser. No. 11/502,484] are possible.) The units that are expected to move from time to time are the IMD itself, an internal RFID if part of the system, an external RFID if part of the system, a WD if part of the system, and a CPD, if part of the system.

Many pacemakers and ICDs have so called rate responsive capability, e.g. can operate in pacing modes such as VVIR, DDDR, etc. Such units detect motion by an onboard piezoelectric crystal, or by an accelerometer, and use the information to modulate pacing rate. However, if information about detected motion was shared with an upstream unit (e.g. an RFID, a WD, or a CPD), then the upstream unit could decrease handshake frequency or signal strength during times when the downstream unit is stationary, thereby conserving battery reserves. The IMD itself could use the motion information to minimize current drain for its own communication management (e.g. decrease power output if communications have been good, and if no detected IMD motion has occurred since the time of good communications.) Including such motion detecting apparatus in a CPD, a WD or an RFID would be possible.

In principle, a communications unit with motion detecting apparatus could be moving at a perfectly constant velocity away from another unit with which it is communicating; Because the velocity in this cited example is constant, neither a piezoelectric crystal nor an accelerometer would detect motion. This would constitute a case where motion detecting apparatus fails to detect such motion. However:
a) There would have to be some acceleration at the start of the motion; and
b) Other systems in place (e.g. apparatus for examining signal strength, response to handshake signals, or GPS signals) could provide additional information which indicates that one communication unit is moving with respect to the other.

Figure 15:
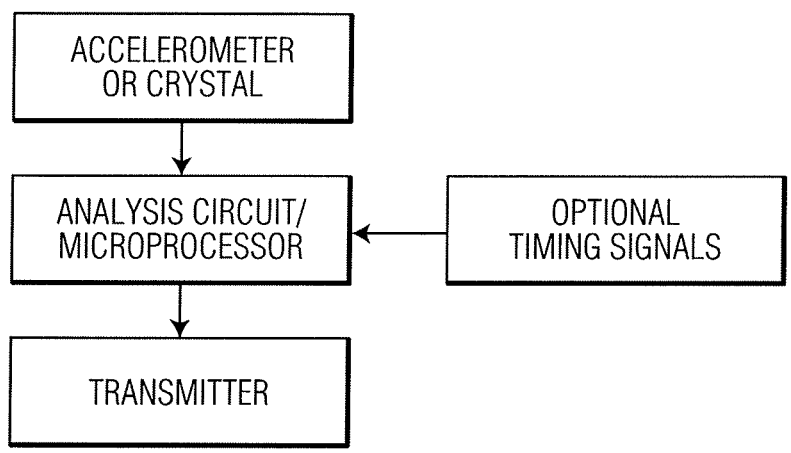
FIG. 15 is a flow diagram showing externalization of signals which carry information about patient motion detected by an IMD.

FIG. 15 shows apparatus for performing this function. The optional timing circuits allow for the determination not only that motion is occurring, but for the determination of a motion vs. time profile. The transmitter may transmit the information to the upstream and/or downstream unit. Furthermore, the unit which contains the motion detection apparatus may use the motion information for its own communication management. If the unit is a pacemaker or ICD, of course, the unit may further use the motion information for modulation of the pacing rate.

Figure 16A:
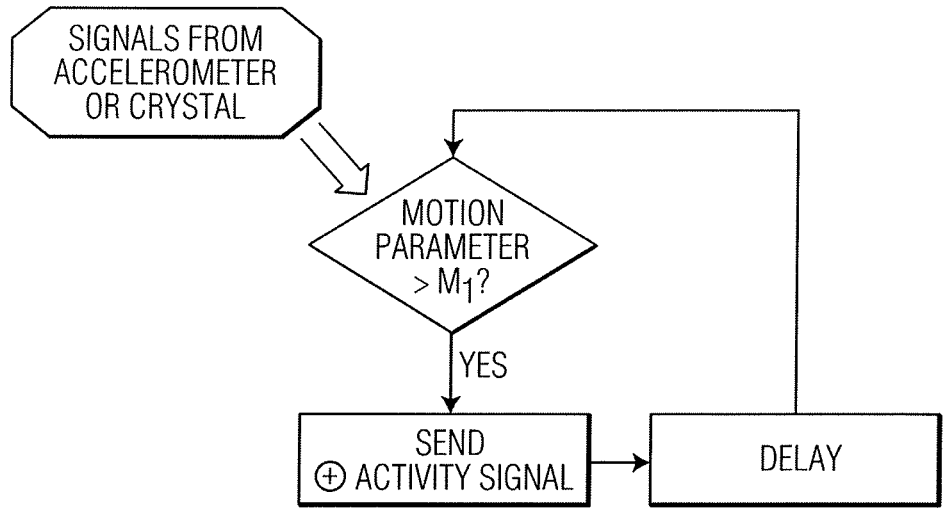
FIGS. 16A and 16B are flow diagrams showing algorithms for the assessment and reporting motion of an IMD.

FIG. 16A shows a simple algorithm for the management of motion information. In the shown algorithm, if a motion parameter exceeds a threshold value, then the information is either a) sent to one or more other communications units, or b) used by the device of which the motion detection apparatus is a part. The motion parameter could examine a) maximum acceleration, b) acceleration above a certain threshold value, c) derived parameters of acceleration [e.g. acceleration squared]; In addition or instead, the motion parameter could examine time-related functions of acceleration, e.g. a) the average acceleration over a period of time, b) a time derivative of a smoothed acceleration parameter, etc. In addition or instead, the motion parameter could examine the output of a piezoelectric device or accelerometer device, such output related to the extent of acceleration. Other appropriate acceleration-based parameters will be obvious to those skilled in the art. Finally, acceleration could be examined along each of a number of different spatial axes. Each component of the multidimensional acceleration information could then be used individually, or the components could be blended to yield a single measure of acceleration. The delay shown in the figure is optional. The intention is to avoid, if practical, a continuous rebroadcast of acceleration information, especially if there is no change in the information with respect to the prior assessment. Embodiment of the invention are possible in which a) there is no delay; b) in which the delay is a fixed value, and c) in which the amount of delay depends on the magnitude of change in the acceleration parameter (i.e. small change leads to long delay).

Figure 16B:
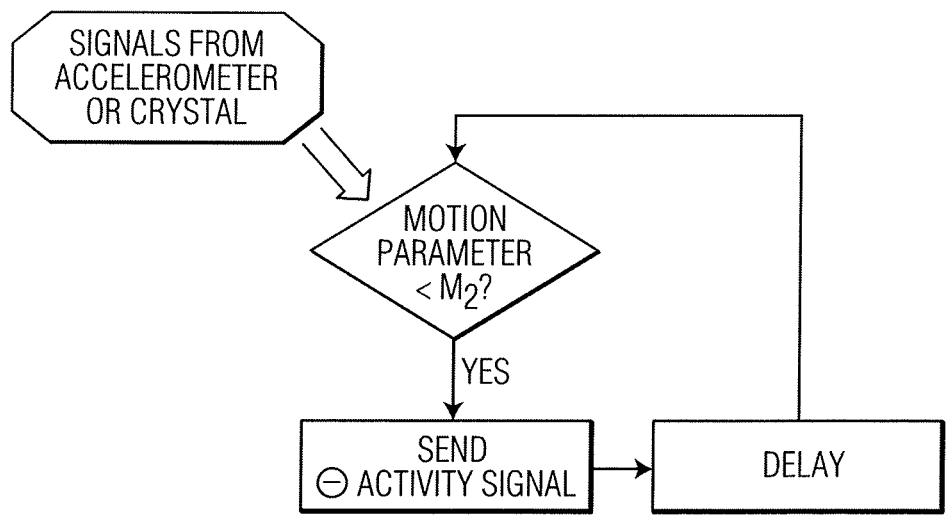

FIG. 16B shows a simple algorithm for the determination of cessation or reduction in motion. Multiple approaches to reporting motion based on FIGS. 16A and 16B are possible including:
 a) the approach shown in FIG. 16A could be used as the sole determinant of motion,
 b) the approach shown in FIG. 16B, in which non-motion (or minimal motion, or a derived parameter which reports minimal motion) is the sole reported item, or
 c) an approach in which both motion and non-motion/minimal motion (or derived parameters of each) are separately assessed in parallel, as shown in FIGS. 16A and 16B.

Figure 17:
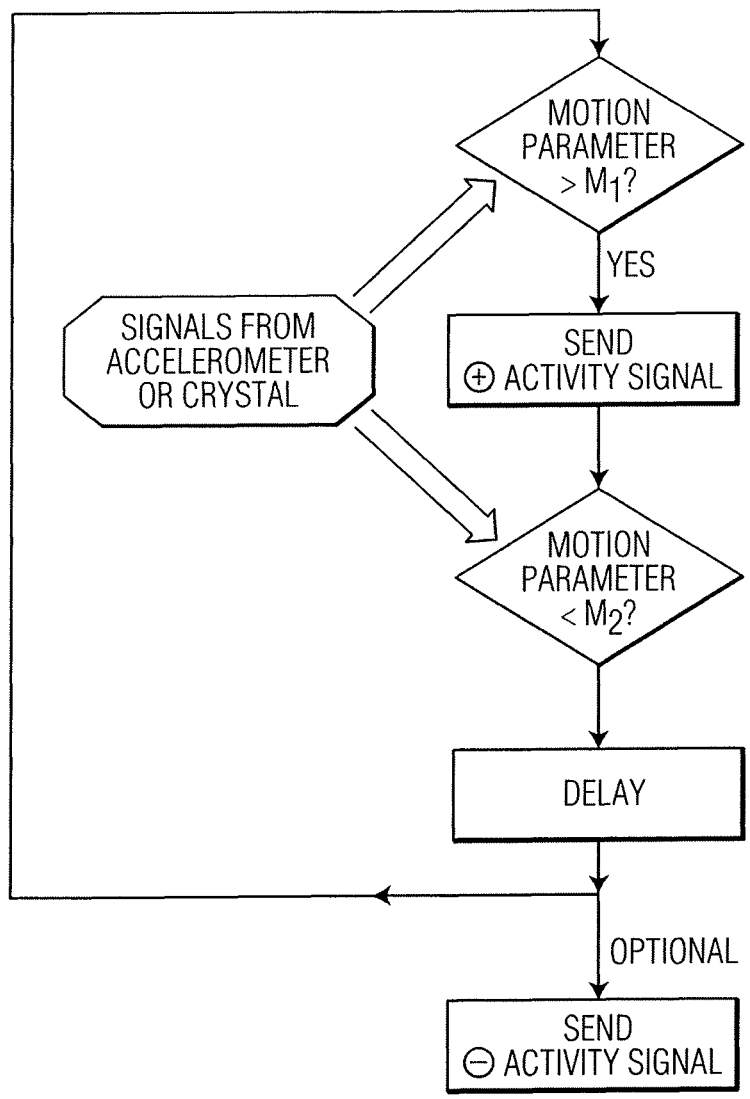
FIG. 17 is a flow diagrams showing another algorithm for the assessment and reporting motion of an IMD.

Furthermore, families of algorithms such as that shown in FIG. 17 are possible, in which a report of motion is not followed by another report of motion until an intervening period of non-motion has been reported. Similarly, a report of non-motion is not followed by another report of non-motion until an intervening period of motion has been reported. This approach also minimizes reporting and thereby may conserve battery reserve. Many configurations of this series approach are possible including:
 a) those in which only positive activity signals are sent;
 b) those in which only negative activity signals are sent;
 c) those in which both positive and negative activity signals are sent;
 d) those with no delays;
 e) those in which there is a single delay, which occurs at a point other than after "MOTION PARAMETER<M2" (e.g. between "SEND+ACTIVITY SIGNAL" and "MOTION PARAMETER<M2");
 f) those with multiple delays (e.g. before "MOTION PARAMETER<M1" and before "MOTION PARAMETER<M2"); and
 g) combinations of a)-f).

FIGS. 18-27C address the complexities of implementing the movement detection system with a many unit communication system, i.e. a system as described hereinabove in which there may be one or many communication relay units which are situated schematically between the IMD and the CS. In the related specification that follows, the sequence of topics is:
 a) Nomenclature and Definitions;
 b) General Principles;
 c) Specific (Simple) Architectures;
 d) Architecture in which All Movable Units have MDC; and
 e) Architecture for a General System

NOMENCLATURE AND DEFINITIONS

Figure 18:
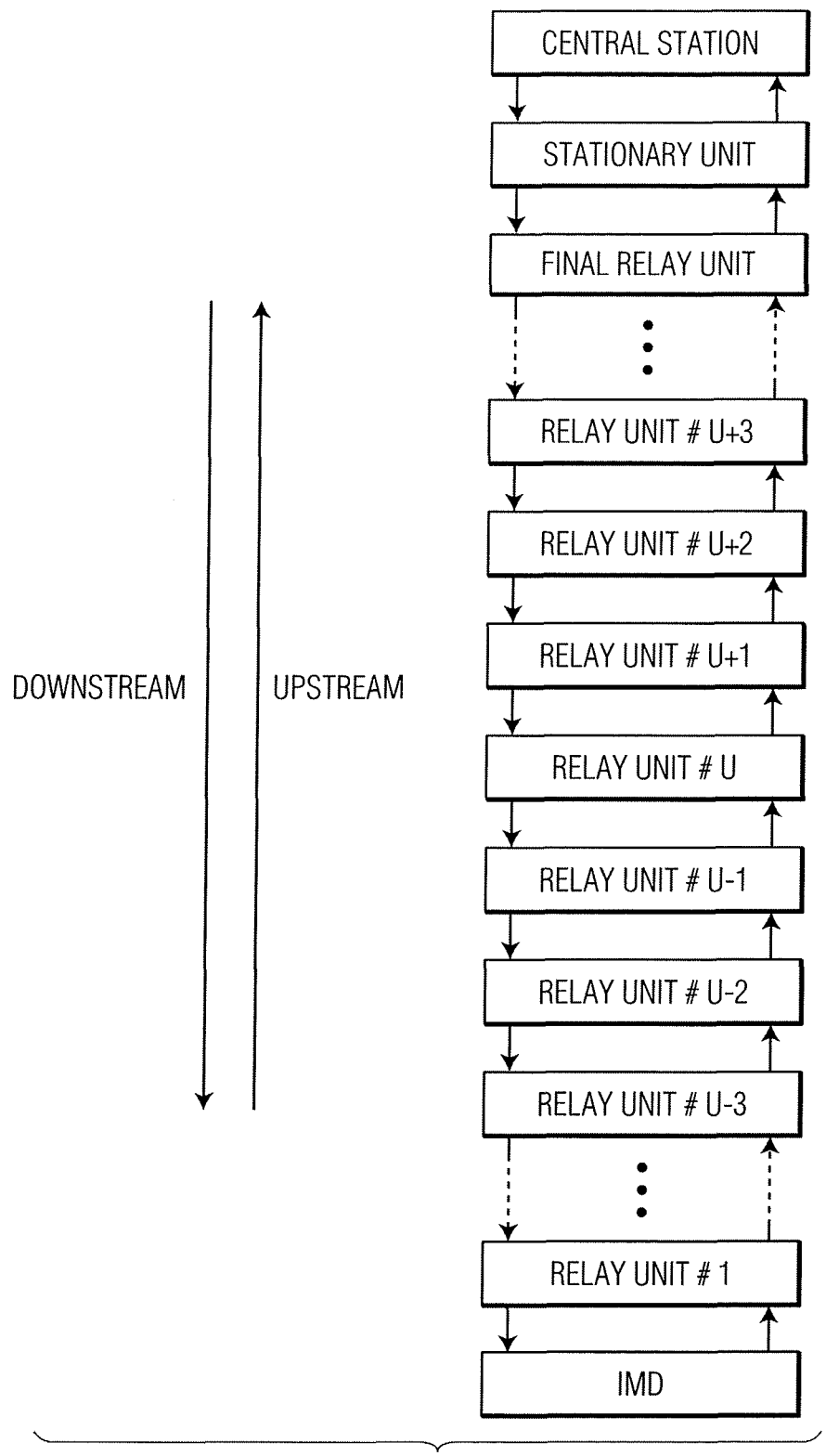
FIG. 18 is a block diagram showing the interrelationship among and nomenclature for describing an implantable medical device, a multiplicity of communication relay units including a final/most upstream communication relay unit, a stationary unit and a central station which comprise a system which may communicate with and remotely control and IMD.

FIG. 18 shows an IMD which communicates with a central station. A series of relay units (from relay unit #1 to the final relay unit), each intended to be a mobile unit, extend from the IMD to the first stationary unit. In an actual setup, there may be many relay units, one relay unit or no relay units. Examples of relay units include CPDs, WDs and RFIDs. The final relay unit may communicate with a nearby SU, or may communicate directly with the CS.

The term "downstream" refers to the communication direction from the CS to the IMD; the term upstream" refers to the communication direction from the IMD to the CS.

As indicated in the figure, if a particular unit is designated as "relay unit U", then the next unit immediate upstream (i.e. without any intervening unit) is designated as "relay unit U+1". For example, if unit U is a WD, unit U+1 may be a CPD. The next upstream unit from relay unit U+1 is designated "relay unit U+2", and the next upstream unit from relay unit U+2 is designated "relay unit U+3".

The next unit immediate downstream from unit U (i.e. without any intervening unit) is designated as "relay unit U−1". For example, if unit U is a WD, unit U−1 may be a RFID, or the IMD itself. The next downstream unit from relay unit U−1 is "relay unit U−2", and the next unit downstream from relay unit U−2 is designated "relay unit U−3".

The term "adjacent" refers to two units which, using the nomenclature and architecture shown in FIG. 18, communicate without an intervening unit. Thus units U+2 and unit U are each adjacent to unit U+1. The term "neighbor" refers to an adjacent communications unit; Thus units U+2 and unit U are each neighbors of unit U+1. Though the usual situation will be that each unit communicates with its two adjacent neighbors, there may be situations where one unit finds it easier to communicate with a non-adjacent one than with an adjacent one. For example, in a system in which the mobile units are an IMD, a WD (relay unit #1) and a CPD (relay unit #2), an IMD owner may be carrying his CPD in a pocket of his clothing, but may have left the WD in a not nearby location. In this case, the IMD may have easier/better communications with the CPD than the IMD, and the communications path between the IMD and the CS could then be IMD←→CPD←→CS, rather than IMD←→WD-←→CPD←→CS.

Motion detecting capability, "MDC" refers to a unit having the ability to detect its own motion. Such ability could:
 A) result from either of the types of motion detecting apparatus that pacemakers and ICDs use, i.e. accelerometers or piezoelectric crystal detectors, which hereinbelow are referred to as "MD/A/P";
 B) result from a GPS-based system; or
 C) be derived from signal strength information (i.e. If there is a signal source of constant intensity at one location, and signal detection apparatus at another location, then the detection of a signal with gradually declining intensity over a period of time, suggests that the detection apparatus and the source are moving away from each other).

The "activity frontier" refers to the boundary between (i) one or more adjacent moving units and (ii) a non-moving unit. An "upstream activity frontier" is the boundary between (i) the most upstream moving unit of a group of adjacent moving units and (ii) the next upstream neighbor, which is non-moving. A "downstream activity frontier" is the boundary between (i) the most downstream moving unit of a group of adjacent moving units and (ii) the next downstream neighbor, which is non-moving. Thus, if the IMD owner is moving and is wearing a WD (and hence the WD is moving), and the IMD owner has a CPD which is nearby but is stationary, the upstream activity frontier is defined as the WD. If the IMD owner is at home with his CPD and neither are moving, but the IMD owner left the WD in a moving vehicle, then the WD is both the upstream and the downstream activity frontier.

If none of the mobile elements are moving, the situation is referred to as a "quiescent state". If there is incomplete information about whether all elements are stationary, then an adverb may be added to define the likelihood of a quiescent state, based on the number of non-moving elements, e.g. a "possibly quiescent state" if two mobile elements are quiescent, and a probably quiescent state if three mobile elements are quiescent.

General Principles:

(1) Use of Activity Information:

Using motion information can help to optimize communications between adjacent units and decrease battery drain. If communication between adjacent units was of good quality at time t, then
- a) it is likely to be of good quality at time t+x, if during the interval between t and t+x the distance between adjacent units did not increase, which is likely to be the case if neither of the two adjacent units moved during the time interval; and
- b) it is less likely to be of good quality at time t+x, if during the interval between t and t+x the distance between adjacent units increased, a condition whose likelihood is increased if at least one of the two units moved.

(2) Techniques and Rationale for Locally Increasing Communication Efforts:

In order to compensate for the motion of either of a pair of communicating units, any one or more of a number of actions may be taken to "increase the assiduousness of communication" between the units of this pair, including:
- a) increase the power output of the upstream member of the pair on the channel for downstream communications with its neighbor;
- b) increase the power output of the downstream member of the pair on the channel for upstream communications with its neighbor;
- c) increase the sensitivity of the upstream member to signals from downstream;
- d) increase the sensitivity of the downstream member to signals from upstream;
- e) increase the frequency of handshake signals between the two communicating elements, e.g., increase the repetition rate of S1s for the upstream element and/or increase the ratio of number of S2s to number of S1s for the downstream element; and/or
- f) if necessary, i.e. if during the period of motion signal quality is decreasing, change the communications channel or mode or route for communications between the upstream and the downstream elements.

Other communication optimization approaches will be obvious to those skilled in the art.

(3) Two Adjacent Units with Different Activity Profiles: The Activity Frontier:

If one member of a pair of adjacent units is moving and the other is not, then the link between these two is a preferred locus for an increase in the assiduousness of communications, by using one or more of the approaches listed in (2) hereinabove. The rationale for the increase in assiduousness is that it is possible that the detected movement may result in an increasing degree of separation between the moving and the adjacent non-moving unit. For example, if the IMD owner is wearing a WD which has motion detecting capability, (MDC), and the IMD owner is moving, but the CPD is not moving, then the WD/CPD junction is a more vulnerable communications link, than it would be if neither device was in motion. The WD would be considered the upstream activity frontier, and efforts to locally increase the assiduousness of communications would include:
- a) increasing the power output of the CPD on the channel for communications with the WD;
- b) increasing the power output of the WD on the channel for communications with the CPD;
- c) increasing the sensitivity of the CPD to signals from the WD;
- d) increasing the sensitivity of the WD to signals from CPD;
- e) increasing the frequency of S1s from the CPD and/or increasing the ratio of number of S2s to number of S1s at the WD; and/or
- f) if necessary, i.e. if during the period of motion signal quality is decreasing, changing the communications channel or mode or route for communications between the CPD and the WD.

It would also be possible to forgo doing all of a)-f) in the event of detected motion.

If the IMD owner is moving, then the upstream activity frontier defines the most upstream point of repeater units that are carried by or moving with the IMD owner. Since the downstream activity frontier is defined as the most downstream moving unit among a number of adjacent moving units, in the case of a moving IMD owner, the downstream activity frontier is the IMD. Since the IMD has no downstream neighbor, in cases where the IMD owner is moving, no adjustments need be made at the downstream activity frontier. However, if a repeater unit (e.g. the CPD) is accidentally left on a moving vehicle, and if the next downstream unit (i.e. the WD) is not moving, then a downstream activity frontier exists (in this case at the CPD), and an increase in communications assiduousness at the downstream activity frontier (i.e. for communications between the CPD and the WD) is called for.

(4) Two Adjacent Units, Both of which are Moving:

If both members of a pair of adjacent units are moving, then there is a substantial possibility that the two units are moving together (e.g. the IMD owner is wearing a wrist device, and begins to walk). Additional information that would support the two moving together includes:
- A) The moment that movement begins for one member of the pair is substantially the same as the moment that movement begins for the other member of the pair;
- B) If movement temporarily halts for one unit, it halts or is substantially reduced for the other, in a similar time frame; and it resumes for both in a substantially similar time frame;
- C) If a third communications unit, adjacent to one of the two units in the aforementioned pair has MDC, that third unit's MDC also detects motion in a similar time frame to that for the aforementioned pair of units;
- D) If the two members of the pair both have GPS capability, then movement of the two units substantially together could be confirmed by comparing GPS information from each; and
- E) If a signal of a given power is transmitted from one unit of an adjacent pair and is received with signal strength which remains constant over a period of time at the other unit of the pair.

(5) No Increase in Communication Efforts at Junction of Two Moving Units:

If two adjacent units are both moving, then assuming [as per (4) above] that they are moving together leads to the conclusion that the measures to increase the assiduousness of communication between them [as listed in 2) above] should not be undertaken.

(6) Two Adjacent, Both of which are not Moving: The Quiescent State:

If both members of a pair of adjacent units are not moving, then there is a substantial possibility that:
  A) additional mobile units, if any, are not moving; and
  B) the IMD owner is not moving.

Additional information that would support a "quiescent state," i.e. a state in which all mobile units are not moving is as follows:
  A) If there is a third communications unit, adjacent to one of the two units in the aforementioned pair, and that third unit has MDC, and that third unit's MDC also does not detect motion, then such non-detection of motion increases the likelihood of a quiescent state.
  B) If either of the two members of the pair (or both) have GPS capability, then GPS information may be used to further define the likelihood of a quiescent state. For example:
    i) If a stationary state is reported from a GPS in one member of the pair of units, and a stationary state is reported from the other member of the pair of units by MD/A/P, a possibly quiescent state may be concluded.
    ii) If a stationary state is reported from GPS in each member of adjacent units, then even if neither of these units have MD/A/P, the conclusion of a possibly quiescent state is warranted;
    iii) Clearly, the certainty of determination of a quiescent state increases with increasing numbers of detectors reporting no motion. Thus if there are reports of no motion from each of three detectors among a pair of units (e.g. from a MD/A/P in one unit and a GPS in each of the two units, or from a GPS in one unit and MD/A/P in each of the two units), then the likelihood of a quiescent state is greater than if there were two such reports. If both units have MD/A/P and both units have GPS, and all four reports indicate no motion, there is even greater certainty about the conclusion of the existence of a quiescent state.

Note is made of the facts that the primary data from GPS is a determination of the position of a unit, and that the primary data from MD/A/P is the detection of an acceleration. Therefore:
  a) Velocity information would have to be derived information for a GPS-based determination—the calculation of which will be obvious to those skilled in the art; and
  b) In principle, one may have a state of substantially constant velocity which would not cause the an accelerometer or piezoelectric motion detecting apparatus to report a state of activity. (In fact, perfectly constant linear motion should cause no activity signal from either an accelerometer or piezoelectric device, and small deviations from perfectly linear motion may fall below the threshold for activity detection.)

In short, each of MD/A/P and GPS look at motion differently, and their respective analyses may complement each other.
  C) If a signal of a given power is transmitted from one unit of an adjacent pair and is received with signal strength which remains constant over a period of time at the other unit of the pair, this supports non-motion. Although a conclusion of non-motion based on signal strength could, under certain circumstances be inaccurate (e.g. if one unit is executing angular motion with respect to the other), the monitoring of signal strength has the advantage of leading to the suggestion of some clearly remedial actions such as increasing either the power output at the source or the sensitivity at the receiving end. Other remedial actions will be obvious to those skilled in the art.

Each of three modalities, (i) signal quality information, (ii) GPS information, and (iii) MD/A/P information may be used alone or in combination to assess whether a state of motion does or does not exist. Furthermore, one or more motion detecting modalities situated on two or more communicating units may be used to determine whether the motion is local (e.g. the case of a lost/misplaced unit [see hereinbelow]), or global (e.g. IMD and WD and CPD moving together).

(7) Techniques and Rationale for Locally Decreasing Communication Efforts:

If a determination is made that two or more communicating units are not moving (or are moving in a manner such that their relative positions are fixed), then it may be advantageous to take measures to decrease the assiduousness of local communication efforts in anticipation of a stable spatial relationship between each pair of non-moving units. The decrease may save battery power, and decrease sensitivity to outside interference. Examples of specific actions to accomplish this task include:
  a) decreasing the power output of the upstream member of the pair on the channel for downstream communications with its neighbor;
  b) decreasing the power output of the downstream member of the pair on the channel for upstream communications with its neighbor;
  c) decreasing the sensitivity of the upstream member to signals from downstream;
  d) decreasing the sensitivity of the downstream member to signals from upstream; and/or
  e) decreasing the frequency of handshake signals between the two communicating elements, e.g., decreasing the repetition rate of S1s for the upstream element and/or decreasing the ratio of number of S2s to number of S1s for the downstream element.

Other such approaches will be obvious to those skilled in the art.

(8) Techniques for Communications Management when not all Units have MD/A/P:

Approaches include:
  a) looking further upstream, downstream, or in both directions:
    i) If the activity status of unit U is unknown, then for upstream communications, the activity status of unit U+1 gives suggestive (though not unequivocal) information about the motion status of unit U; Further corroborating information may be sought by examining the state of motion of (I) unit U+2, (II) unit U−1, or (III) both units U+2 and U−1. Thus if the activity status of unit U is unknown but the activity status of both of units U−1 and U+1 are identical, then it is even more likely that the activity status of unit U is the same as that of unit U+1 (and of unit U−1), than would be the case if only the activity status of U+1 was available. Similarly, if the activity status of unit U is unknown, then for downstream communications, the activity status of unit U−1 gives suggestive (though not unequivocal) information about the motion status of unit U; Further corroborating information may be sought by examining the state of motion of (I) unit U−2, (II) unit U+1, or (III) both units U−2 and U+1.

ii) If the activity status of an upstream units is unknown, then looking downstream may provide useful information about the upstream state of motion. For example, if the activity status of unit U is unknown, and the activity status of unit U+1 is unknown, then for upstream communications, the activity status of unit U−1 may be useful. Similarly, if the activity status of unit U is unknown, and the activity status of unit U−1 is unknown, then for downstream communications, the activity status of unit U+1 may be useful.

iii) If necessary looking even further upstream or downstream may be useful.

For example, if the activity status of unit U is unknown, and the activity status of unit U+1 is unknown, then for upstream communications, the activity status of unit U+2 may give suggestive (though not unequivocal) information about the motion status of unit U; similarly, if necessary, looking two or more units downstream may prove useful for downstream communications;

b) looking at GPS data and attempting to make a motion determination based on that information;
   c) looking at signal strength and attempting to make a motion determination based on that information; and/or
   d) combinations of a)-c)

(9) Lost or Misplaced Unit:

If a communications unit has a motion state which is the opposite of both of its neighbors, it may be lost or misplaced. There are two possible families of motion states that define this condition:

a) If the activity sensor of a communications unit shows motion while the activity sensors of each of the neighboring communication units do not, then the unit associated with the sensor indicating movement may be lost or misplaced. For example: If the WD activity sensor shows that the WD is moving, while (i) the IMD sensor shows no motion, and (ii) the CPD sensor shows no motion, then the WD may have been left off of the IMD owner in a location where it is subject to movement (e.g. in someone else's automobile).
   b) If the activity sensor of a communications unit shows no motion while the activity sensors of each of the neighboring communication units show motion, then the unit associated with the sensor indicating no motion may be lost or misplaced. For example, the IMD owner may have left the home, taking along his CPD but accidentally leaving behind his WD.

Remedies for a lost/misplaced communications unit include:

a) notify the IMD owner (e.g. by sending a message via the CPD);
   b) notify the CS; and/or
   c) the two communications units which are adjacent to the lost/misplaced unit (e.g. the IMD and the CPD, in the example hereinabove) communicate with each other until the lost/misplaced unit is returned to the vicinity of its neighbors [see (10) hereinbelow];

(10) Bypass of a Communications Unit Possible:

Under certain circumstances, it may be advantageous to have one communications unit bypass its neighbor and communicate directly with a unit which is further upstream or downstream. Using the nomenclature defined hereinabove, this would entail a circumstance where, for example, unit U communicates directly with unit U+2 (or U−2) or directly with unit U+3 (or U−3). In the example, the bypass of unit U+1 (or U−1) could occur because U+1 (or U−1):

a) is lost or misplaced;
   b) has a failing or failed battery; or
   c) is geometrically situated such that a communication path which bypasses U+1 (or U−1) is more efficient.

Figure 19A:
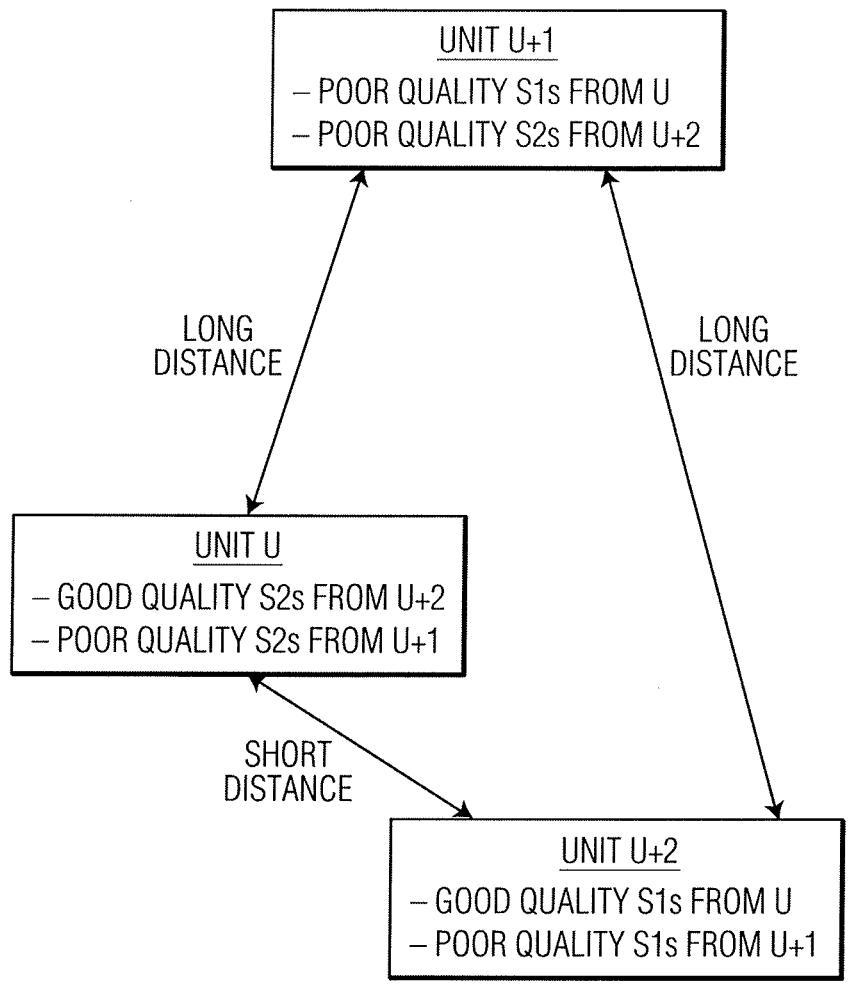
FIG. 19A shows one possible geometric relationship between three adjacent communication units that favors bypassing the middle one of the three units.

An example of c) would be, as shown in FIG. 19A, if the distance between unit U+1 and either of its neighbors was large, while the distance between unit U and unit U+2 was small.

Methods of determining that it would be desirable to bypass a unit include:

a) the pattern of motion described hereinabove in paragraph (9) [Lost or Misplaced Unit], i.e. a sequence of three adjacent communication units whose motion is either (i) positive, negative, positive, or (ii) negative, positive, negative;
   b) the detection of a low battery voltage in a unit;
   c) detection of geometric relationship between U, U+1 and U+2 which was given as an example immediately hereinabove by either (i) GPS, and/or (ii) signal strength. In the case of signal strength, the expected pattern would be:
      I) good signal strength for communications between units U and U+2; and
      II) less than good signal strength for at least one of:
   communications between units U and U+1, and
   communications between units U+1 and U+2.

FIG. 19A shows an example of locations of units U, U+1 and U+2 in which illustrates the above, in which the bypass of unit U and the direct communication of units U and U+2 would be advantageous. The detection of the situation in which bypass would be favorable could be because:

a) at unit U+2: there are poor quality S1s from unit U+1, but
      i) at unit U+2: there are good quality S1s from unit U, and
      ii) at unit U: there are good quality S2s from unit U+2;
   b) at unit U: there are poor quality S2s from unit U+1, but
      i) at unit U+2: there are good quality S1s from unit U, and
      ii) at unit U: there are good quality S2s from unit U+2;
   c) at unit U+1: there are poor quality S1s from unit U, but
      i) at unit U+2: there are good quality S1s from unit U, and
      ii) at unit U: there are good quality S2s from unit U+2; and/or
   d) at unit U+1: there are poor quality S2s from unit U+2, and
      i) at unit U+2: there are good quality S1s from unit U, and
      ii) at unit U: there are good quality S2s from unit U+2.

(11) Local vs. Central vs. Semi-Central Communication Control:

FIG. 19A, and many of the algorithms illustrated hereinabove and hereinbelow illustrate local control, i.e. a particular communications unit uses information from itself and/or from an adjacent unit to adjust communications (e.g. poor quality of a received S1 at unit U results in an increase in the sensitivity of unit U to incoming S1s).

However, it would be possible to designate one communications unit as a central control unit (which may or may not be the central station), which receives one or more of (a) signal quality data, (b) GPS data, (c) motion data, and (d) battery information from one or more communication units (from all units in a preferred embodiment of the invention), and uses some or all of that information to determine a set of optimum values of communication parameters (e.g. route, power output of each unit, sensitivity of each unit, etc) for the entire system. These optimum values may change from time to time (e.g. depending on the locations of the communicating units). Furthermore, the choice of which unit is to be the central control unit may change from time to time (e.g. an upstairs SU may be the appropriate choice when the IMD owner is on an upper floor of a multi-floor home, while a downstairs SU may be more appropriate once the IMD owner descends to one of the lower floors). The selection of which unit is to be the central communications may be fixed (e.g. always the central station), may involve a preset sequence ([i] central station if certain conditions obtain, if not, [ii] home SU, if not, [iii] office [SU]), or may involve a process whereby the choice is made at any moment based on current system conditions (e.g. [i] the unit which at any moment has the best communications with each of the other units in the system, or [ii] the unit which is most centrally located among the units, or [iii] considerations based on battery reserve, or [iv] other considerations, or [v] combinations of [i] to [iv]).

It would also be possible to designate each of two or more communication units as a semi-central control unit. For example, unit U might be the semi-central control unit for each of units U−1, U and U+1; while unit U+3 might be the semi-central control unit for each of units U+2, U+3 and U+4.

(12) Activity Signal Need not be all-or-None:

Implantable pacemakers and ICDs with activity responsive modes (e.g. VVIR, DDDR) generally have a graded response to activity, i.e. within certain limits, more activity results in greater upward adjustment of the pacing rate. The response to activity may be linear or non-linear, over a certain range of heart rates. An activity threshold may be set which determines the sensitivity of the detection apparatus to motion. This is the state of the art, and multiple preferred embodiments of the invention may incorporate some or all of these features. In the specification hereinbelow activity detection is frequently referred to as an all-or-none phenomenon, but approaches in which evaluate intensity of activity are possible.

For example: Certain patterns of low level motion may be part of an in-home routine that require only a small step-up, if any, in the assiduousness of communication, while higher level patterns of motion may suggest that the IMD owner is leaving the home, or is performing an unknown activity. The system may be programmed to recognize this distinction in advance, or may have learning programs, which, over a period of time, may learn to recognize the distinction. For example, if a low level of activity during the early morning and late evening hours consistently is not associated with a significant decrease in unit-to-unit signal amplitude, the system may learn to recognize that these events are related to getting dressed and undressed, brushing teeth, etc.

Other examples will be obvious to those skilled in the art.

(13) During the Unit-to Unit Exchange of Activity Information, Inter-Unit Communications are Assumed to be Intact.

In the event that they are not, multiple remedies are available, including those discussed hereinabove in conjunction with FIGS. 7-10 and 12-13.

(14) Actual CS-to-IMD Communications and IMD-to-CS Communications Use Communication Parameters Selected and Optimized During the Communication Optimization Routine.

The vast majority of the life of an IMD is likely not to require communication with a CS or MD. The communication optimization protocols described herein allow for frequent system/route/parameter optimization, so that if/when the moment arrives when there is need for a communication, the likelihood is very high that a high quality exchange of information between CS and IMD can occur immediately. (See further discussion hereinbelow regarding storage of optimization information, especially in conjunction with FIG. 29B.)

Ongoing optimization of the link between the IMD itself and the first repeater unit is a step that does consume some IMD battery energy. Ways to limit such consumption are:

a) If there is a high level of certainty that the first repeater unit will be in very close proximity to the IMD, then only very infrequent confirmation of the operability of the IMD to first repeater unit may be performed;

b) The type of asymmetric handshaking format between the first repeater unit and the IMD with a ratio of many first repeater S1s to few IMD S2s, would allow the IMD to not transmit unless it failed to receive timely S1s.

Specific (Simple) Architectures

In FIGS. 19B-27C activity detection is assumed to be primarily accelerometer or piezoelectric crystal-based. The use of GPS and/or signal strength data is also possible, and appear frequently in the figures as approaches to augmenting the accelerometer/crystal data. Each of these motion detecting techniques may be the sole motion detecting modality, or may be part of a multi-modal approach. Many other uni-modal and multi-modal approaches will be obvious to those skilled in the art, but will be based on the principles herein.

Figure 19B:
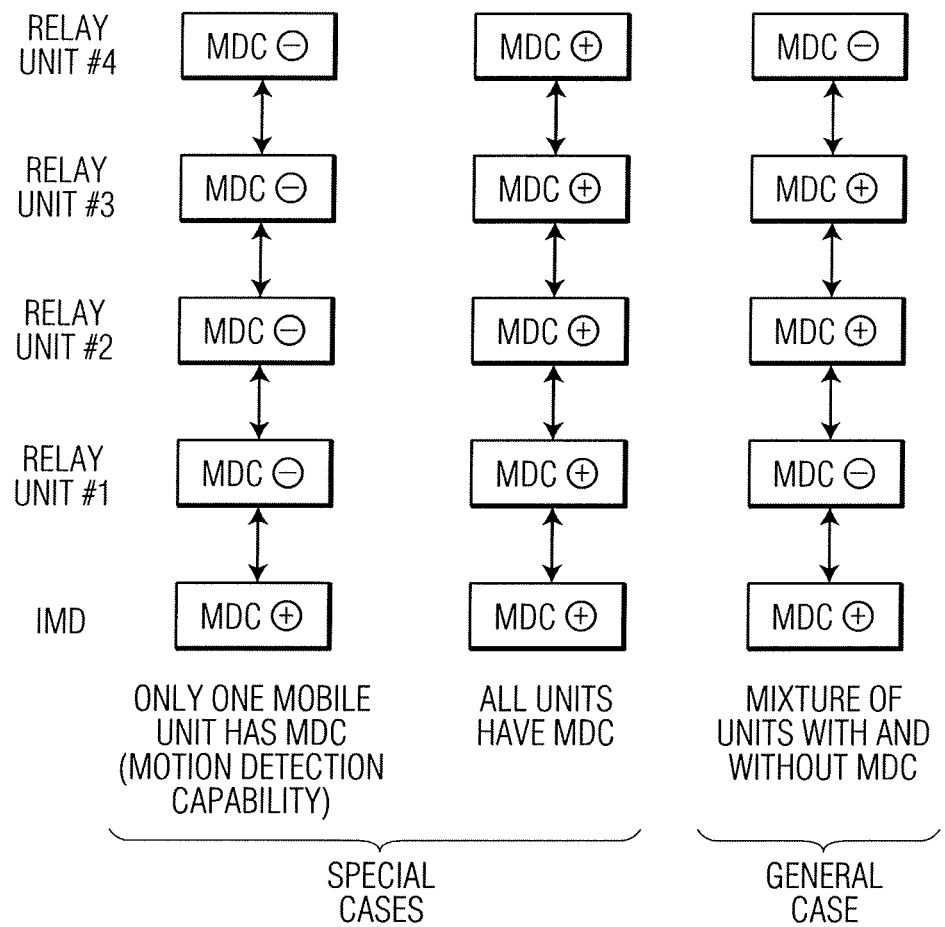
FIG. 19B shows three block diagrams of exemplary systems comprising an IMD and multiple communication relay units: a) one in which only the IMD has motion detection capability, b) one in which the IMD and all communication relay units have motion detection capability, and c) one in which some but not all of the mobile units of the system have motion detection capability.

In a system with multiple communicating units, at least one of which has motion detection capability, one, some, or all of the units may have motion detecting capability. This section considers two specific simple architectures: (a) that in which only one mobile communications unit has MDC; and (b) that in which all mobile communication units have MDC. The general case—in which any unit may or may not have MDC—is discussed in the next section. FIG. 19B schematically depicts these three cases. The left-most column depicts a system in which only the IMD has MDC.

Referring to the case of the left-most column in FIG. 19B: Since the detection of activity by the IMD does not give enough information to determine whether only the IMD-owner is moving, or whether more upstream units such as the CPD are also moving, a simple approach is to increase the assiduousness of communications between all mobile units upon the detection of motion by the IMD. For example, any one or more of the techniques a)-f) listed in (2) above could accomplish this task. Another approach would be: Upon detection of motion by the IMD, use GPS and/or signal strength data to attempt to learn more about the location of the upstream activity frontier. If the most upstream moving unit is thereby determined, then the increase in communications assiduousness can be restricted to the pair of units that are (i) the most upstream moving unit and (ii) the next most upstream unit (which will be stationary).

Architecture in which all Movable Units have MDC

Figure 20:
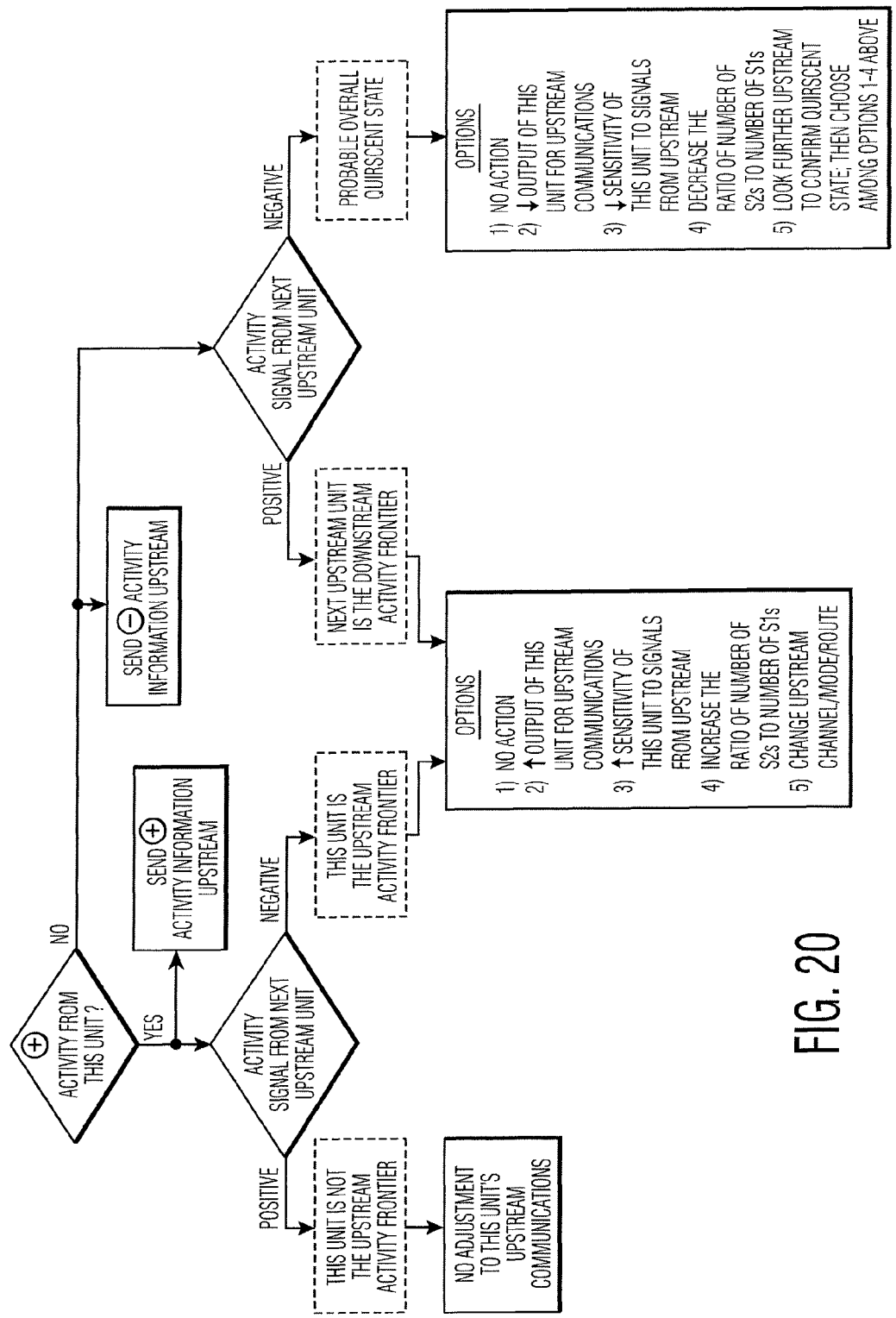
FIG. 20 is a flow chart illustrating the operation of an implantable medical device in a communications system in which all mobile units have motion detection capability.
Figure 21:
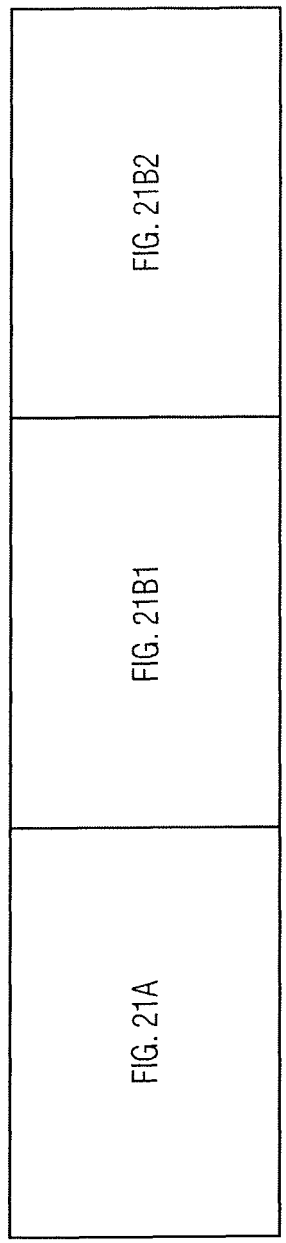
FIG. 21 is a legend showing the interrelationship of FIGS. 21A and 21B, which comprise a flow chart illustrating the operation of a repeater unit in a communications system in which all mobile units have motion detection capability.
Figure 21A:
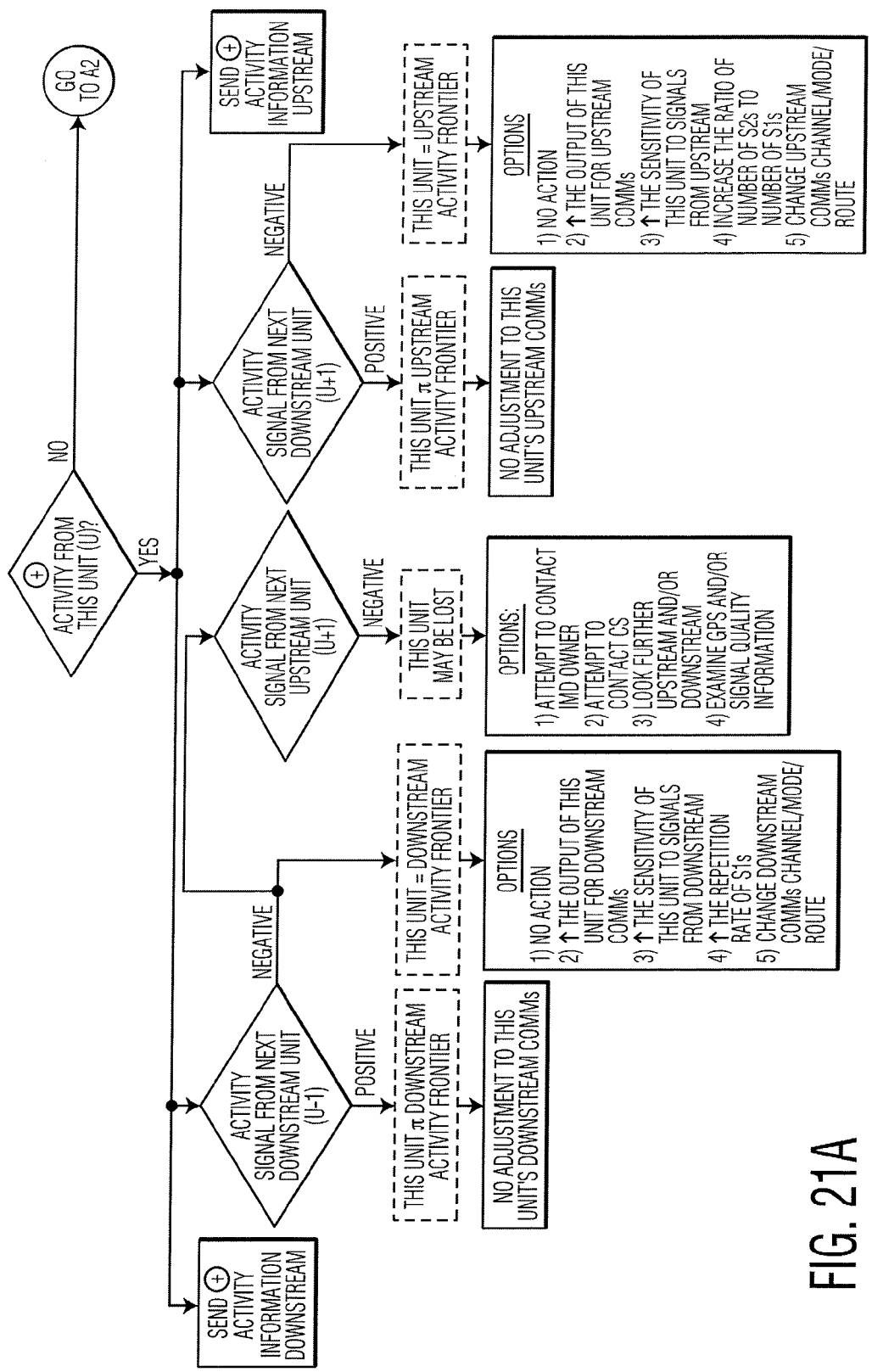
Figure 22A:
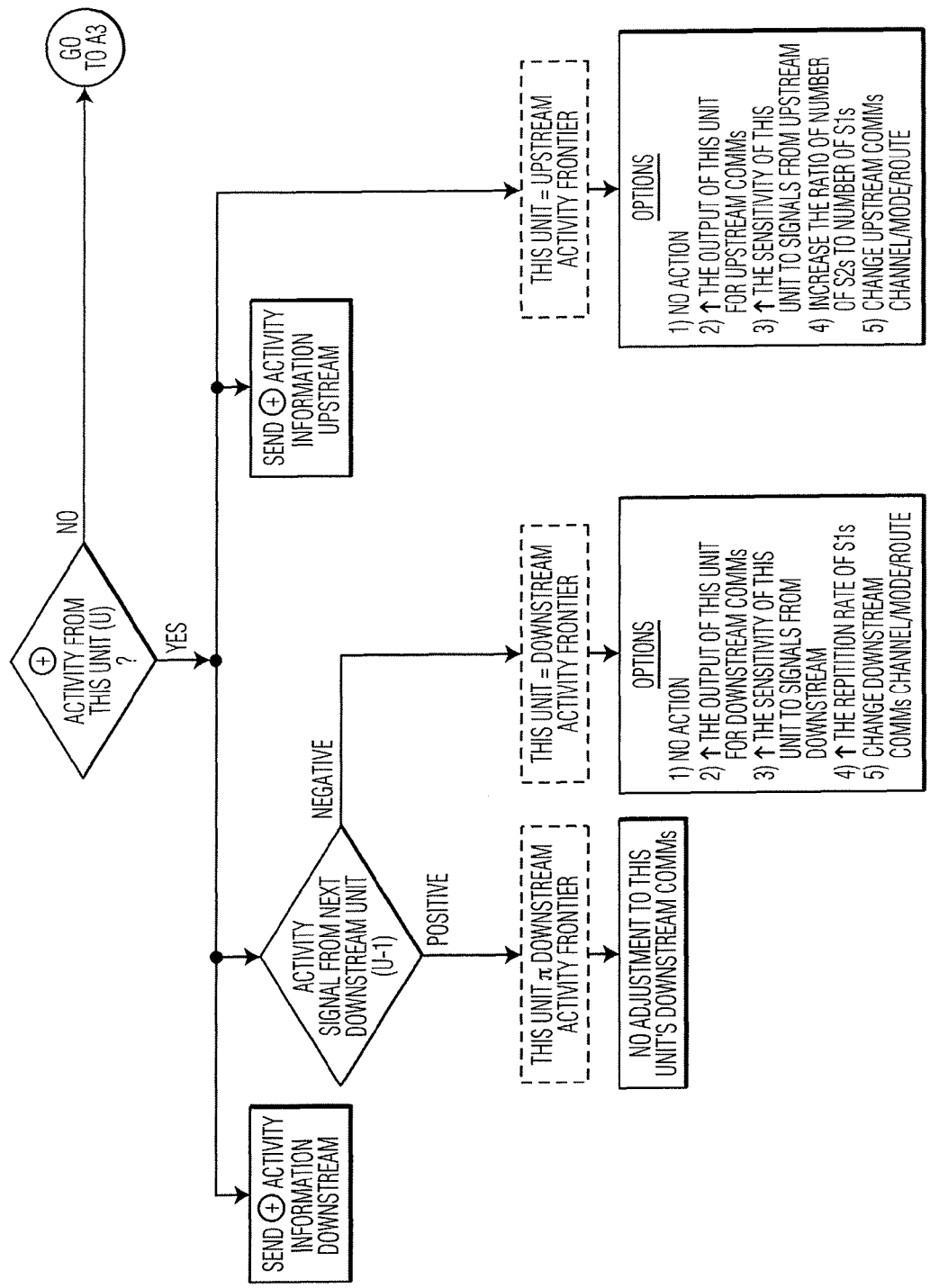
FIG. 22 is a legend showing the interrelationship of FIGS. 22A and 22B, which comprise a flow chart illustrating the operation of the most upstream repeater unit in a communications system in which all mobile units have motion detection capability.
Figure 22B:
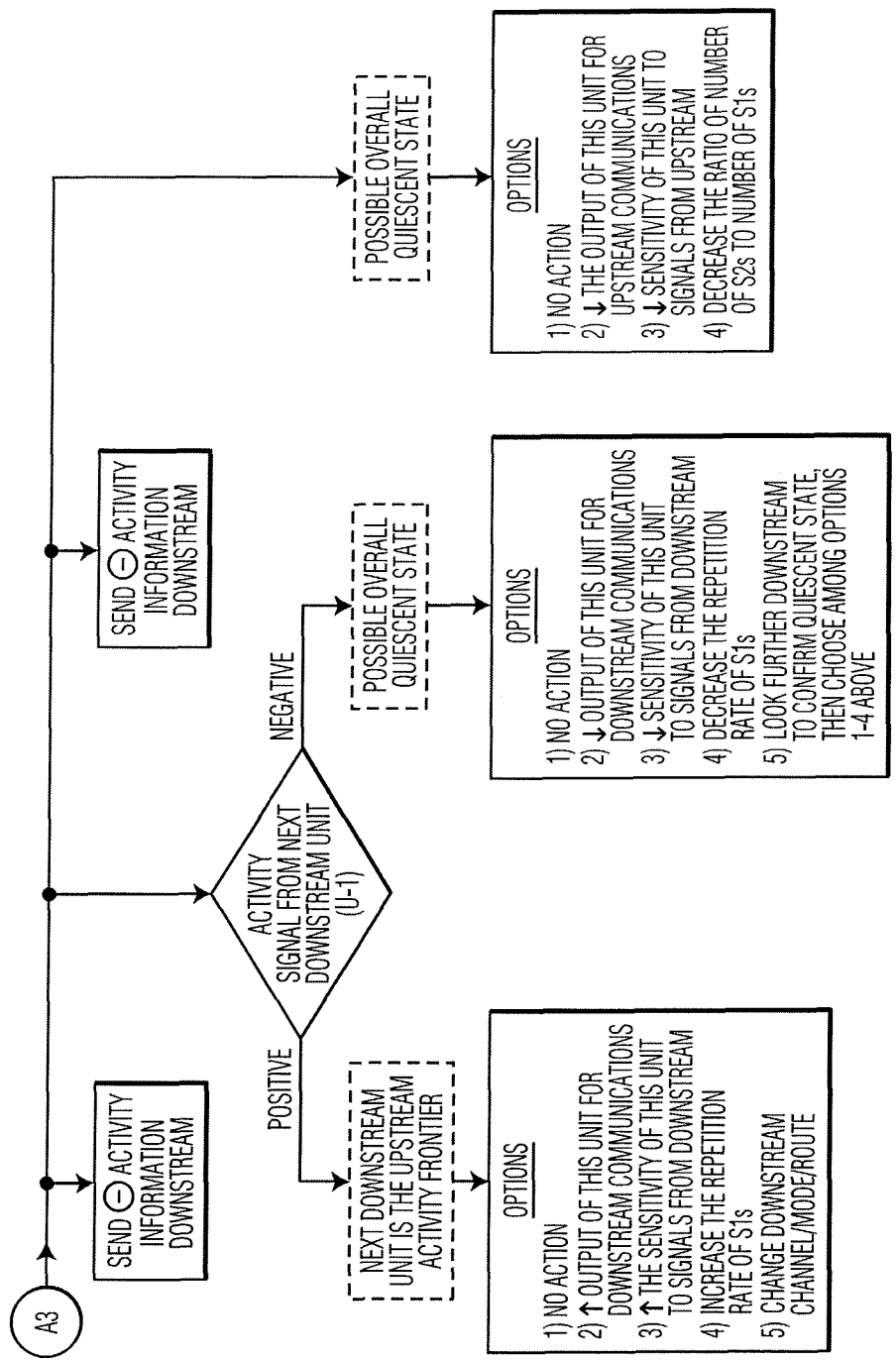
Figure 23:
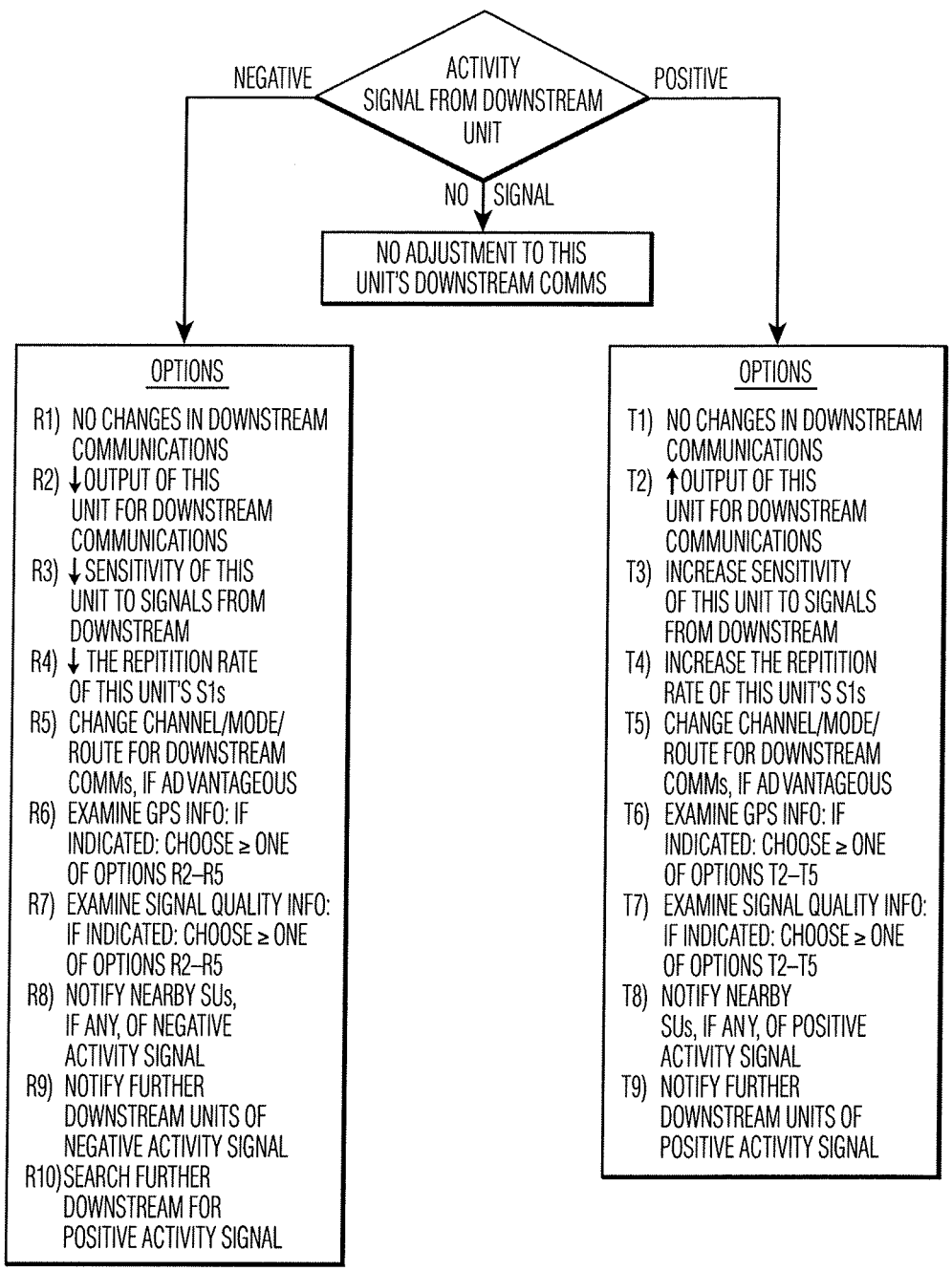
FIG. 23 is a flow chart illustrating the operation of a stationary communications unit, in a system in which an implantable medical device may communicate with a remote station.

FIGS. 20-22 show an example of a system in which all movable communication units have MDC; FIG. 20 shows the IMD, FIG. 21 shows a repeater unit and FIG. 22 shows the "final" repeater unit, i.e. the one which communicates with a stationary unit (which may itself be a repeater/relay unit or may be the central station). FIG. 23 shows a stationary unit which communicates with any of the units shown in FIGS. 20-22.

In FIG. 20 and the figures which follow, boxes defined by broken lines indicate an inference drawn based on obtained activity information; The broken-line-boxes are intended to indicated the rationale for the operations which follow them.

The essential feature of FIG. 20 is the determination of which of four activity states the system (comprising the IMD and the next upstream communications unit) is in, v.i.z.:

State #1: IMD active, and next upstream unit active
[Conclusion: The IMD is not the upstream activity frontier, in which case communications are left unaltered, as per (4) and (5) among the General Principles above];

State #2: IMD active, next upstream unit inactive
[Conclusion: The IMD is the upstream activity frontier, in which case downstream to upstream communication efforts from the IMD to the upstream repeater may be increased, as per (2) and (3) among the General Principles above];

State #3: IMD inactive, next upstream unit active
[Conclusion: The upstream unit is the downstream activity frontier, in which case communications efforts from the IMD to the upstream repeater may be increased, as per (2) and (3) among the General Principles above];

State #4: IMD inactive, next upstream unit inactive [Conclusion: Probable quiescent state, in which case communications efforts from the IMD to the upstream repeater may be decreased, as per (6) and (7) among the General Principles above];

The activity state of the IMD is signaled upstream. Embodiments of the invention with a greater or lesser number of options for each contingency are possible.

FIG. 21, shows the repeater unit algorithm for a system in which all units have MDC. Since the repeater unit will have both a downstream and an upstream neighbor, eight States are shown, (i) four for the repeater and its upstream neighbor—which are essentially identical to the four states hereinabove for the IMD and its upstream neighbor; and (ii) four for the repeater and its downstream neighbor—which are also essentially identical to the four states hereinabove for the IMD and its upstream neighbor.

In addition to the features which parallel those of FIG. 20, FIG. 21 shows the following features:

If the unit activity status differs from each of its neighbors, then there is a possibility that the unit is lost or misplaced—as per (9) among the General Principles above—and four basic remedial actions are indicated in the figure;

If the activity status of three consecutive units is negative—i.e. all three are not moving, then the level of certainty of a quiescent state [designated as "probable"] is greater than the level of certainty if only two consecutive units are non-moving [in which case the designation is "possible"]. The distinction between "possible" and "probable" may be used for decision making in terms of (i) whether to decrease the assiduousness of communication between the involved units, and (ii) if there is to be such a decrease, the extent of the decrease.

FIG. 22 shows an operating algorithm for a "final repeater unit," i.e. a unit whose downstream neighbor is either the IMD or another repeater unit, and whose upstream neighbor is a stationary unit. This figure is essentially a simplified version of FIG. 21 in that:

a) It shows the same four States and possible actions for communicating with its downstream neighbor;

b) It shows two states and possible actions for communicating with the SU (only two states [v.i.z. (i) final repeater moving, and (ii) final repeater not moving], since the SU by definition cannot be in motion); and c) Since there is no opportunity to compare three consecutive moving units, the additional features of the general repeater [(i) lost/misplaced detection, and (ii) assessment of level of certainty of quiescent state] are not present.

Architecture for a General System

FIG. 23 shows an operating algorithm for a stationary unit, defined as the communications unit which communicates with the most upstream of the mobile repeater units (or, if there are no mobile repeater units, with the IMD itself). In a system in which all downstream units have MDC (e.g. as shown in FIGS. 20-22), the SU would receive either a positive activity signal or a negative activity signal from the next downstream unit. In the case of a positive activity signal, by definition, the upstream activity frontier must be the next downstream unit (since, by definition, the SU is not moving), and therefore the listed option T1-T9 address this circumstance. Options T1-T5 are the same as those shown in FIGS. 21 and 22 for a non moving upstream unit and an adjacent moving downstream unit. Options T6 and T7 allow for an examination of other determinants of unit motion (i.e. GPS or signal strength) before selecting among T2-T5; The examination of GPS and signal strength could be similarly incorporated into the option list of any of the algorithms hereinabove and hereinbelow. T8 is a lateral notification (from one SU to one or more other SUs): It may be used in a structure with multiple SUs (e.g. the upper floor SU telling a lower floor SU that the IMD owner is moving about, perhaps resulting, for example, in an increase in assiduousness of communication by the lower floor SU). T9 allows for the notification of any downstream units which may not have received the positive activity signal from the unit immediately downstream from the SU (either because [i] the algorithm may have called for repeater units to notify only the next downstream unit; and/or [ii] because the likely non-battery dependence of the SU allows for more generous use of power for transmission purposes).

In the case of a negative activity signal received from the downstream neighbor, a possibly quiescent state (of motion) exists, and the listed options R1-R10 address this circumstance. Options R1-R4 and R10 are the same as those shown in FIGS. 21 and 22 for a non moving upstream unit and an adjacent non-moving downstream unit. Option R5 allows for switching to a lower priority or quality communication channel/mode/route, if desirable. Options R6 and R7 allow for an examination of other determinants of unit motion (i.e. GPS or signal strength) before selecting among R2-R5. The purpose of each of R8 and R9 has the same conceptual basis as that of each of T8 and T9 respectively.

One aspect of FIG. 23 which differs from that of FIGS. 20 to 22 is that the FIG. 23 algorithm can accommodate a downstream unit which does not have MDC. In such a circumstance, there is no activity signal from the communications unit which is immediately downstream, and there is therefore no adjustment to be made of the SU communications. Algorithms are possible which, in the event that the immediately downstream unit provides no activity signal, look further downstream for such a signal.

Figure 24A:
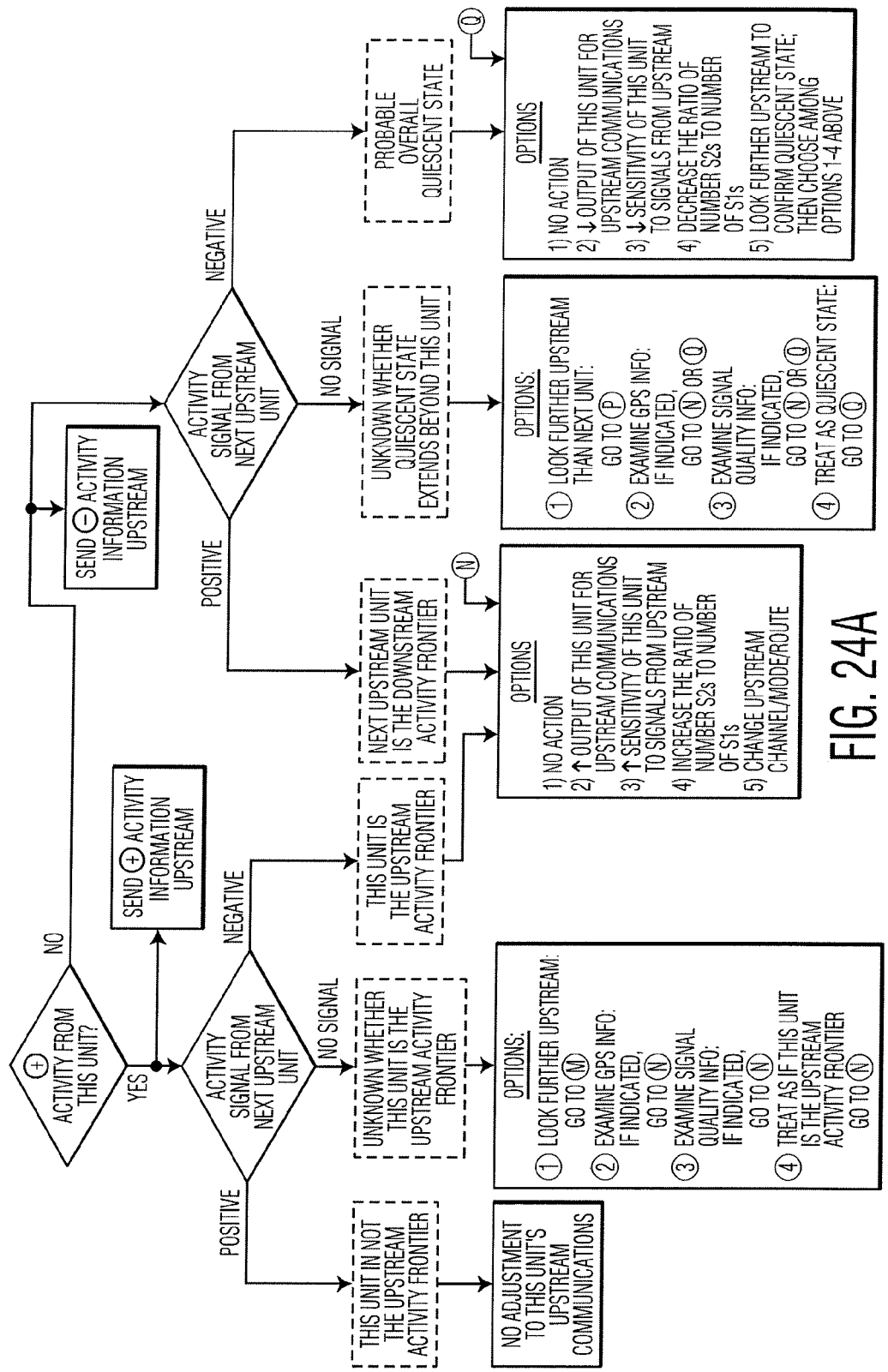
FIG. 24, is a legend showing the interrelationship of FIGS. 24A, 24B and 24C, which comprise a flow chart illustrating the operation of an implantable medical device which has motion detection capability, in a communications system in which any of the mobile units may or may not have motion detection capability.
Figure 24B:
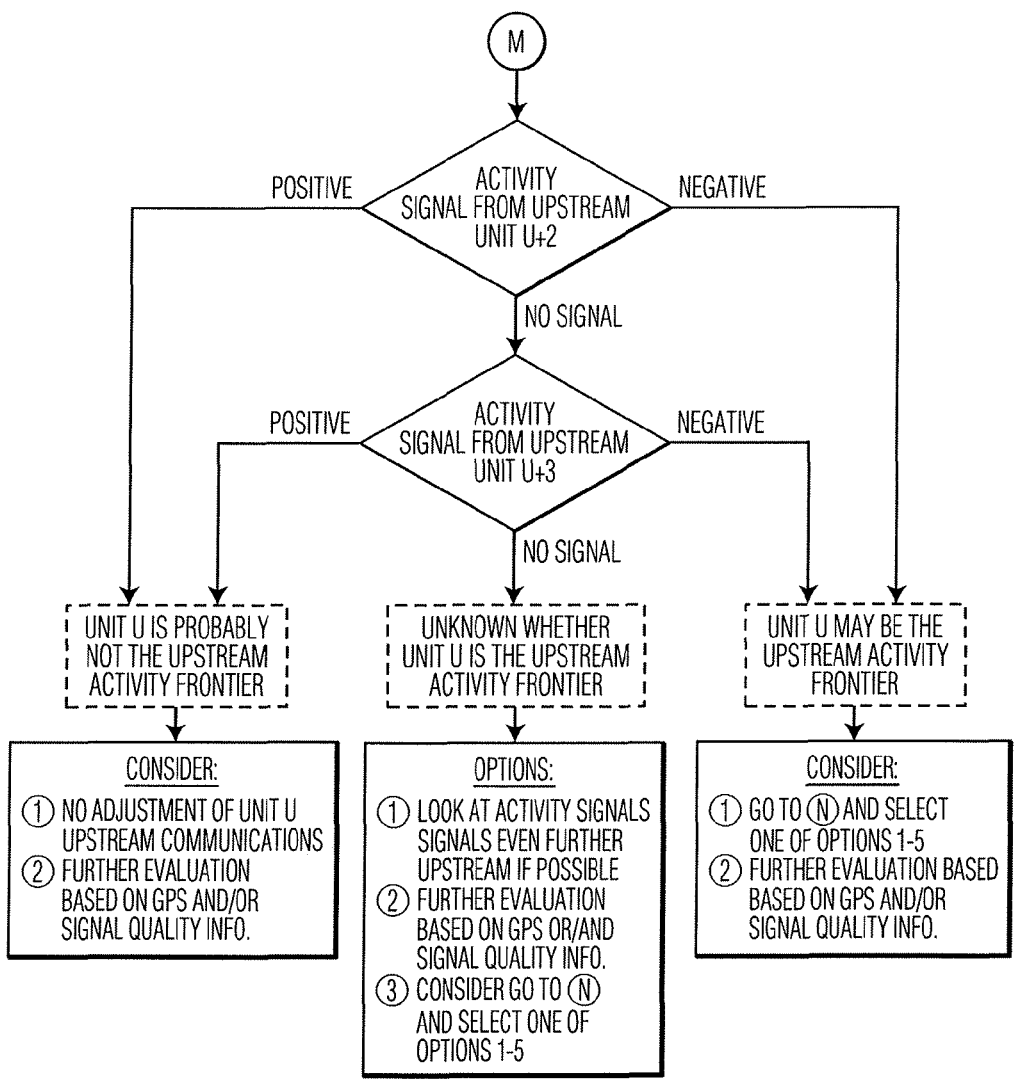
Figure 24C:
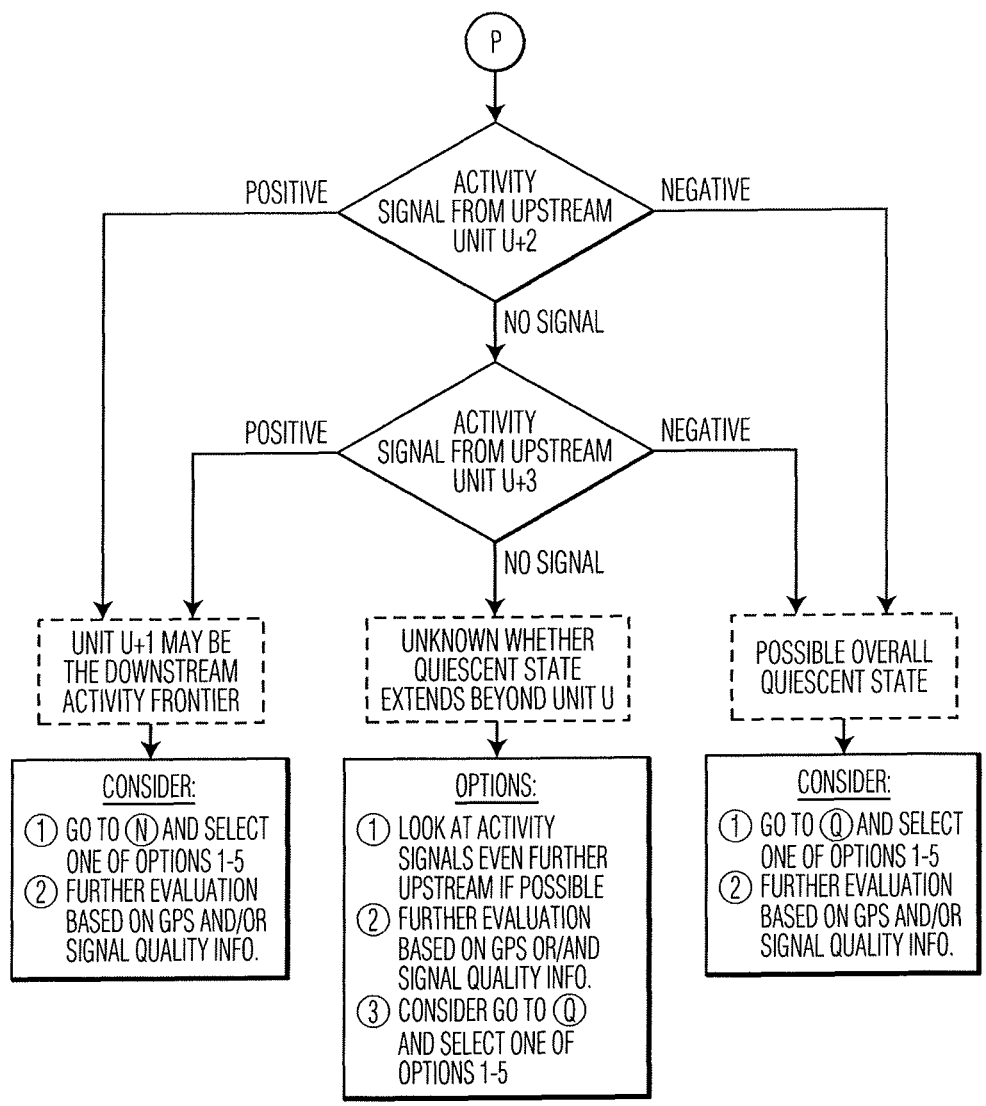
Figure 25:
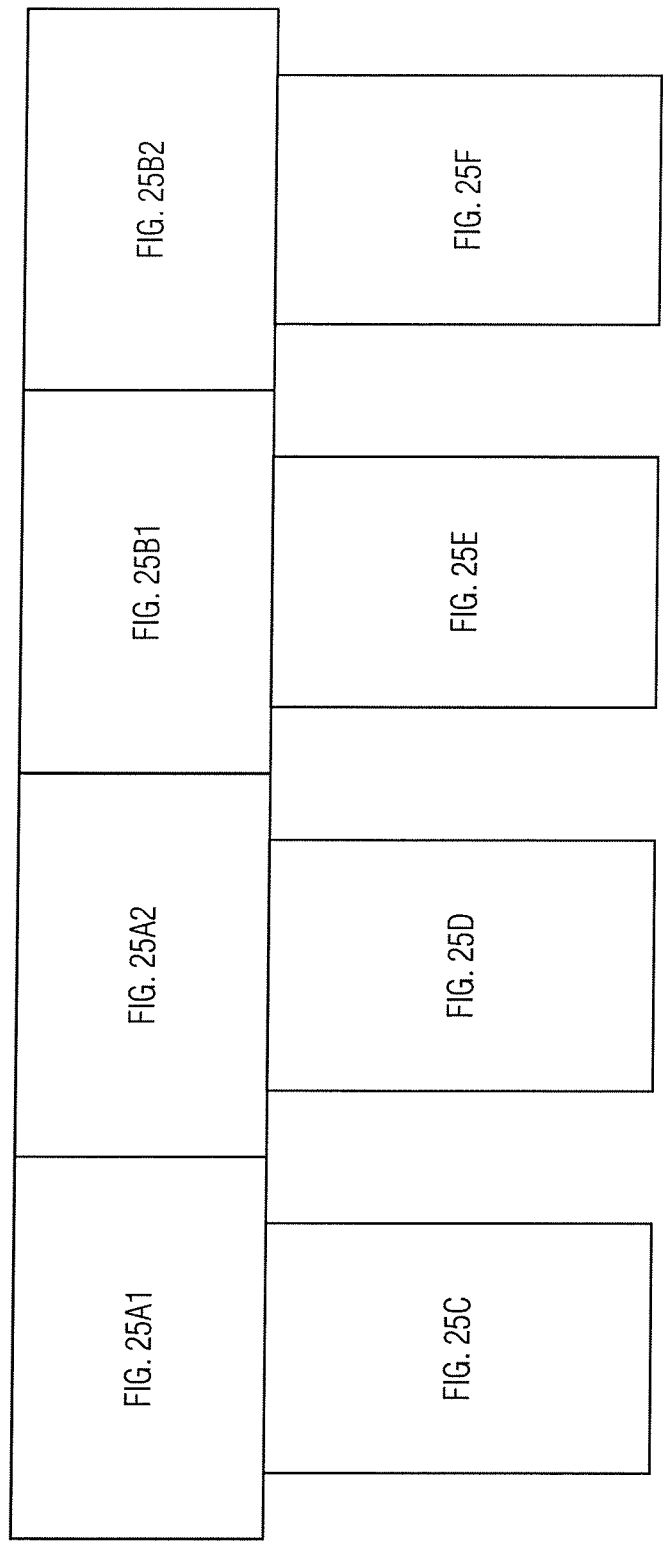
FIG. 25 is a legend showing the interrelationship of FIGS. 25A, 25B, 25C, 25D, 25E and 25F, which comprise a flow chart illustrating the operation of a repeater unit in a communications system in which any of the mobile units may or may not have motion detection capability.
Figure 26:
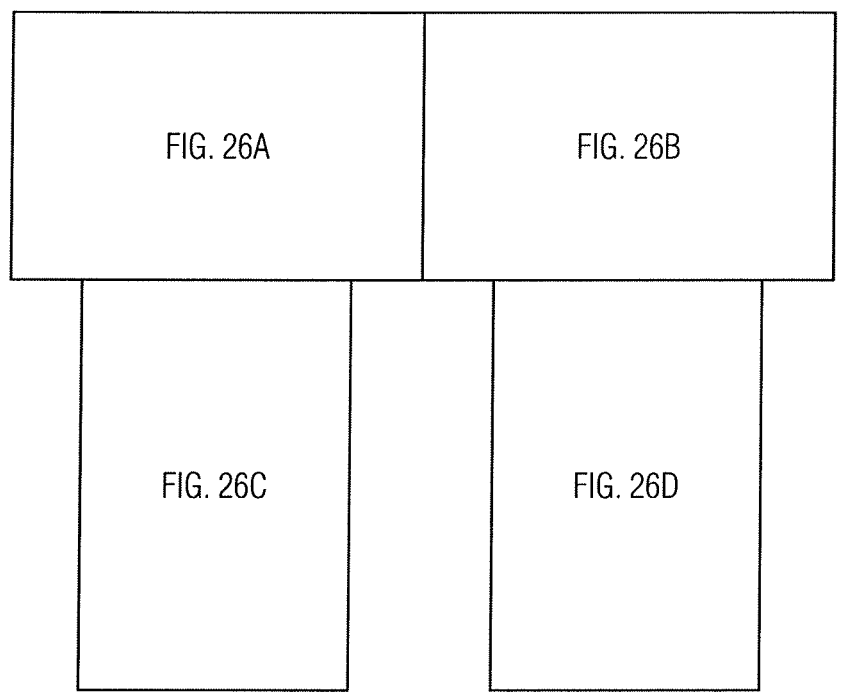
FIG. 26 is a legend showing the interrelationship of FIGS. 26A, 26B, 26C, and 26D, which comprise a flow chart illustrating the operation of the most upstream repeater unit in a communications system in which any of the mobile units may or may not have motion detection capability.
Figure 26A:
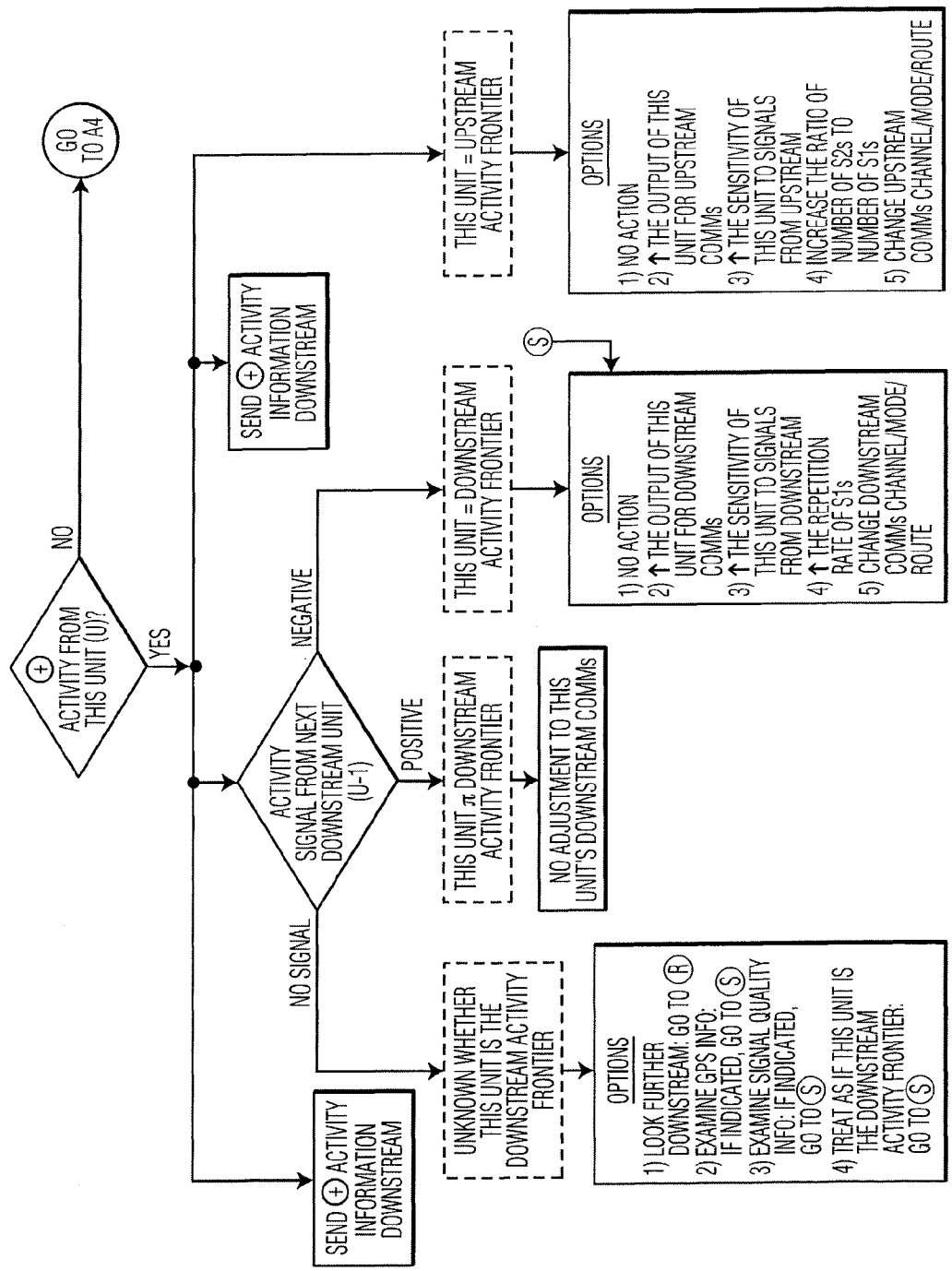

FIGS. 24-26 parallel FIGS. 20-22 (IMD, repeater unit, final repeater unit); but FIGS. 24-26 allow for the possibility that a neighboring unit does not have motion detecting capability.

FIG. 24, is an algorithm for an IMD with MDC, which allows for operation with an upstream unit which either does or does not have MDC (whereas FIG. 20 is an algorithm for an IMD with MDC, which allows for operation only with an upstream unit which has MDC). Accordingly, additional options in FIG. 24 (compared to FIG. 20) address the case of no activity signal from the upstream neighboring unit, and these are discussed presently:

Referring to FIG. 24A, if the IMD is moving, and if the activity status of the next upstream unit is not provided by a MD/A/P in that unit, then options include:

a) looking further upstream than the adjacent unit; FIG. 24B shows an algorithm which looks at the two next upstream units (designated U+2 and U+3) beyond the unit which is adjacent to the IMD (designated U+1). If the information is obtained from U+2, then U+3 is not examined; If the information is not obtained from U+2, then U+3 is examined. Implicit in the algorithm is the concept that the motion state of unit U+1 is likely to be the same as that of U+2, and that the motion of U+2 is likely to be the same as that of U+3. Thus if the IMD is moving, and if the motion status of U+1 is unknown, but U+2 (or, if necessary, U+3) is known to be moving, then the conclusion is that the IMD is not likely to be the upstream activity frontier. On the other hand, if the IMD is moving, and if the motion status of U+1 is unknown, but U+2 (or, if necessary, U+3) is known not to be moving, then the conclusion is that the IMD may be the upstream activity frontier. In each case, conclusions based on U+2 are more reliable than those based on U+3. Clearly, it would be possible to allow the system to look even further upstream, i.e. at U+4, etc., which would be desirable, as shown in FIG. 24B, if neither of unit U+2 nor unit U+3 had MDC;

b) [again referring to FIG. 24A] looking at GPS or signal quality information to try to determine the motion status of the IMD with respect to unit U+1. Note that FIG. 24B also calls for the possible consideration of GPS and/or signal quality information, if MD/A/P data from U+2 and beyond is insufficient for a decision;

c) [again referring to FIG. 24A] simply making the assumption that the IMD is the upstream activity frontier (i.e. "err" on the side of more robust communications), and selecting one of the options led to from Circle N, which increase the assiduousness of upstream communications from the IMD; This approach is also indicated as an option in FIG. 24B, in the event that neither of U+2 nor U+3 offers MD/A/P information; and/or d) taking no action.

The other difference between FIG. 24 and FIG. 20 is the inclusion in FIG. 24 of a set of options for the combination of no IMD motion and no MD/A/P signal from the next upstream communications unit. The options are conceptually parallel to those immediately above for the case of IMD motion and no MDC in the upstream unit.

Referring again to FIG. 24A, if the IMD is not moving, and if the activity status of the next upstream unit is not provided by a MD/A/P in that unit, then options include:

a) looking further upstream than the adjacent unit; FIG. 24C shows an algorithm which looks at the two next upstream units (U+2 and U+3) beyond the unit which is adjacent to the IMD (U+1). If the information is obtained from U+2, then U+3 is not examined; If the information is not obtained from U+2, then U+3 is examined. As was the case with FIG. 24B, implicit in the algorithm is the concept that the motion state of unit U+1 is likely to be the same as that of U+2, and that the motion of U+2 is likely to be the same as that of U+3. Thus if the IMD is not moving, and if the motion status of U+1 is unknown, but U+2 (or, if necessary, U+3) is known to be moving, then the conclusion is that unit U+1 may be the downstream activity frontier, and options include efforts to increase the assiduousness of communications between U and U+1. On the other hand, if the IMD is not moving, and if the motion status of U+1 is unknown, but U+2 (or, if necessary, U+3) is known not to be moving, then the conclusion is that there may be an overall quiescent state, and options to decrease the assiduousness of communications between U and U+1 may be undertaken. As was the case with FIG. 24B, (i) in each case, conclusions based on U+2 are more reliable than those based on U+3; and (ii) clearly, it would be possible to allow the system to look even further upstream, i.e. at U+4, etc., which would be desirable, as shown in FIG. 24C, if neither of unit U+2 nor unit U+3 had MDC;

b) [again referring to FIG. 24A] looking at GPS or signal quality information to try to determine the motion status of the IMD with respect to unit U+1. Note that FIG. 24C also calls for the possible consideration of GPS and/or signal quality information, if MD/A/P data from U+2 and beyond is insufficient for a decision;

c) [again referring to FIG. 24A] simply making the assumption that the lack of IMD motion is part of an overall quiescent state, and therefore selecting one of the options led to from Circle Q, which decrease the assiduousness of upstream communications from the IMD; This approach is also indicated as an option in FIG. 24C, in the event that neither of U+2 nor U+3 offers MD/A/P information; and/or d) taking no action.

FIG. 25, is an algorithm for a repeater unit with MDC, which allows for operation with (i) an upstream unit which either does or does not have MDC (whereas FIG. 21 is an algorithm for a repeater unit with MDC, which allows for operation only with an upstream unit which has MDC); and (ii) a downstream unit which either does or does not have MDC (whereas FIG. 21 is an algorithm for a repeater unit with MDC, which allows for operation only with a downstream unit which has MDC).

Accordingly, four additional sets of options in FIG. 25 (compared to FIG. 21) address the case of no activity signal from the neighboring units, and these are discussed hereinbelow. The four sets of options are for:

Case 1: repeater unit in motion, no upstream activity signal from MD/A/P;

Case 2: repeater unit in motion, no downstream activity signal from MD/A/P;

Case 3: repeater unit in not in motion, no upstream activity signal from MD/A/P; and Case 4: repeater unit in not in motion, no downstream activity signal from MD/A/P.

Figure 25C:
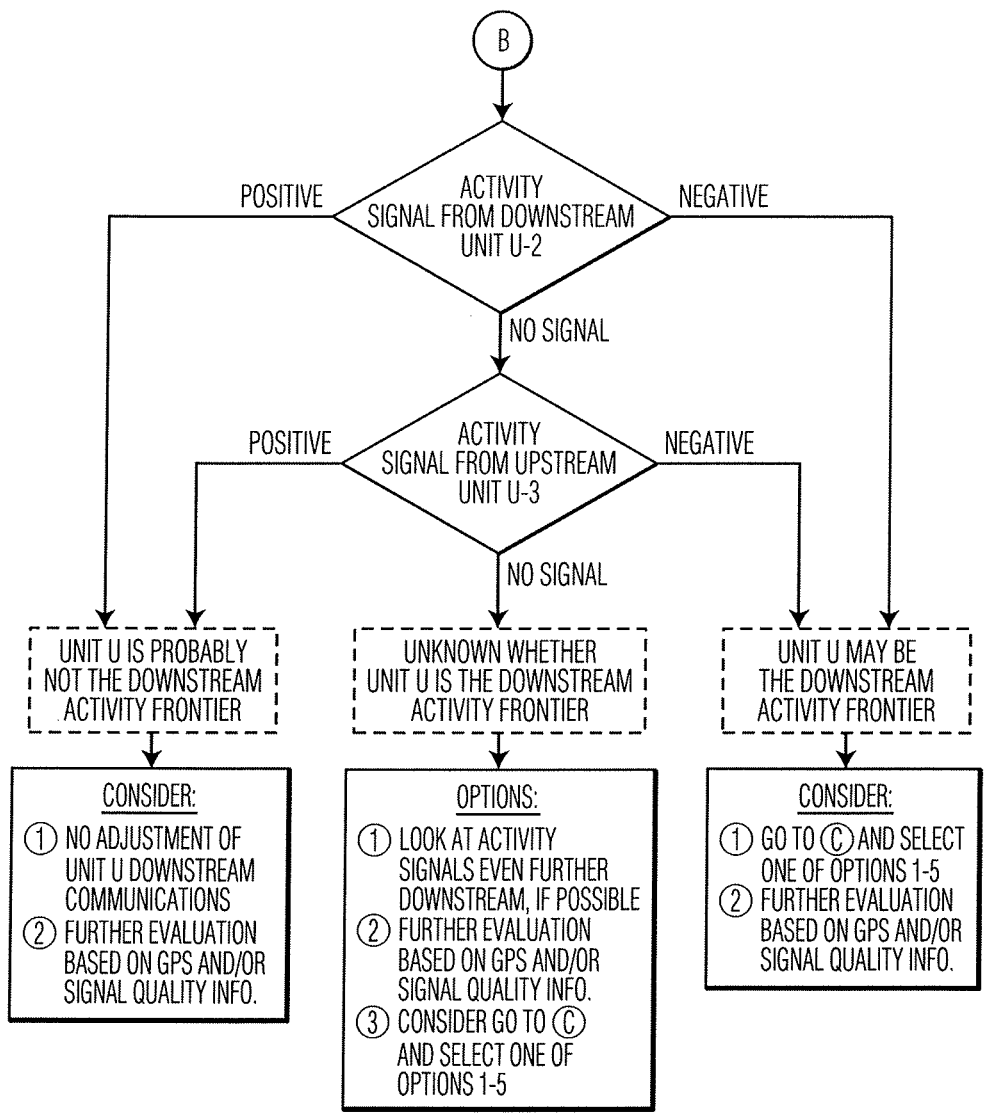
Figure 25D:
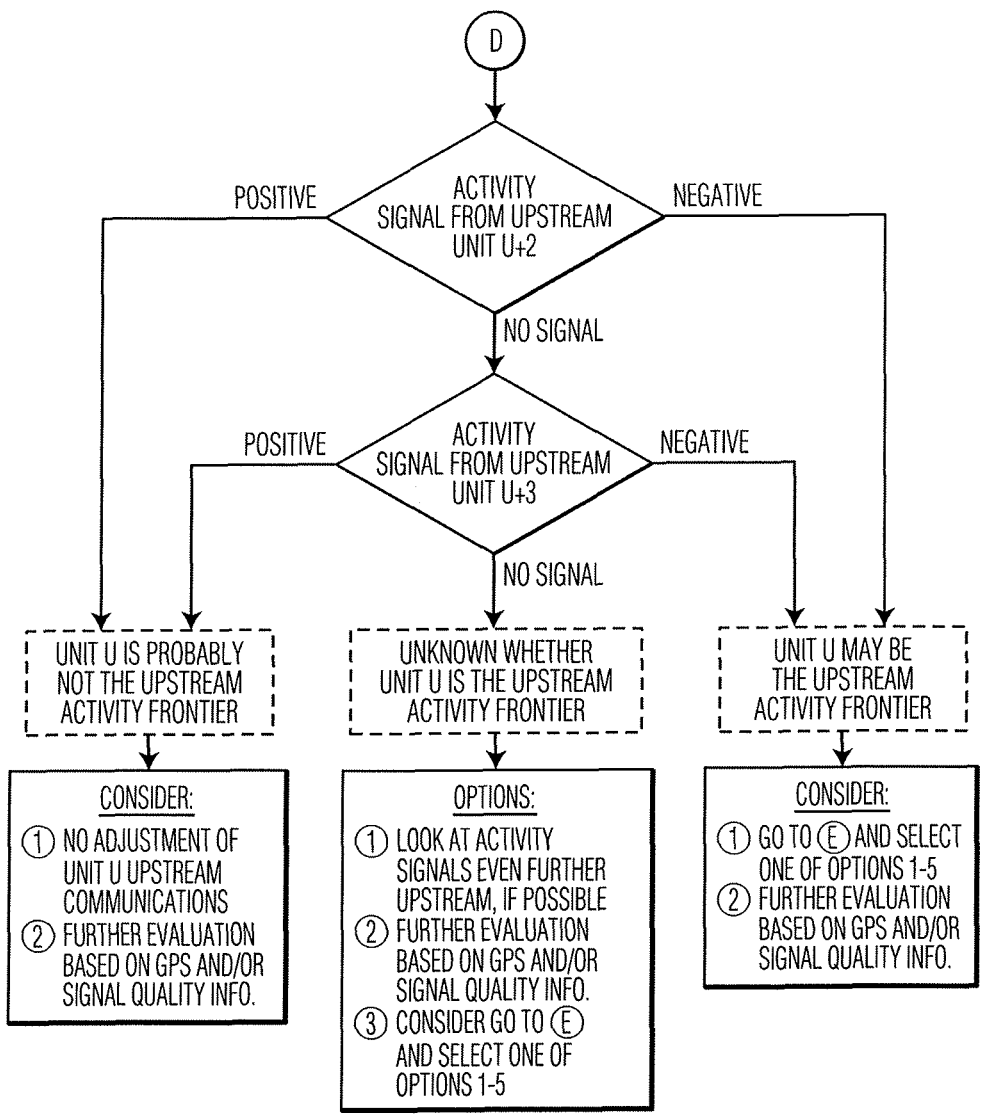

Regarding Case 1 (immediately above): Referring to FIG. 25A, if the repeater unit is moving, and if the activity status of the next upstream unit is not provided by a MD/A/P in that unit, then the management options are conceptually parallel to those enumerated in the case of the IMD with repeater unit indicating motion and with upstream unit not having MD/A/P (FIG. 24), including:

a) looking further upstream than the adjacent unit; FIG. 25D shows an algorithm which looks at the two next upstream units (U+2 and U+3) beyond the unit which is next upstream from the repeater (U+1). The algorithm is conceptually identical to that shown in FIG. 24B: If the information is obtained from U+2, then U+3 is not examined; If the information is not obtained from U+2, then U+3 is examined; If the information is not obtained from either U+2 or U+3, looking further upstream is a possibility;

b) [again referring to FIG. 25A] looking at GPS or signal quality information to try to determine the motion status of the repeater unit with respect to unit U+1. Note that FIG. 25D also calls for the possible consideration of GPS and/or signal quality information, if MD/A/P data from U+2 and beyond is insufficient for a decision;

c) [again referring to FIG. 25A] simply making the assumption that the repeater unit is the upstream activity frontier, and selecting one of the options led to from Circle E, which increase the assiduousness of upstream communications from the repeater unit; This approach is also indicated as an option in FIG. 25D, in the event that neither of U+2 nor U+3 offers MD/A/P information; and/or d) taking no action.

Regarding Case 2: Referring to FIG. 25A, if the IMD is moving, and if the activity status of the next downstream unit is not provided by a MD/A/P in that unit, then options are conceptually parallel to those enumerated in Case 1, including:

a) looking further downstream than the adjacent unit; FIG. 25C shows an algorithm which looks at the two next downstream units (designated U−2 and U−3) beyond the unit which is adjacent to the repeater unit (designated U−1). If the information is obtained from U−2, then U−3 is not examined; If the information is not obtained from U−2, then U−3 is examined. Implicit in the algorithm is the concept that the motion state of unit U−1 is likely to be the same as that of U−2, and that the motion of U−2 is likely to be the same as that of U−3. Thus if the repeater is moving, and if the motion status of U−1 is unknown, but U−2 (or, if necessary, U−3) is known to be moving, then the conclusion is that the repeater unit is not likely to be the downstream activity frontier. On the other hand, if the repeater unit is moving, and if the motion status of U−1 is unknown, but U−2 (or, if necessary, U−3) is known not to be moving, then the conclusion is that the repeater unit may be the downstream activity frontier. In each case, conclusions based on U−2 are more reliable than those based on U−3. Clearly, it would be possible to allow the system to look even further downstream, i.e. at U−4, etc., which would be desirable, as shown in FIG. 25C, if neither of unit U−2 nor unit U−3 had MDC;

b) [again referring to FIG. 25A] looking at GPS or signal quality information to try to determine the motion status of the repeater unit with respect to unit U−1. Note that FIG. 25C also calls for the possible consideration of GPS and/or signal quality information, if MD/A/P data from U−2 and beyond is insufficient for a decision;

c) [again referring to FIG. 25A] simply making the assumption that the repeater unit is the downstream activity frontier (i.e. "err" on the side of more robust communications), and selecting one of the options led to from Circle C, which increase the assiduousness of downstream communications from the repeater unit; This approach is also indicated as an option in FIG. 25C, in the event that neither of U−2 nor U−3 offers MD/A/P information; and/or d) taking no action.

Figure 25E:
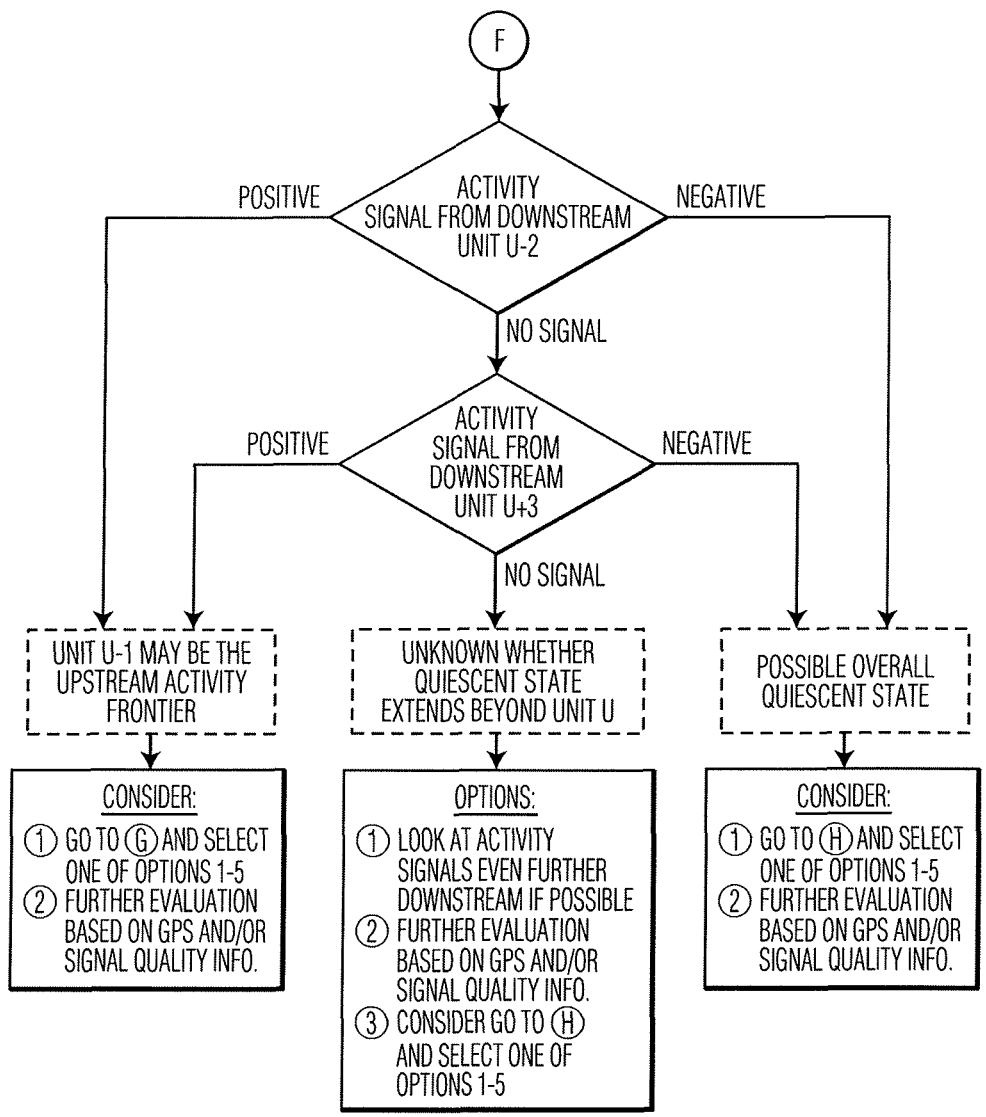
Figure 25F:
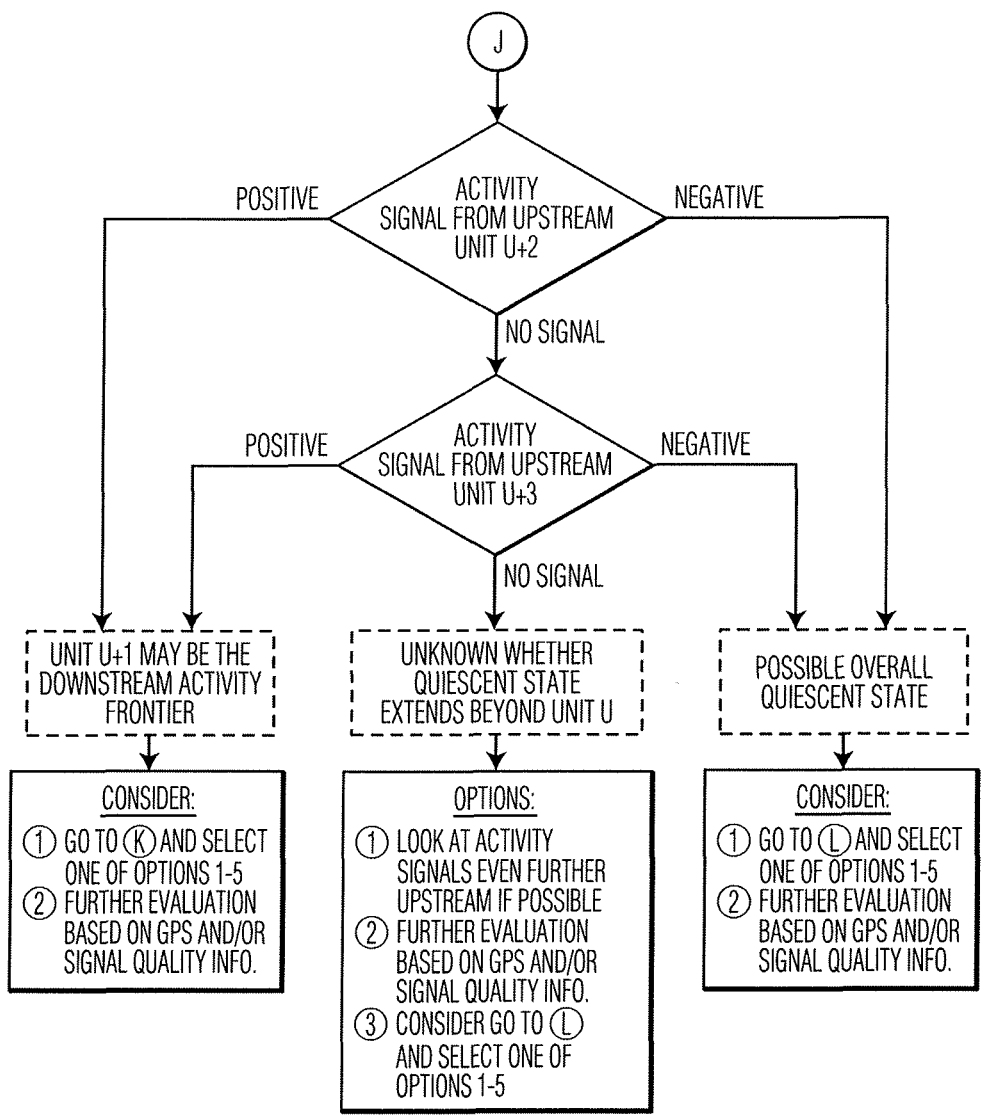

Regarding Case 3 (hereinabove): Referring to FIG. 25B, if the repeater unit is not moving, and if the activity status of the next upstream unit is not provided by a MD/A/P in that unit, then the management options are conceptually parallel to those enumerated in the case of the IMD with repeater unit indicating no motion and with upstream unit not having MD/A/P (FIG. 24), including:

a) looking further upstream than the adjacent unit; FIG. 25F shows an algorithm which looks at the two next upstream units (U+2 and U+3) beyond the unit which is next upstream from the repeater (U+1). The algorithm is conceptually identical to that shown in FIG. 24C: If the information is obtained from U+2, then U+3 is not examined; If the information is not obtained from U+2, then U+3 is examined; If the information is not obtained from either U+2 or U+3, then looking further upstream is a possible option;

b) [again referring to FIG. 25B] looking at GPS or signal quality information to try to determine the motion status of the repeater unit with respect to unit U+1. Note that FIG. 25F also calls for the possible consideration of GPS and/or signal quality information, if MD/A/P data from U+2 and beyond is insufficient for a decision;

c) [again referring to FIG. 25B] simply making the assumption that the repeater unit is part of a local quiescent state, and selecting one of the options led to from Circle L, which decrease the assiduousness of upstream communications from the repeater unit; This approach is also indicated as an option in FIG. 25F, in the event that neither of U+2 nor U+3 offers MD/A/P information; and/or d) taking no action.

Regarding Case 4 (hereinabove): Referring to FIG. 25B, if the repeater unit is not moving, and if the activity status of the next downstream unit is not provided by a MD/A/P in that unit, then the management options are conceptually parallel to those enumerated in Case 3, including:

a) looking further downstream than the adjacent unit; FIG. 25E shows an algorithm which looks at the two next downstream units (U−2 and U−3) beyond the unit which is next upstream from the repeater (U−1). If the information is obtained from U−2, then U−3 is not examined; If the information is not obtained from U−2, then U−3 is examined; If the information is not obtained from either U−2 or U−3, then looking further downstream is a possible option;

b) [again referring to FIG. 25B] looking at GPS or signal quality information to try to determine the motion status of the repeater unit with respect to unit U−1. Note that FIG. 25E also calls for the possible consideration of GPS and/or signal quality information, if MD/A/P data from U−2 and beyond is insufficient for a decision;

c) [again referring to FIG. 25B] simply making the assumption that the repeater unit is part of a local quiescent state, and selecting one of the options led to from Circle H, which decrease the assiduousness of downstream communications from the repeater unit; This approach is also indicated as an option in FIG. 25E, in the event that neither of U−2 nor U−3 offers MD/A/P information; and/or d) taking no action.

As was the case with FIG. 21 (repeater unit for system in which all units have MDC), the repeater unit algorithm shown in FIG. 25 also allows for:

a) the detection of a lost or misplace unit; and
b) an increased level of certain about a the existence of a quiescent state when three consecutive units are each in a non-motion state.

Figure 26B:
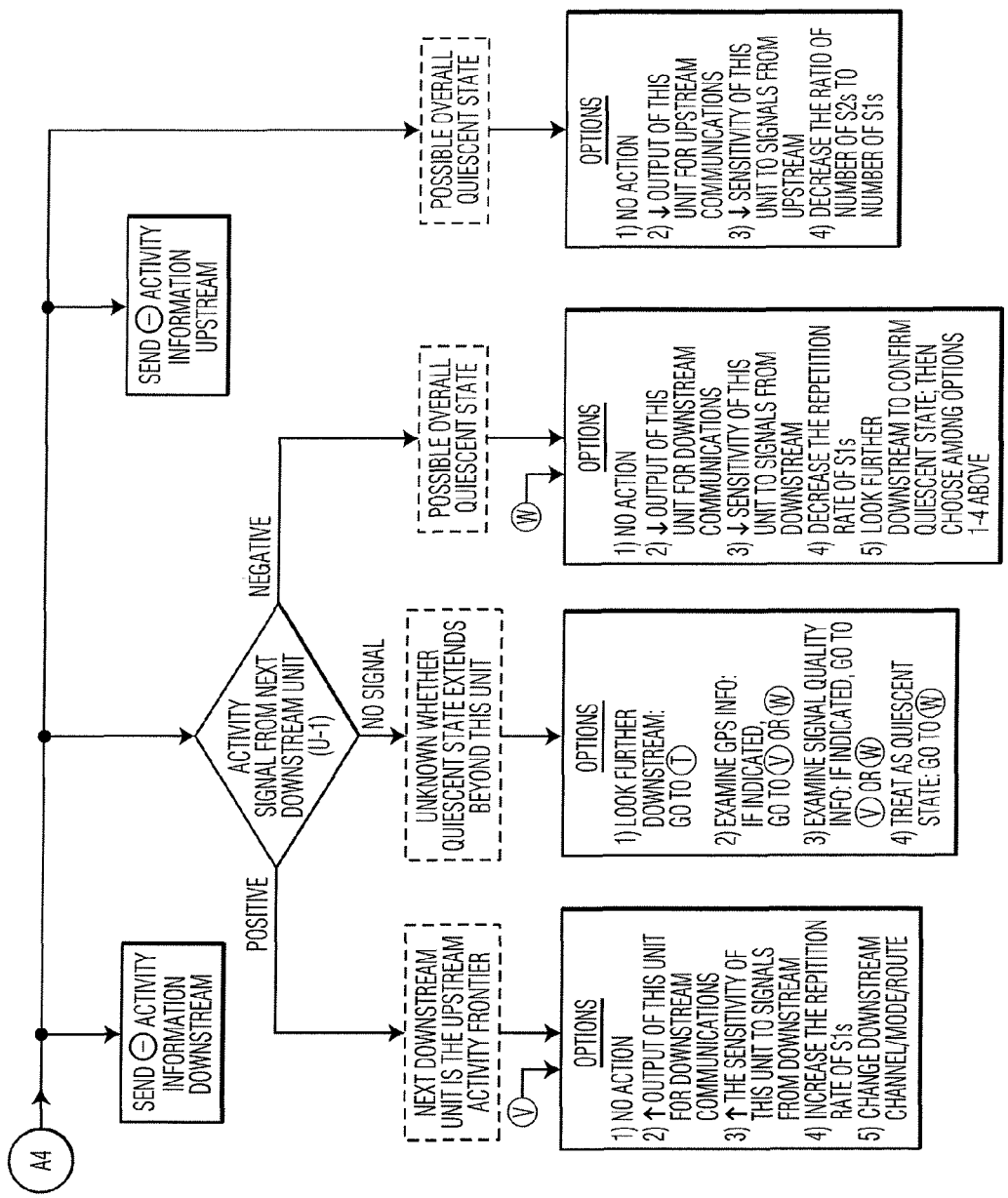
Figure 26C:
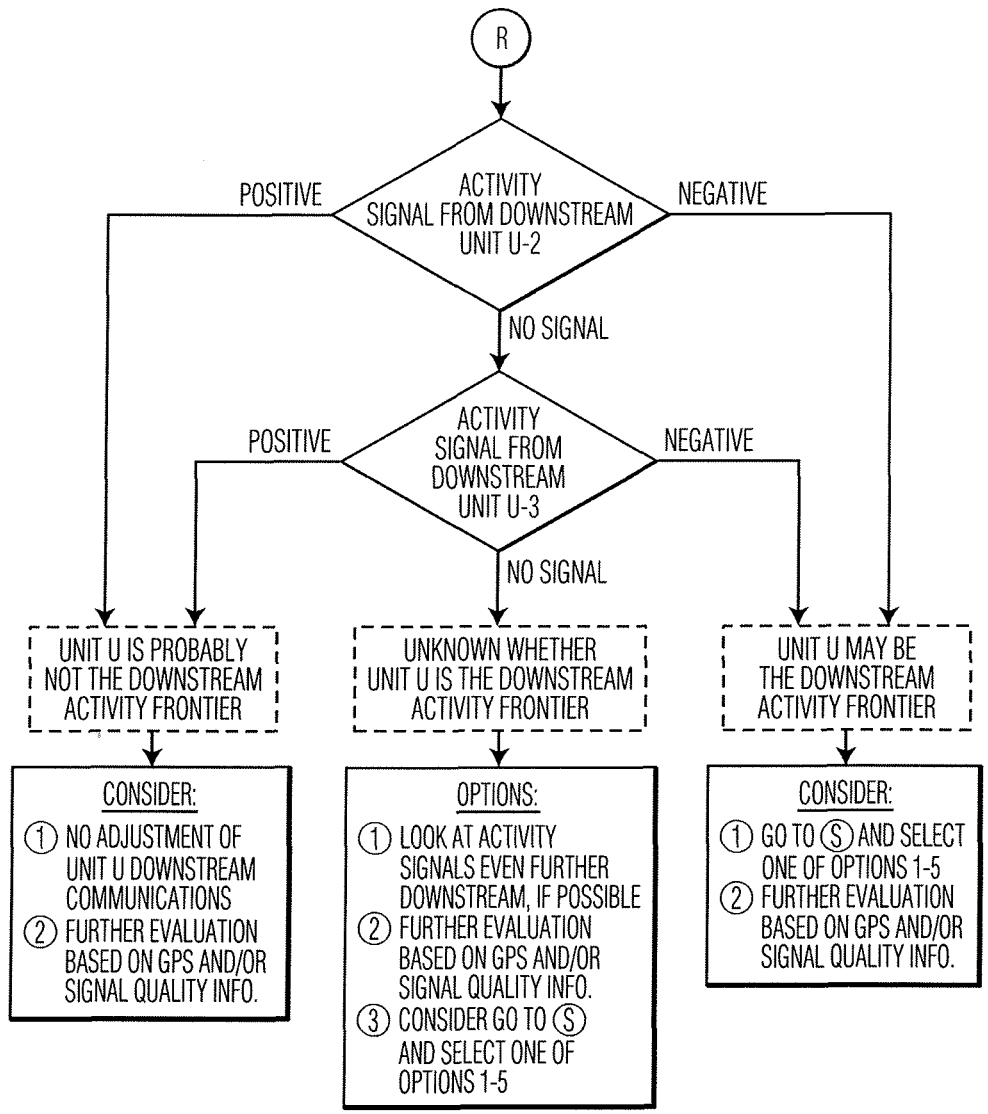
Figure 26D:
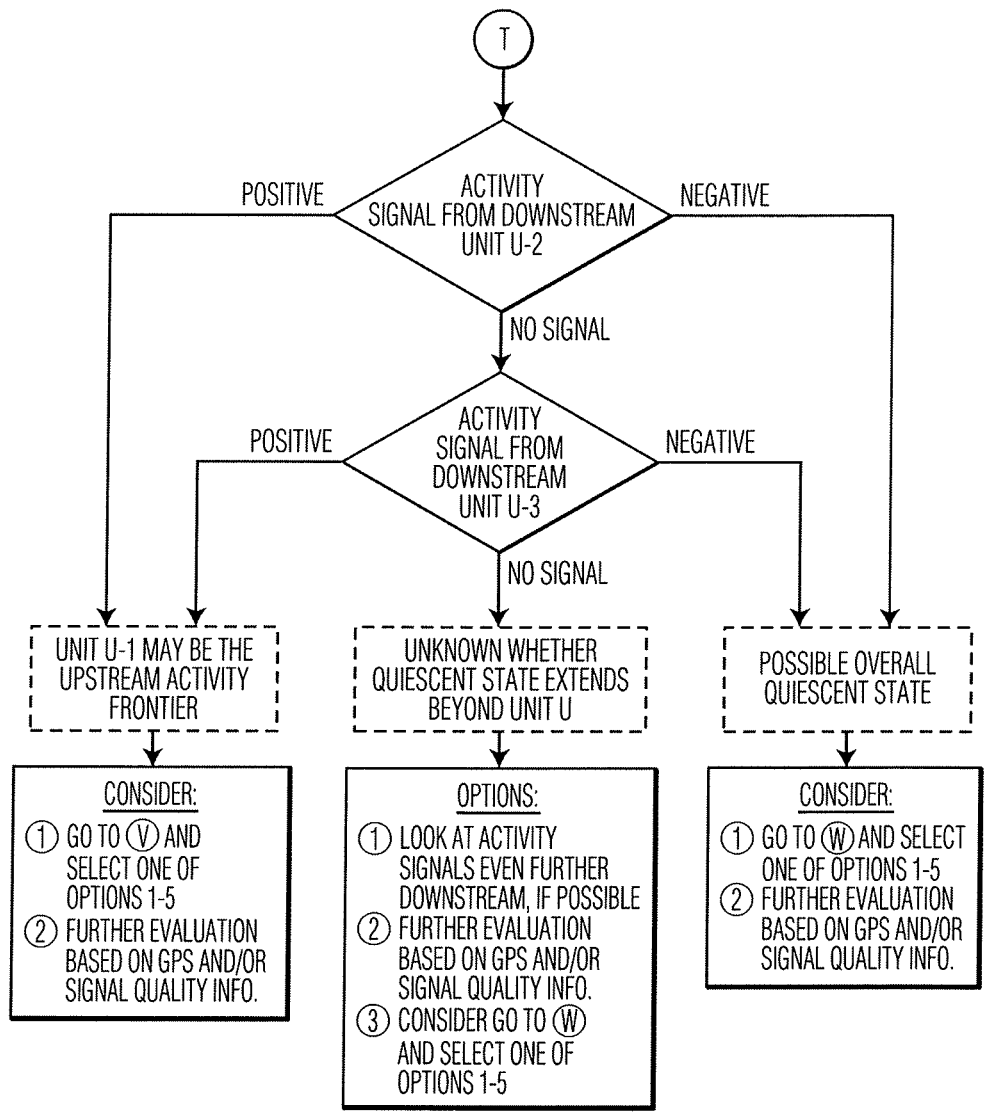

FIG. 26, is an algorithm for a final repeater unit with MDC, which allows for operation with a downstream unit which either does or does not have MDC (whereas FIG. 22 is an algorithm for a final repeater unit with MDC, which allows for operation only with a downstream unit which has MDC). The algorithm is essentially the same as that of FIG. 25 for the general repeater, except that all upstream communications are understood to be with a unit that is in a non-motion state. This eliminates upstream communication considerations related to either (i) a moving upstream unit or (ii) an upstream unit whose motion status is uncertain. (Also, option 5 of the list of options led to by Circle L in FIG. 25B is eliminated in FIG. 26B, since it calls for additional evaluation by looking at the motion state further upstream.)

To complete the possible configurations of a mixed system, which includes both (i) mobile communicating units with and (ii) mobile communicating units without MDC, algorithms are presented for each of an IMD, a repeater unit and a final repeater unit which do not have MDC but which operate with one or more adjacent units which do have MDC.

Figure 27A:
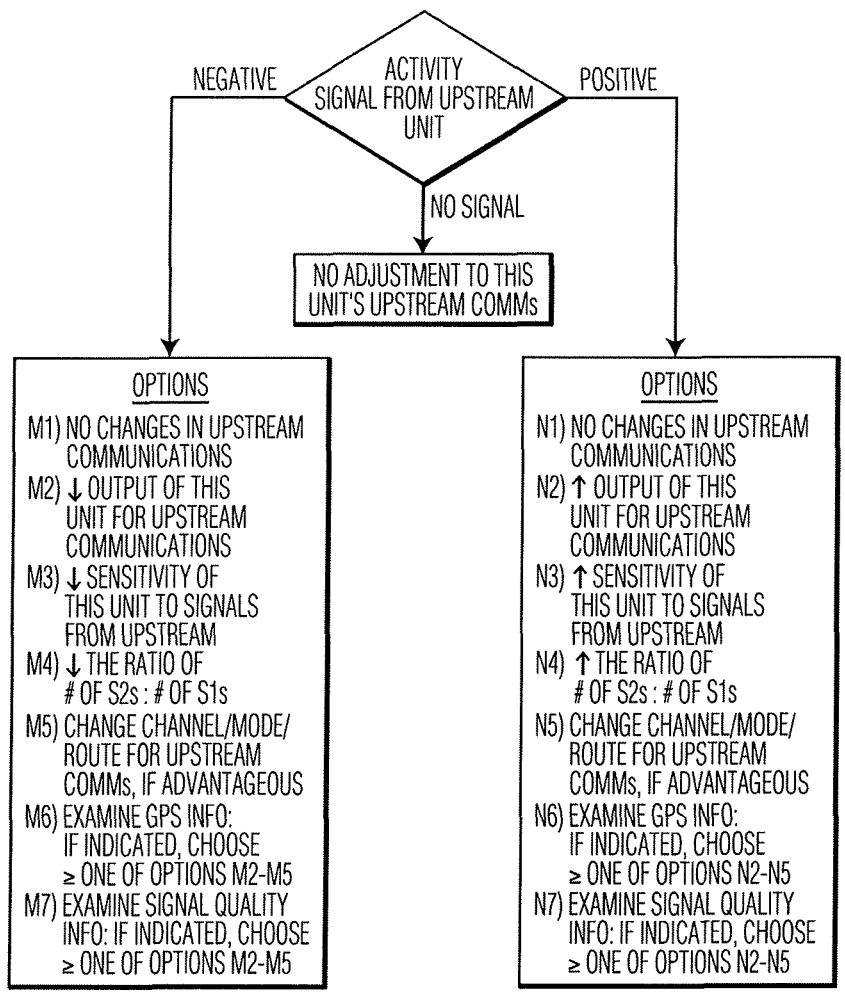
FIG. 27A is a flow chart illustrating the operation of an implantable medical device which does not have motion detection capability, in a communications system in which one or more other mobile units have motion detection capability.

FIG. 27A shows an IMD which does not have MDC, but which may receive and respond to signals derived from MD/A/P apparatus in its adjacent upstream neighbor. If the upstream unit shows no activity, then the listed options M1-M7 include (i) a decrease in the assiduousness of upstream communications, based on the assumption of a locally quiescent state; (ii) further evaluation based on an examination of either GPS or signal quality data; or (iii) no change in communication management. An algorithm which does not decrease the assiduousness of upstream communication in the event of a negative activity signal from upstream is possible, since in that circumstance, the IMD could be the upstream activity frontier.

If the upstream unit shows activity, then the listed options N1-N7 include (i) an increase in the assiduousness of upstream communications, based on the assumption that one can't rule out the next upstream unit being the downstream activity frontier; (ii) further evaluation based on an examination of either GPS or signal quality data; or (iii) no change in communication management. No signal from upstream calls for no action. An algorithm which does not increase the assiduousness of upstream communication in the event of a positive activity signal from upstream is possible, since in that circumstance, the IMD could be moving with the upstream unit. Algorithms which look further upstream than the adjacent communications unit (no matter which signal is received from that adjacent unit) are possible.

Figure 27B:
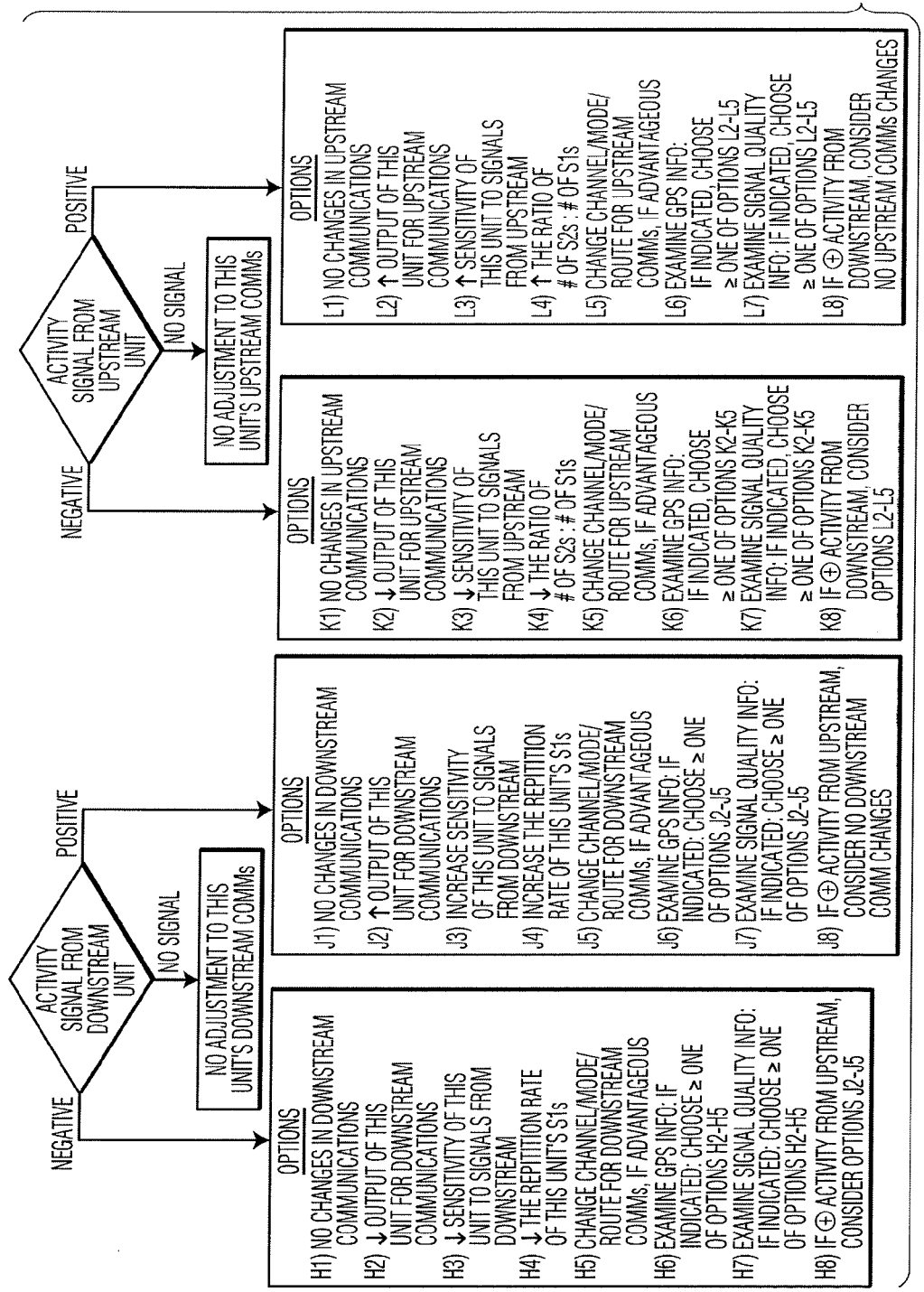
FIG. 27B is a flow chart illustrating the operation of a repeater unit which does not have motion detection capability, in a communications system in which one or more other mobile units have motion detection capability.

FIG. 27B shows a repeater unit without MDC which may receive and respond to signals derived from MD/A/P apparatus in (i) its adjacent upstream neighbor, and (ii) its adjacent downstream neighbor. Responses K1-K7 to negative activity signals from an upstream unit are the same as those for the IMD without MDC (M1-M7). In addition, in the case of the repeater herein, if a positive activity signal is received from downstream, then consideration is given to the possibility that the repeater herein could be in a positive activity state, making it the upstream activity frontier; In such a circumstance, options which increase the activity of upstream communications are desirable (L2-L5).

Responses L1-L7 to positive activity signals from an upstream unit are the same as those for the IMD without MDC (N1-N7). In addition, in the case of the repeater herein, if a positive activity signal is received from downstream, then consideration is given to the possibility that the repeater herein could be in a positive activity state, implying the possibility that all three adjacent units are moving together; In such a circumstance, there would be no need to increase the assiduousness of upstream communications.

If there is no signal from the upstream communications unit, the algorithm calls for no communication modification at the repeater unit described herein.

The response of the repeater unit without MDC to downstream activity information is conceptually parallel to its response to upstream activity information. A negative downstream activity signal leads to options H1-H7, which parallel options K1-K7 (except that the repetition rate of S1s is the subject of H4, while the repetition rate of S2s is the subject of K4). In addition, in the case of the repeater herein, if a positive activity signal is received from upstream, then consideration is given to the possibility that the repeater herein could be in a positive activity state, making it the downstream activity frontier; In such a circumstance, options which increase the activity of downstream communications are desirable (J2-J5). A positive downstream activity signal leads to options J147, which parallel options L1-L7 (except that the repetition rate of S1s is the subject of J4, while the repetition rate of S2s is the subject of L4). In addition, in the case of the repeater herein, if a positive activity signal is received from upstream, then consideration is given to the possibility that the repeater herein could be in a positive activity state, implying the possibility that all three adjacent units are moving together; In such a circumstance, there would be no need to increase the assiduousness of downstream communications. Finally, if there is no signal from the downstream communications unit, the algorithm calls for no communication modification at the repeater unit described herein.

Figure 27C:
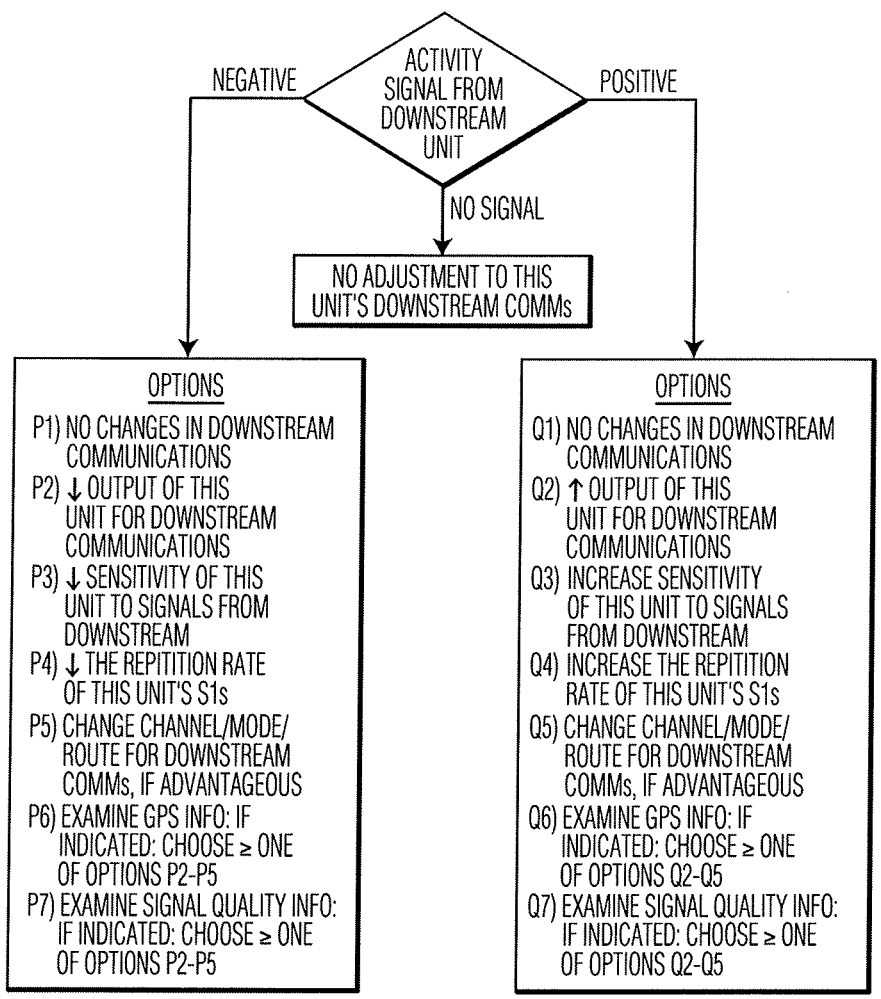
FIG. 27C is a flow chart illustrating the operation of a most upstream repeater unit which does not have motion detection capability, in a communications system in which one or more other mobile units have motion detection capability.

FIG. 27C shows an operating algorithm for a final repeater unit (i.e. the repeater which communicates with the SU) which does not have MDC. Because, by definition, the state of motion of the next upstream communications unit is known to be stationary, the algorithm omits (i) all of the response options to upstream activity signals shown in FIG. 27B; and (ii) options analogous to H8 and J8 of FIG. 27B [since they also concern upstream motion]. Thus options P1-P7 parallel options H1-H7, and options Q1-Q7 parallel options J147.

FIGS. 20-27C initially consider only the information from accelerometer or piezoelectric motion detecting apparatus, and consider GPS and/or signal quality information on a secondary basis. FIGS. 12 and 13 consider GPS and signal quality without blending in MD/A/P information. However, algorithms for position, motion and acceleration analysis may be based other ways of "blending" the information from (i) MD/A/P information, (ii) GPS information and (iii) signal quality information, e.g.

considering GPS as the primary data (e.g. in an algorithm similar to that shown in FIGS. 20-27C, and in which, optionally, one or more of MD/A/P information and signal quality information are secondary considerations);

considering signal quality is used as the primary data, with one or more of MD/A/P and GPS as secondary information;

consider a blend of any two modalities as the primary data (e.g. [i] define a positive motion state if either of GPS or MD/A/P indicates activity, or [ii] define a positive motion state if both GPS and MD/A/P indicate activity);

consider a blend of all three as the primary data (e.g. [i] define a positive motion state if any of GPS or signal quality or MD/A/P indicates activity, or [ii] define a positive motion state if any two out of three of GPS, signal quality and MD/A/P indicate activity, or [iii] define a positive motion state if all of GPS, signal quality and MD/A/P indicate activity, or [iv] define a positive motion state if signal quality and either of GPS or MD/A/P indicate activity, etc.)

Still other ways of blending the information will be apparent to those skilled in the art.

Even more complex algorithms result from the consideration of General Principle 12 hereinabove, i.e. that activity may be considered in a more "fine grained" manner than simply all or none. For example, a five state format could include (i) negative, (ii) weakly positive, (iii) intermediate positive, (iv) strongly positive, and (v) unknown. A multi-state format (involving the same, a lesser number or a greater number of states) could be used for one or more of MD/A/P, GPS and signal quality information in a blended format.

In these systems with augmented motion detection capabilities, the basic goals are the same as those defined hereinabove, i.e. the use of motion information to optimize signal quality and battery drainage, each in both real time, and proactively.

Figure 28:
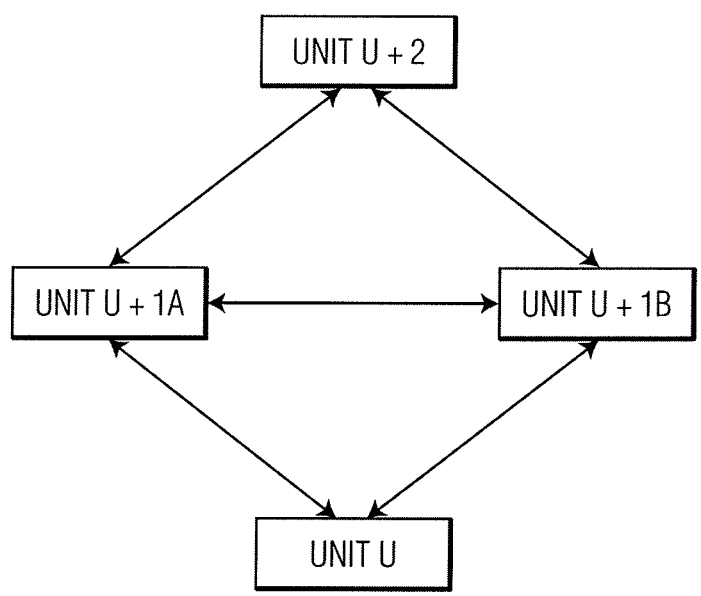
FIG. 28 is a block diagram showing parallel communication paths between two communication units.

The approach hereinabove general concerns tandem communication units with a "series" structure, i.e. unit U sends IMD information to unit U+1, which relays the information to unit U+2, etc. However, parallel communication elements, as illustrated in FIG. 28, can increase the reliability of the system. FIG. 28 shows a network structure in which unit U communicates with unit U+2 via (i) unit U+1A, (ii) unit U+1B, (iii) unit U+1A followed by unit U+1B, or (iv) unit U+1B followed by unit U+1A. With this architecture, the loss of any one communications link will not prevent U and U+2 from communicating, and some configurations with up to three non-functioning links will still allow U and U+2 to communicate.

For example, if both of (i) the link between U and U+1A, and (ii) the link between U+1B and U+2 are non-functioning, then U can communicate with U+2 via the route U←→U+1B←→U+1A←→U+2. U could either send information to both U+1A and U+1B, or, if U was provided with the information that the best route is U←→U+1B←→U+1A←→U+2, then U could send information only to U+1B. All of the aforementioned potentially applies in the reverse direction—i.e. U+2 sending information to U, but it is not necessarily a given that the optimum U+2 to U route is simply the inverse of the U to U+2 route, because an upstream transmitter may have different power output than a downstream one, because receiver characteristics may differ, and because of different transmission channels.

Figure 29A:
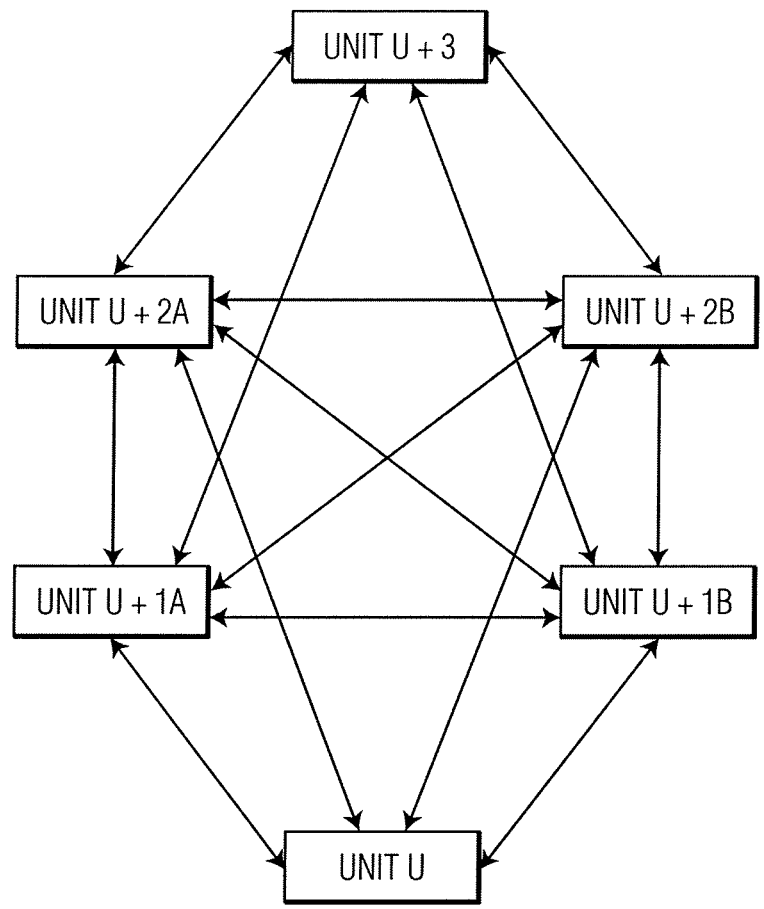
FIG. 29A is a block diagram showing a communication network with both series and parallel communication elements.

An example of the communication elements which may form the network shown in FIG. 28 is:
Unit U=IMD
Unit U+1A=WD
Unit U+1B=CPD
Unit U+2=SU FIG. 29A shows a more complex arrangement than that of FIG. 28. Although there are only two more communication repeater units, there are many more communication links (14 vs. 5) and a much larger number of routes between the first and the last unit (40 {[4×3×2]+[4×3]+4} vs. 4). With this architecture, the loss of any three communications links will not prevent U and U+3 from communicating, and some configurations with up to 11 non-functioning links will still allow units U and U+3 to communicate.

One feature which increases the number of possible system paths in FIG. 28, compared to 29, is allowing for not only "lateral" communication (e.g. unit U+1A and unit U+1B may communicate), but also allowing for "backward communication," (e.g. unit U communicates with unit U+3 via the path U←→U+2A←→U+1B←→U+3). This could occur because the repeater units are not arrayed geometrically in the pattern shown in the figure. In the previous example, the unit U is ordinarily expected to be nearer to unit U+1A than to U+2A, unit U+1A may have become misplaced or inoperative; the same may (misplacement or inoperative state) may be true of unit U+2B, hence the aforementioned choice of route.

An example of the communication elements which may form the network shown in FIG. 29A is:
Unit U=IMD
Unit U+1A=WD
Unit U+1B=CPD
Unit U+2A=SU#1
Unit U+2B=SU#2
Unit U+3=CS.

(In this case, it would be unlikely that one SU would send IMD information to the other or to a downstream location on the way to the CS.)

In another example, unit U is the IMD; while high capability RFIDs could constitute units U+1A and U+1B; unit U+2A could be a WD; unit U+2B could be a CPD; and unit U+3 a SU. In yet another example, the IMD is unit U; different types of WD (one on a wrist and one embedded in clothing) could constitute units U+1A and U+1B; units U+2A and U+2B could be two different CPDs; and unit U+3 a SU.

As indicated for the case of the configuration shown in FIG. 28, the units at each end of the network (the IMD and the CS) could send information to each possible neighboring unit, which could then continue sending information to each possible neighbor, ultimately resulting in dissemination of the information to all elements of the network. Alternatively, if the status of each communication link of the network is available to the CS and the IMD, then only the necessary repeater units would be sent the information. Since there are 14 two way links, there are 28 sets of data that indicate the quality of each of these links.

FIG. 29B illustrates an array of such information. The letter in each cell indicates the communication conditions from the unit labeled in the left-most column to the unit labeled in the top row. Thus C indicates the communication conditions from unit U+1A to unit U (e.g. the quality of a S1 received by sent by unit U+1A and received by unit U), while C* (which is not necessarily the same as C) indicates the communication conditions from unit U to unit U+1A (e.g. the quality of a S2 received by sent by unit U and received by unit U+1A). The blank boxes indicate units which do not communicate (i.e. each unit with itself, and the units at the far ends [in this case units U and U+3]). C could be a number (e.g. representing signal quality), or could be an array of numbers (e.g. each element in the array indicating [i] the communication conditions on each of a number of possible frequencies, [ii] the communication conditions using a number of different communication modalities, [iii] an evaluation of the error rate for data transmission, [iv]

other communication parameters, or [v] combinations of [i] to [iv]). Though the composite communication status information "CCSI" is presented as a matrix in FIG. 29B, it could simply be stored as one file with 28 numbers (or a multiple of 28 numbers), or 28 files, or in any of a variety of ways that will be obvious to those skilled in the art.

The CCSI can be stored in one of the communication units designated as the master unit; For example, each communication element could pass its information to the CS or the SU. Alternatively the information obtained at each unit could be passed along to its neighbors, so that it is ultimately disseminated over the entire network, resulting in each member of the network having access to the CCSI.

The number of columns in FIG. 29B, as well as the number of rows can be a greater or lesser number. The array can be two dimensional, one dimensional (i.e. a string of data with pre-defined demarcations), or have dimension number greater than two (e.g. if each cell in the matrix consists of data that can be arrayed multi-dimensionally. The overarching issue is that communication decisions may be made by storing network-wide communication conditions in one or more locations. It would also be possible to store communication conditions for only a local area; For example, the CPD could store information concerning all possible links downstream from it.

In one embodiment of the invention, a communications unit which stores all system-wide or all local communication information could be endowed with heuristic software so that, over a period of time, it learns certain patterns of activity of the IMD-owner which impact communications, and makes adjustments accordingly. This could involve turning down handshaking and position-confirming efforts during the IMD owner's sleep period (which could be determined by motion detecting apparatus in the IMD or in any device worn by or implanted in the IMD owner). Another example: On a certain night each week, the IMD owner goes bowling in a basement level area, or attends meetings in a basement level conference room. Communication adjustments could then be made in advance. It might be possible, for example, to strategically place the CPD so that it can adequately perform a repeater function with the IMD owner at the basement level. Alternatively, it might call for the installation of an SU at that location (either temporarily or permanently), which could directly access both (i) a telephone network or the internet, and (ii) an IMD owner communication device such as a CPD or WD.

Figure 30:
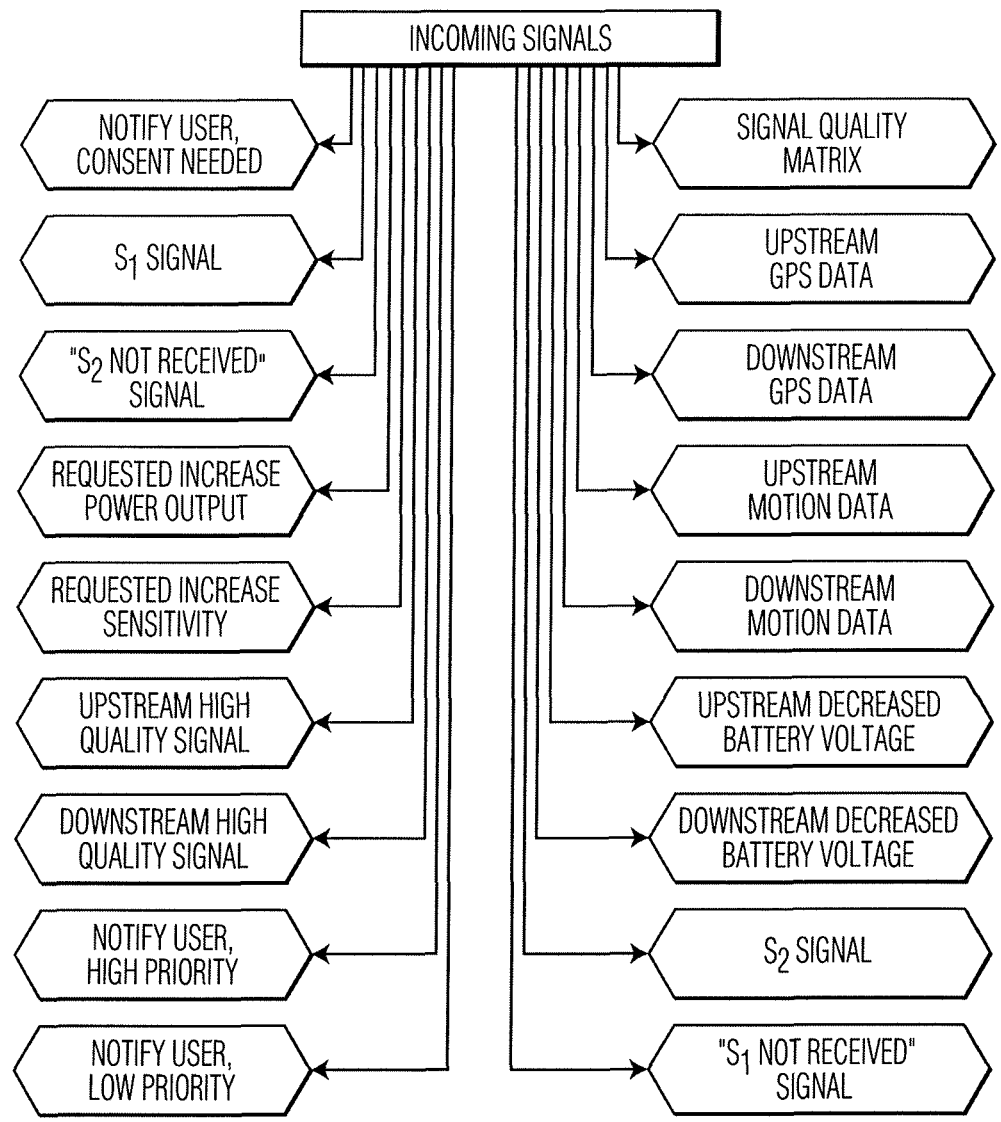
FIG. 30 is a block diagram showing incoming signals to a communications unit.

FIG. 30 shows the variety of signals which may enter a downstream communication unit. These include:
a) a routine S1 handshake signal from an upstream communications unit;
b) a signal indicating that the upstream communications unit is not receiving this unit's S2: "S2 not received" signal
c) one or more types of signal requesting an increase in power output (coming from either an upstream or a downstream communications unit, because that respective unit is either not receiving an expected handshake signal or is receiving a suboptimal quality signal);
d) one or more types of signal requesting an increase in sensitivity of this unit's receiving apparatus (coming from either an upstream or a downstream communications unit, because that respective unit is either not receiving an expected handshake signal or is receiving a signal from this unit indicating receipt of suboptimal quality signals at this unit, or indicating absent [but expected signals] at this unit);
e) signals indicating that a high quality signal has been received at either the upstream or the downstream unit;
f) signals requesting user notification (These would be for a device which has such capability, e.g. a suitably configured SU, CPD, or WD);
g) signals carrying GPS information from either an upstream or a downstream unit;
h) signals carrying motion information from either an upstream or a downstream unit;
i) signals indicating decreased battery voltage in either an upstream or a downstream unit;
j) a routine S2 handshake signal from a downstream communication unit;
k) a signal indicating that the downstream communications unit is not receiving this unit's S1: "S1 not received" signal;
l) a signal representing the CCSI described hereinabove; and
m) a signal which causes a notification device to indicate to an IMD owner that his consent is requested for the acceptance/installation of an instruction/program for the IMD from the CS.

Figure 31A:
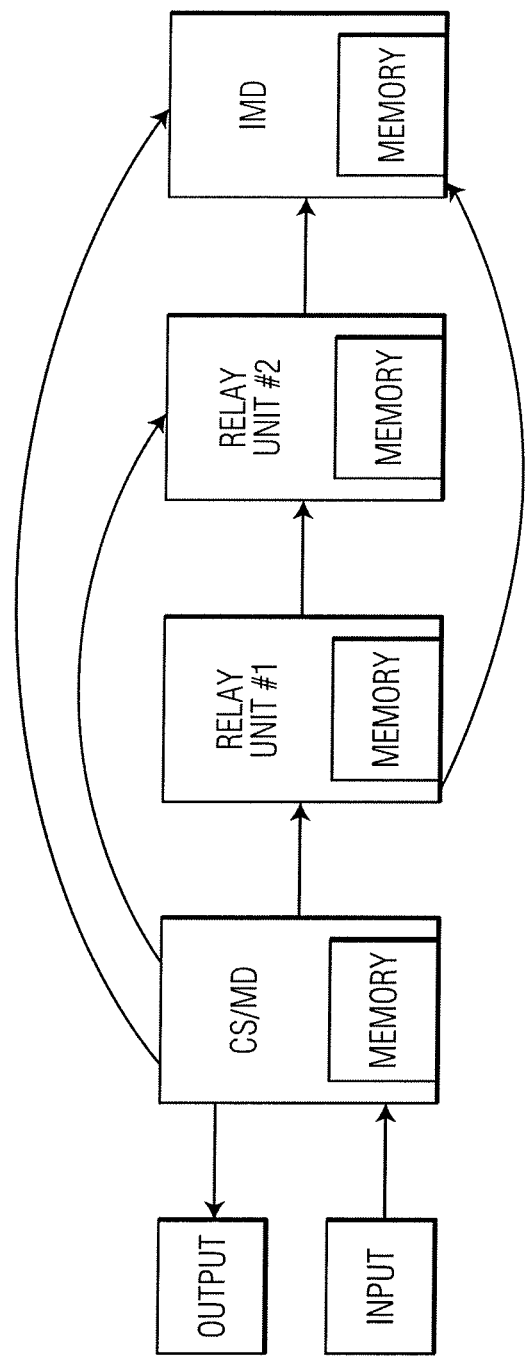
FIG. 31A is a block diagram showing a system of communication units with memory elements, for downstream transmission of instructions originating from a central station.
Figure 31B:
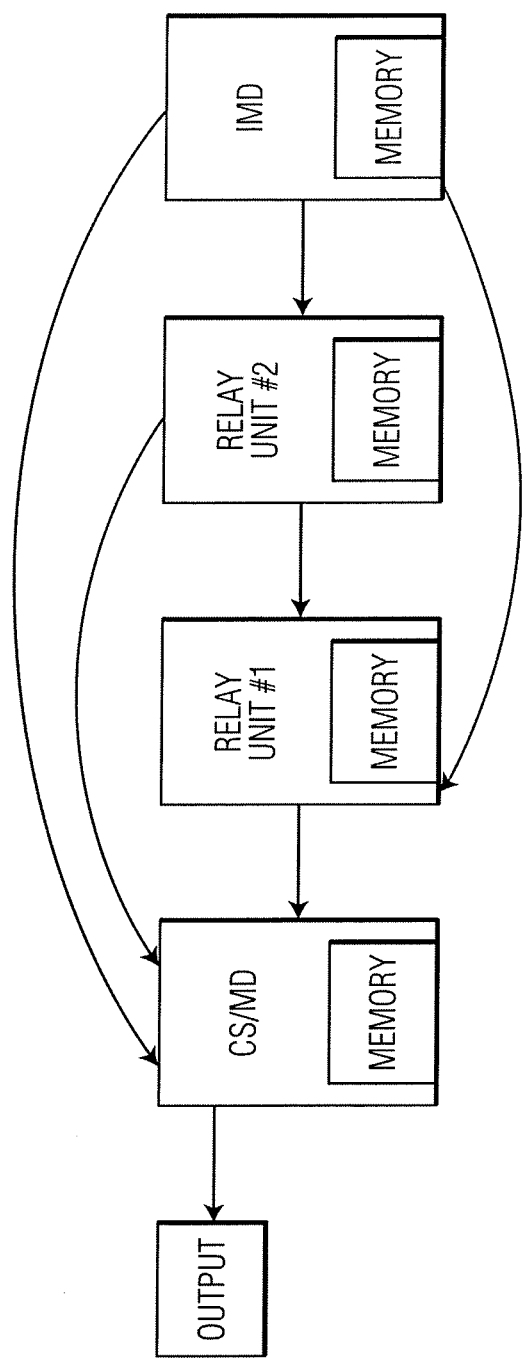
FIG. 31B is a block diagram showing a system of communication units with memory elements, for upstream transmission of a copy of instructions originating from a central station.
Figure 32:
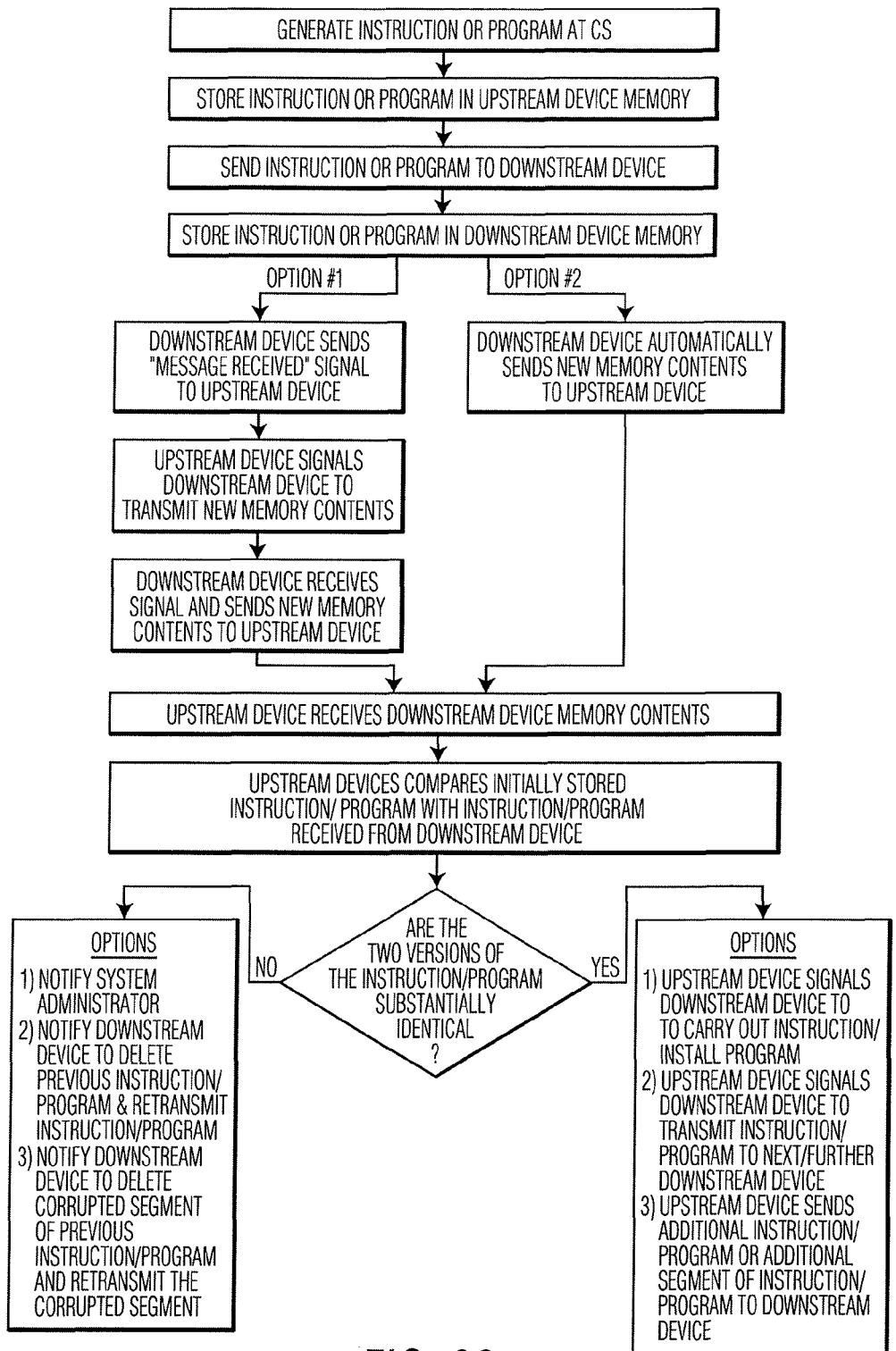
FIG. 32 is a flow diagram showing an algorithm for determining whether the instructions transmitted from a central station arrived at their downstream destination in an uncorrupted form.

FIGS. 31A, 31B and 32 show apparatus and methods for transmitting instructions from the CS to the IMD such that the sender can be certain that the instruction was received in non-corrupted form. Hereinabove and hereinbelow, "instruction" includes a software computer program, a program update or modification, a command or any signal which controls the functioning of the IMD.

The crux of these figures is that a copy of the instruction received downstream is transmitted upstream back to the sending source for comparison with the initially sent instruction. If the returned copy is the same as the initially transmitted one, it can be assumed that the instruction arrived at the point from which return occurred in un-corrupted form.

As shown in FIG. 31A (the downstream transmission) and FIG. 31B (the upstream return), the instruction may be
A) transmitted all the way from the CS/MD [central station and or medical doctor {i.e. a physician who desires to provide an instruction}] to the IMD, stored in a buffer memory, and then returned to the CS/MD, or
1) If the comparison indicates and uncorrupted transmission, the transmission task is complete and the instruction may be installed, enacted, etc.
2) If the comparison indicates a corrupted transmission
a) if one or more relay units were used in the transmission, request a return of one or more of those relay's memory, to attempt to determine the point of corruption; Once the point is identified, attempt to bypass that point in the transmission process;
b) if no relays were used, retransmit using one or more relays; or
B) transmitted only a portion of the route from CS/MD to the IMD, e.g. from the CS/MD to Relay Unit #1, and then returned to the CS/MD for comparison.
1) If the comparison indicates an un-corrupted transmission, options are
a) transmit the instruction from the memory of relay unit #1 to the next downstream unit (in the case shown in the figure, Relay Unit #2), then retransmit from Relay #2 to Relay #1 to confirm faithful transmission; Continue stepwise transmissions until the instruction reaches the IMD in un-corrupted form; or b) transmit the instruction from the CS/MD to the next downstream unit (in the case shown in the figure, Relay Unit #2), then retransmit from Relay #2 to CS/MD to confirm faithful transmission; Continue stepwise transmissions until the instruction reaches the IMD in un-corrupted form;

2) If any comparison indicates a corrupted transmission, attempt to bypass the unit responsible involved in the corrupted step. For example, if the return transmission from Relay Unit #1, when assessed at the CS/MD, does not match the initial instruction, attempt to bypass the potentially problematic unit; In this exemplary case, that would involve an attempted transmission from CS/MD to Relay Unit #2 directly (i.e. not via Relay Unit #1), or an attempted transmission from CS/MD to IMD.

FIG. 32 shows an algorithm for comparing the initial instruction sent downstream with its corresponding copy sent upstream for confirmation. Two approaches are shown:

a) one in which the copy is automatically sent upstream, upon receipt of a new instruction, and b) one in which the upstream reflected copy of the instruction is only sent if, after receiving a signal that the instruction was received downstream, the upstream unit requests the copy.

Options if the upstream unit determines that the copy that it has received is correct include:
 a) if it is confirmed that the proper instruction has arrived at the IMD, instructing the
    IMD to install/enact the instruction;
 b) commanding the downstream unit which has properly received the instruction to
    forward the instruction on to the next downstream unit; and
 c) sending an additional instruction.

Options if the upstream unit determines that the copy that it has received is not correct include:
 a) notifying the system administrator;
 b) command the downstream unit to delete the previous instruction from its memory, and then re-transmit the instruction; and
 c) command the downstream unit to delete the corrupted segment of the previous instruction from its memory, and then re-transmit that segment.

Although the aforementioned discussion pertains to the verification of instructions transmitted downstream, it could also be used to verify the proper transmission of information in the upstream direction. Such upstream information could include a) patient data, b) confirmations of executed commands, and c) device self monitoring data. In the case of data, for example, data could be 1) stored in the IMD, 2) transmitted from the IMD to the CS; 3) re-transmitted from the CS to the IMD; 4) at the IMD, the data that was re-transmitted from the CS would be compared with the data which was initially transmitted from the IMD.

Other methods and apparatus for confirmation of un-corrupted distant receipt of a signal set are known in the art.

Figure 33:
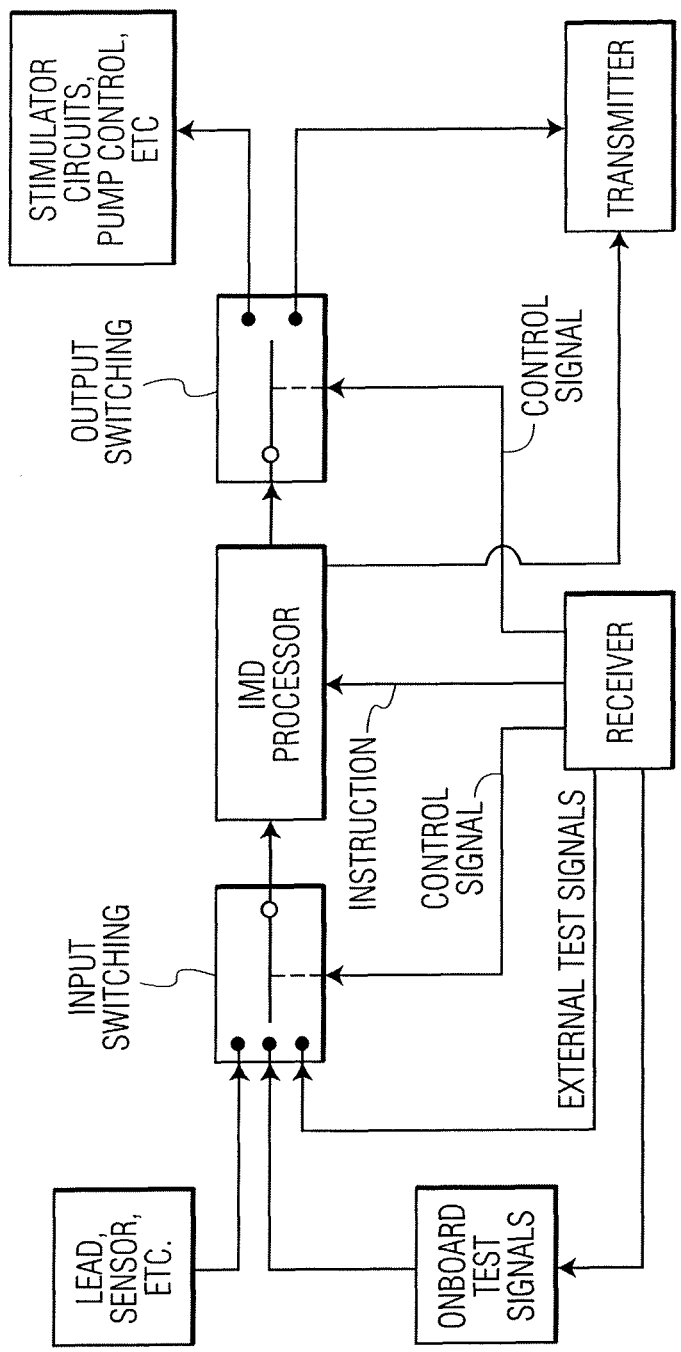
FIG. 33 is a block diagram of an IMD in which the receipt of new operating instructions can be tested by running mock scenarios.

An alternative way of determining if certain types of instruction were properly delivered from the CS to the IMD is a functional evaluation of the IMD post instruction delivery. FIG. 33 shows an apparatus and method for such a functional evaluation entailing:

1) the temporary disconnection of the IMD processor input from the IMD sensors outputs, and the substitution of test signals as processor inputs; and 2) the temporary disconnection of the input to either the IMD actuator circuits or the disconnection of the input to a more proximal point in the actuation process (i.e. a point after a therapy decision is made but before it is executed).

If the IMD is an ICD, examples of actuator circuits are circuits which supply the energy for cardiac pacing and defibrillation; and examples of more proximal points in the actuation process are circuits which activate the aforesaid energy supply circuits.

The test signals would reflect various scenarios that would, following the installation/enactment of a new instruction, result in an IMD action which differs from the expected action prior to the installation/enactment of the new instruction. Among the instructions which could be functionally evaluated are a) reprogramming of already existing software; and b) new software with different operating characteristics than the previous software, c) an improved software version which does not contain an error which was present in a previous version, and d) a patch for an already installed software version which contained an error.

For example: If the IMD is an ICD, a simple example is reprogramming the rate cutoff for detection of VT. Consider an instruction which reprograms the VT rate cutoff from 190 beats per minute ("BPM") to 200 BPM. The test procedure could involve:
 a) changing the output so that the response to a test signal is not delivered to the patient; In the case of the ICD, it would mean that either (i) once VT is detected, neither anti-tachycardia pacing ("ATP") nor shock is triggered, or (ii) ATP or shock is delivered to a dummy load;
 b) changing the processor input source from the ventricular sensing lead to the source of electrogram test signals [which could be a) transmitted from the CS, or b) from an internal test generator within the ICD];
 c) supplying the electrogram test signals [e.g. (i) supplying electrograms which simulate a heart rate of 199 BPM, with non-detection of VT being the expected response; and (ii) supplying electrograms which simulate a heart rate of 201 BPM, with detection of VT being the expected response];
 d) observing the response to the test signals
 e) at the completion of the test, changing the processor input source back to the ventricular sensing lead and restoring output routing so that ATP or shock is delivered to the patient.

Another example: replacing the electrogram analysis software with a more robust analysis package. The package could be one which more accurately discriminates between ventricular tachycardia and supraventricular tachycardia. The test procedure could involve: involve:
 a) changing the output so that the response to a test signal is not delivered to the patient;
 b) changing the processor input source from the ventricular sensing lead to the source of electrogram test signals;
 c) supplying the electrogram test signals (e.g. test signals designed/selected to determine if the new software properly distinguishes between VT and SVT);
 d) observing the response to the test signals
 e) at the completion of the test, changing the processor input source back to the ventricular sensing lead and restoring output routing so that ATP or shock is delivered to the patient.

Observing the response to the test signals (and thus determining if the new instruction resulted in the desired IMD performance) may involve (a) transmitting a copy or a representation of the processor output, (b) transmitting a copy or representation of the input to an actuator circuit, as defined hereinabove; (c) interrogating the IMD following the test procedure; or (d) combinations of (a)-(c). By analysis of this copy or representation, a remote person may determine if the new instruction a) has been properly received by the IMD; and b) whether the new instruction allows the IMD to function in the intended manner; and c) whether the new instruction compromises the functioning of any other IMD tasks (Examples would be (i) new software improves the sensitivity of VT detection but decreases the specificity of VT detection in an ICD; and (ii) new software compromises the functioning of the IMD by impairing the operation of another IMD program or a segment of another IMD program.)

Figure 34:
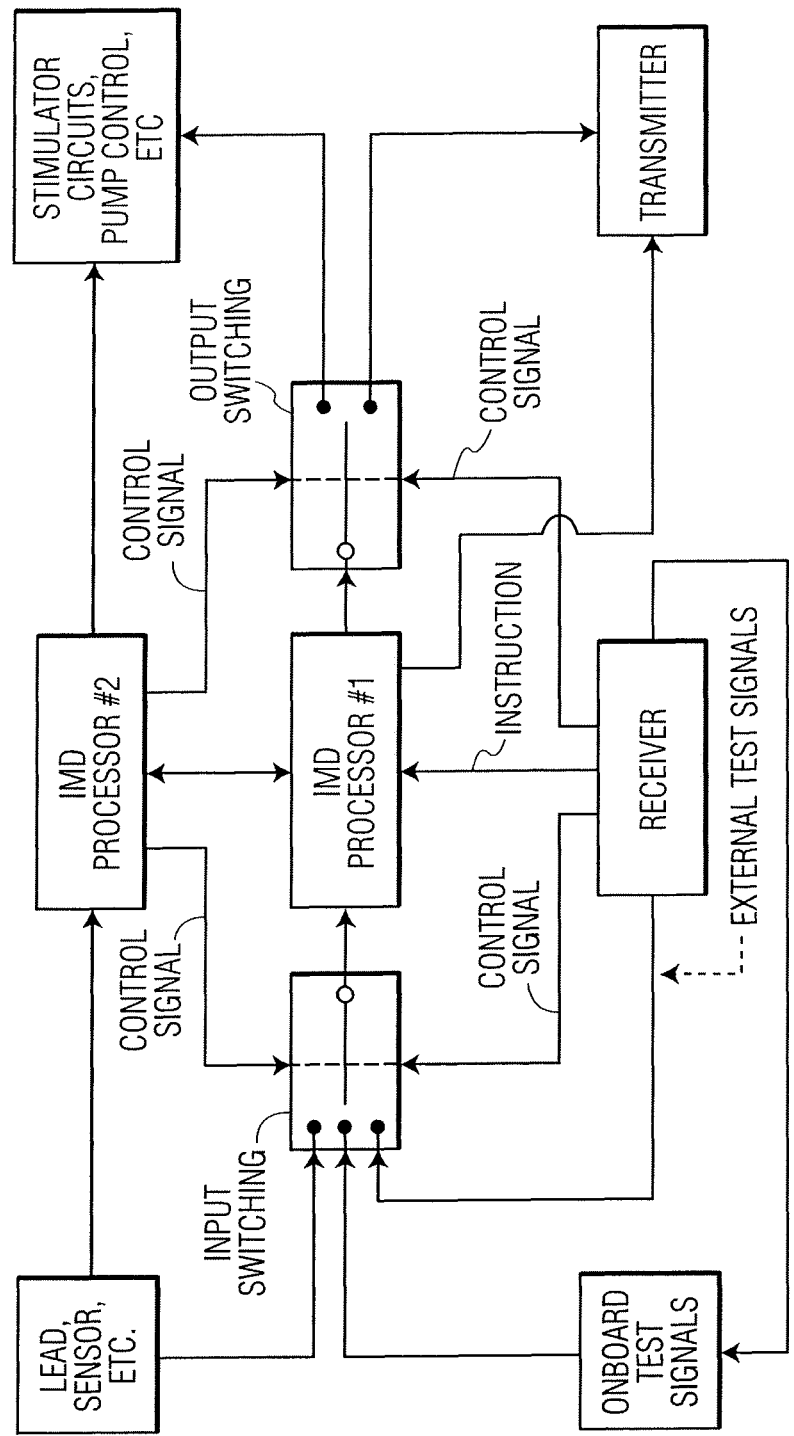
FIG. 34 is a block diagram of another embodiment of an IMD in which the receipt of new operating instructions can be tested by running mock scenarios.

In a preferred embodiment of the invention, the IMD would be capable of responding to a situation requiring the need for immediate therapy, if such situation occurs during the test procedure. This feature may be accomplished, as is shown in FIG. 34, by having two processors which operates in parallel: Processor #2—which does not initially receive the new instruction, and Processor #1—which does receive the new instruction. During the testing of Processor #1 after it has received the new instruction, Processor #2 (which runs the old, not the new instruction) continues to monitor the patient. If Processor #2 indicates the need for immediate therapy, then Processor #2 may:

a) itself directly activate the IMD actuator circuit; or b) restore the input of the IMD actuator circuit to the output of Processor #1. In this case, it may (i) also switch the input of Processor #1 back to the real time signals from the IMD lead/sensor, etc.;

(ii) provide Processor #1 with a copy of the signal(s) which triggered the interruption of the test procedure, such signals having been stored in memory; or (iii) (iii) perform both (i) and (ii).

Following the completion of therapy for the event which required immediate attention, the test procedure is completed. Following the completion of the test procedure, if it indicates the updated version of Processor #1 is functioning in a desirable way, Processor #2 may be updated with the new instruction.

For example, if VT requiring therapy occurs during a test of new VT detection software for Processor #1, the VT is detected by Processor #2. Processor #2 may then itself directly activate the IMD actuator, or may cause Processor #1 to evaluate the VT, after which Processor #1 would determine the response to the VT.

The aforementioned IMD test apparatus and methods may also be used to evaluate IMD performance even if no new instruction was delivered. This may be done:

a) as part of periodic IMD maintenance by the IMD;

b) as part of periodic IMD maintenance by a remote source;

c) in the event that there is a question (on a non-periodic basis) about whether the IMD will perform properly, such question based on:

(i) a determination that the aging process [e.g. of the battery, the sensor(s), etc.] may negatively impact IMD performance;

(ii) the IMD manufacturer or other authority having become aware that certain clinical scenarios do not result in optimum IMD performance; and/or (iii) other considerations.

IMD Security Issues:

Encryption/Decryption

In order to minimize the chance that an unauthorized person could gain access to a patient's IMD, the techniques illustrated in FIGS. 35A to 39, and others known in the art may be employed.

Figure 35A:
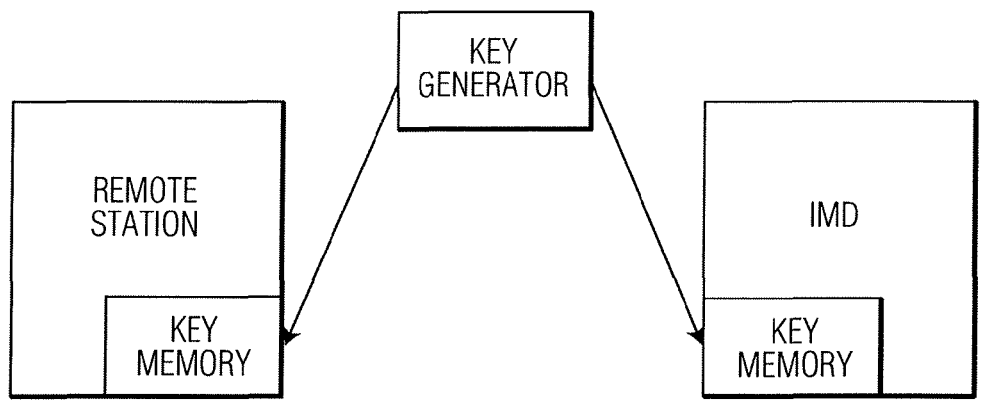
FIGS. 35A, 35B and 35C are block diagrams showing the setting up of encryption and decryption keys for the IMD and for the unit which communicates with the IMD.
Figure 35B:
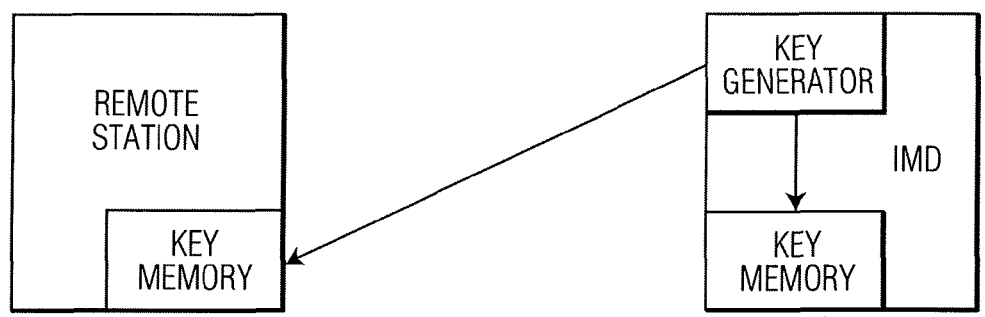
Figure 35C:
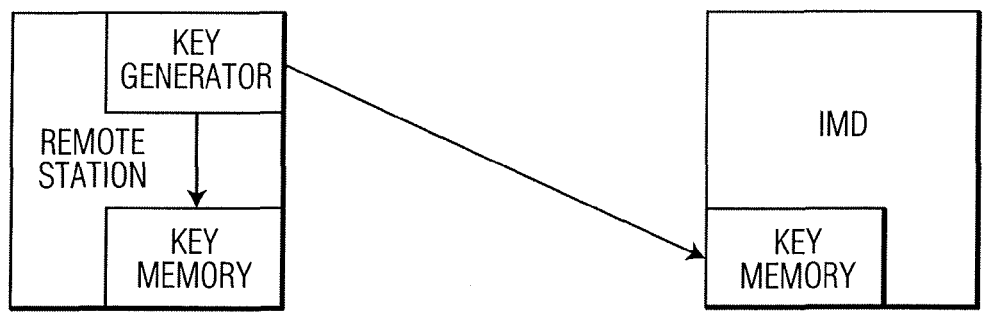

FIGS. 35A to 35C illustrate the deployment of an encryption/decryption key which may be stored in the IMD and in an approved remote station, which will, at later times be allowed to communicate with the IMD. The key is used to encrypt information which is sent from the IMD to the remote station and to decrypt it upon its arrival at the remote station. The same, a similar or an entirely different key may be used to transmit instructions/commands/programs from the remote station to the IMD. The remote station may be a central station as is described in U.S. Pat. No. 7,277,752, a peripheral station as is described in U.S. patent application Ser. No. 11/502,484, a central station which handles a variety of IMDs, a central station which handles both implanted and external medical devices, or a physician's office.

The appropriate key is stored in the memory of the remote station and of the IMD. The memory may be a write once only type, or a re-writeable type. As used hereinabove and hereinbelow, the term "key" is intended to include systems and methods of encryption at the sending end of a communication link, and decryption at the receiving end, as well as methods of password protection.

The key may be generated at the time the device is manufactured. In a preferred embodiment of the invention, the key would be generated at the time that the device is implanted. Since the identity of either a controlling physician or central station might then be known, a single corresponding key could then be generated and stored in the appropriate remote station. FIG. 35A shows an embodiment of the invention in which the encryption/decryption key or keys are generated by a freestanding device which is not part of either the IMD or the remote station. The information is entered into the IMD by techniques know in the art. The corresponding copy for the remote station a) may be transmitted to the remote station at substantially the same time as it is entered into the IMD, b) may be transmitted to the remote station at a later time, or c) may be stored on a portable memory device, to be transported to the remote station. Embodiments of the invention with one or more additional copies of the key are possible. In a preferred embodiment of the invention, once the appropriate number of key copies is generated, the key is not stored in the key generator.

FIG. 35B shows an embodiment of the invention in which the encryption/decryption key or keys are generated by circuitry which is part of the IMD. The corresponding copy for the remote station a) may be transmitted to the remote station at substantially the same time as the IMD is planted, b) may be transmitted to the remote station at a later time, or c) may be stored on a portable memory device at the time of device implantation or at a later time, to be transported to the remote station. In the setup shown in FIG. 35B, to restrict access to the encryption/decryption information in the IMD, copying of it may be a) restricted to a once only basis, b) restricted to a specific window in time (e.g. the time of IMD implantation), c) password protected, or d) protected by methods which are combinations of a) through c) listed immediately hereinabove.

FIG. 35C shows an embodiment of the invention in which the encryption/decryption key or keys are generated by circuitry which is part of the remote station. The corresponding copy for the IMD a) may be transmitted to the IMD at substantially the same time as the IMD is planted, b) may be transmitted to the IMD at a later time, or c) may be stored on a portable memory device at the time of its generation at the remote station, to be transported to the IMD for entry either at the time of IMD implantation or later. In the setup shown in FIG. 35C, to restrict access to the encryption/decryption information in the remote station, copying of it may be a) restricted to a once only basis, b) restricted to the a specific window in time, c) password protected, or d) protected by methods which are combinations of a) through c) listed immediately hereinabove.

FIG. 36 shows an array of portable memory units referred to hereinabove, each used for transporting an encryption/decryption key from an implant site to a remote station, for storing it in the remote station and for encryption/decryption at the time of communication between a remote station and a particular IMD. The array forms a memory bank in a remote station communication device, allowing the remote station operator to communicate with each of a number of different IMDs. In one preferred embodiment of the invention, the portable memory units are write-once only; In another (or the same) preferred embodiment of the invention, these memory units may not be read or duplicated, though they are used for encryption/decryption. By not allowing for either duplication or for transmitting the key, an additional security measure is obtained.

Figure 37:
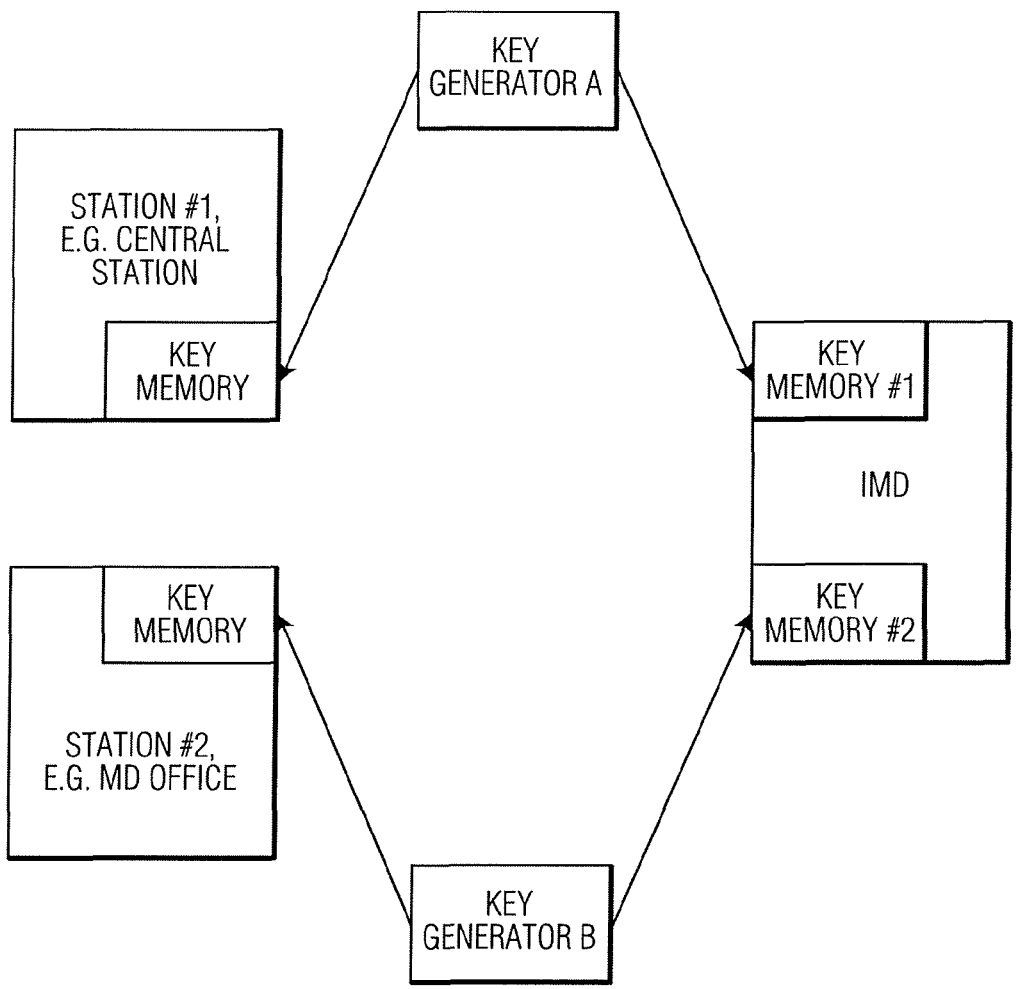
FIG. 37 is a block diagram showing a system with two different encryption/decryption keys, one for each source of possible IMD remote instruction generation.

FIG. 37 shows a system with two key generators, one for IMD-Station #1 communications, and one for IMD-Station #2 communications. Stations #1 and #2 could be any two different stations from which communicate with the IMD; For example, Station #1 could be a central station for management of IMDs and Station #2 could be the IMD owner's physician's office. As shown in the figure, the two key generators are free standing, analogous to FIG. 35A. However, either one of the generators (or both) could be part of the IMD (analogous to FIG. 35B), or either one of the generators (or both) could be part of the respective remote station (analogous to FIG. 35C).

Figure 38A:
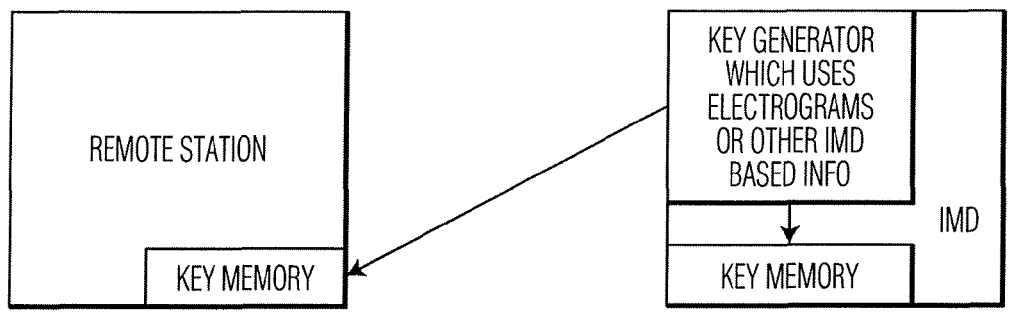
FIGS. 38A and 38B are block diagrams showing two types of apparatus for the generation of an encryption/decryption key based on patient data.

FIG. 38A shows an encryption method which uses a digitized form of an item of patient data obtained by the IMD during the previous IMD-Remote Station session in the generation of the key to be used in the current session. By so doing, a) the key changes from session to session, and b) only the remote station which participated in the previous session can participate in the next session. This approach may be used to change the key during a session, as well. In FIG. 38A, the key for the next session is generated at the IMD and is transmitted to the remote station.

Figure 38B:
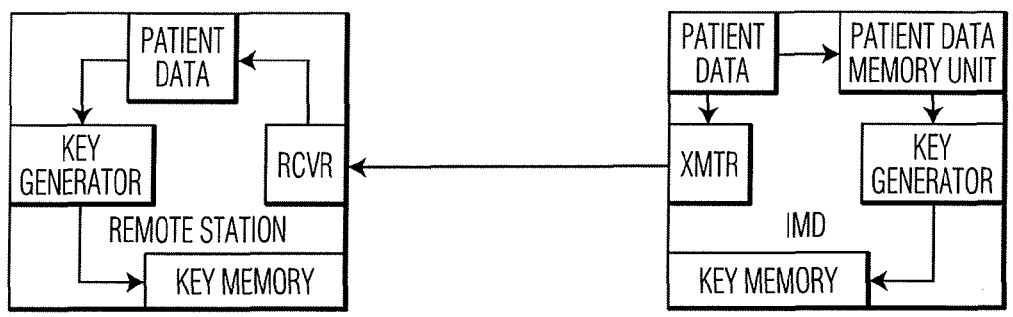

FIG. 38B shows a variation in which, the patient data on which the key is based is generated at the IMD and is transmitted to the remote station (rather than the approach of FIG. 38A in which the key itself is transmitted). The patient data is used to generate the key for the next remote station-IMD communication, using a key generator in the remote station whose function is identical to that of the key generator within the IMD (i.e. for a specific set of patient data, both the remote station key generator and the IMD key generator will generate a matching set of encryption/decryption keys).

Figure 39:
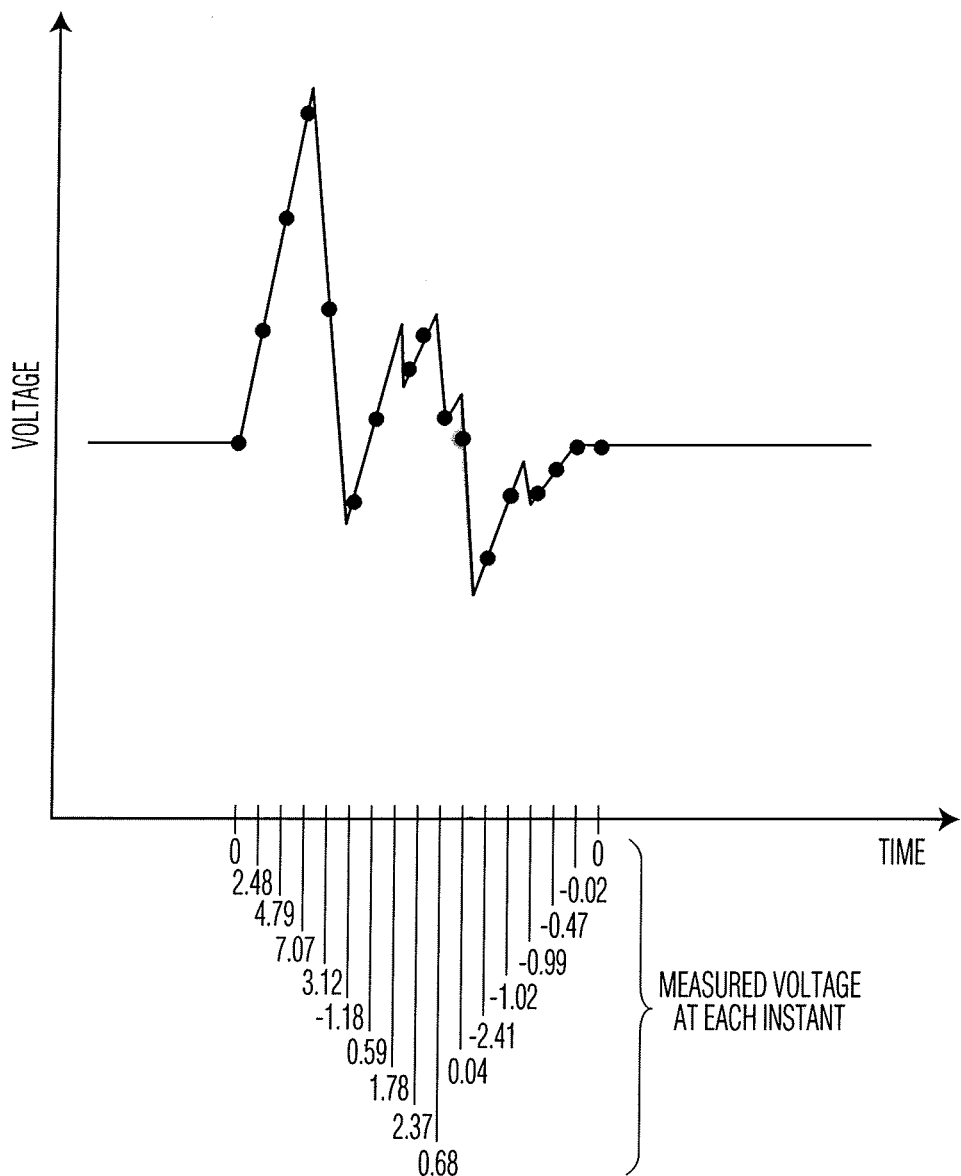
FIG. 39 is a graphical representation of a cardiac electrogram, the time dependent voltage of which is used to generate an encryption/decryption key.

FIG. 39 shows an example of a digitized electrogram signal. The measured voltage is used to generate a series of numbers which can be used to generate a new encryption/decryption key. The waveform may be sampled more frequently or less frequently. The data may be digitized on a 16 bit scale, a 32 bit scale or with any arbitrary degree of accuracy. The digitized data may be transformed in any of a variety of ways, as is known in the art.

An example of such patient data would be a waveform in a patient electrogram, or intervals between patient heartbeats, determined by an ICD. In the figure, the key generator within the IMD updates both the IMD memory and the memory of the remote station with a new key, either at the end of each session, or during a session.

IMD Owner's Permission to Access IMD

During certain scenarios, it may be impractical or undesirable to require the IMD owner's permission. For example, if the IMD is an ICD which is repeatedly shocking the owner for atrial fibrillation, and the owner is physically incapable of granting permission, it would be desirable to reprogram or inhibit the device without permission.

If, on the other hand, an elective reprogramming of the IMD is desirable, or if the download of new software is desirable, the permission of the IMD may be sought. Requiring such permission makes it less likely that an unauthorized person could gain access to the IMD.

Figure 40:
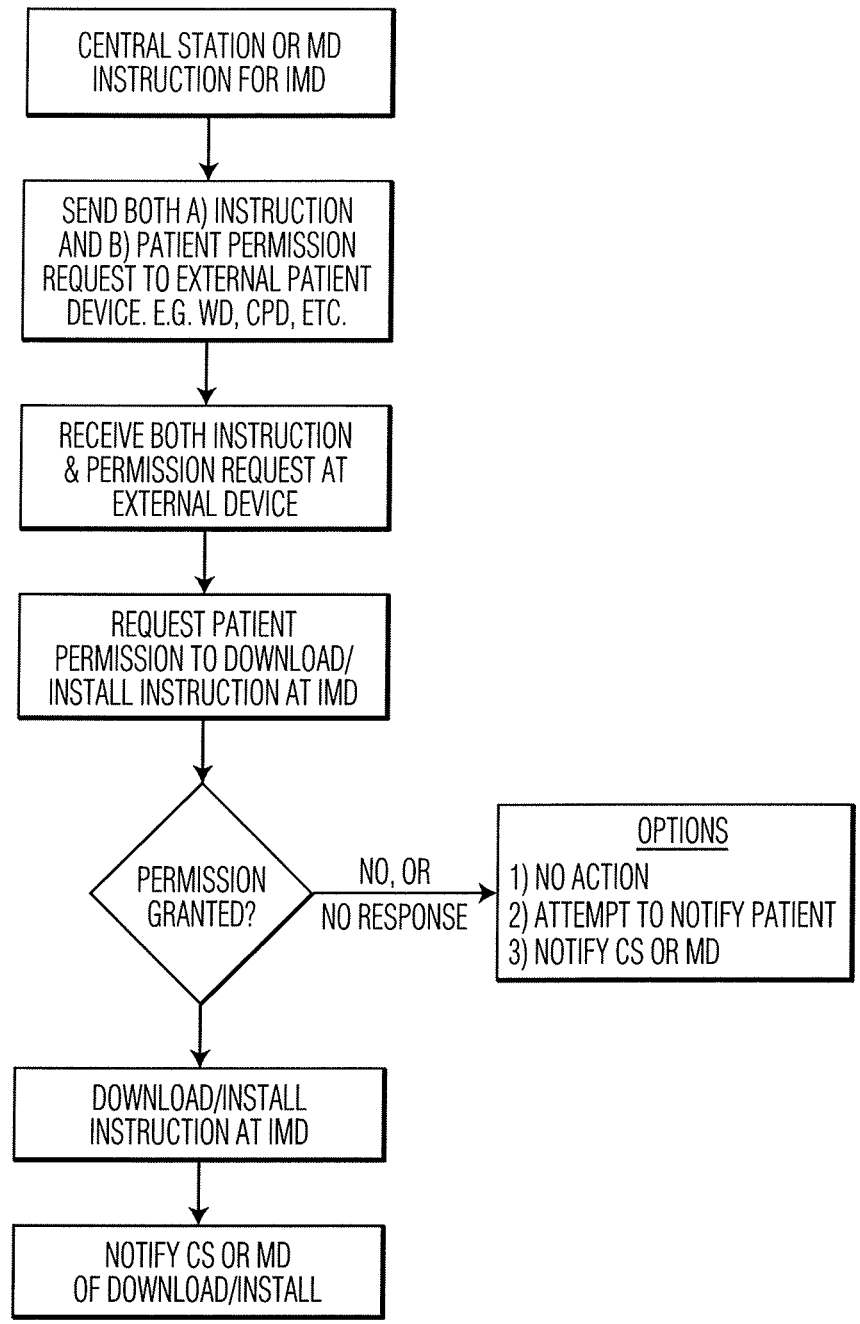
FIG. 40 is a flow diagram illustrating a method by which the IMD owner may grant permission to download/install an instruction, program or command to an IMD.
Figure 41:
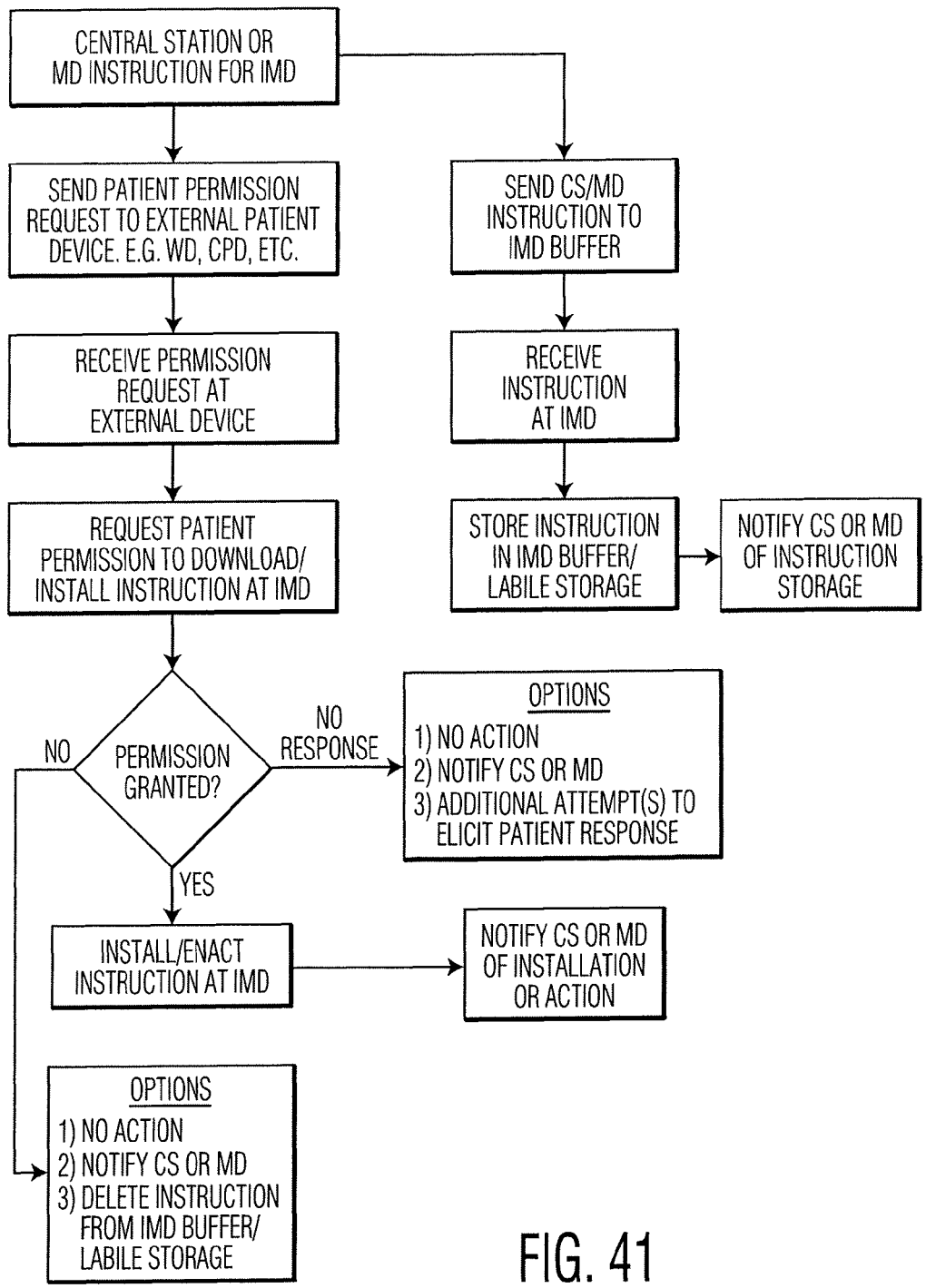
FIG. 41 is another flow diagram illustrating a method by which the IMD owner may grant permission to download/install an instruction, program or command to an IMD.
Figure 42:
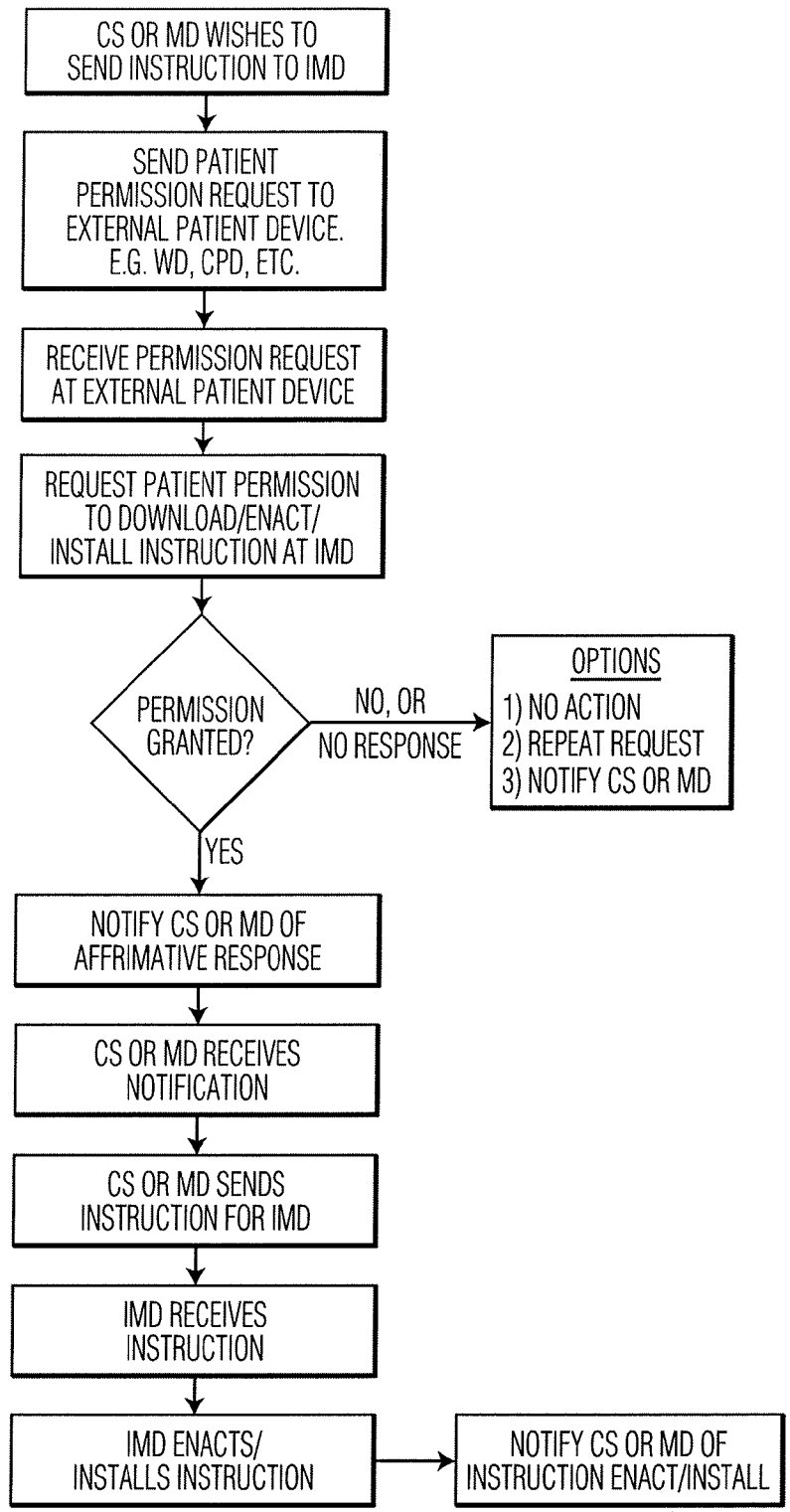
FIG. 42 is yet another flow diagram illustrating a method by which the IMD owner may grant permission to download/install an instruction, program or command to an IMD.

FIGS. 40, 41 and 42 show flow diagrams of three possible methods of permission granting.

In FIG. 40, both the instruction/program/command for the IMD and a patient permission request are sent to an external device such as the CPD or WD. The external device notifies the patient of a permission request. The notification may be a telephone message, a tone indicating that a message is to be retrieved, etc. The message may state a) the source, b) the content/purpose of the instruction/program/command, c) a contact person/phone number that the IMD owner may communicate with to receive additional information, the level of urgency of the requested download (e.g. low urgency for software update; high urgency for arrhythmia in progress). If the IMD owner grants permission (e.g. by pressing a key or sequence of keys on the CPD), the IMD instruction is downloaded from the CPD or WD to the IMD and is installed/enacted. Three options are listed in the figure in the event of either a) no response, or b) a negative response.

In the approach shown in FIG. 41: a) the instruction is sent to a buffer or labile memory of the IMD and b) permission to install/enact is sent to the IMD owner via the WD or CPD. If the owner grants permission, he so indicates via the WD or CPD, which signals the IMD to install/enact the instruction stored in its buffer/labile memory. If permission is not granted, three options are listed in the figure including the possibility of deleting the instruction from the buffer/labile memory.

In the approach shown in FIG. 42, the initial action by the person desiring to issue an IMD instruction is only to send a permission request to the IMD owner. If permission is granted, then the IMD instruction is sent to the IMD, and confirmation of installation or of enacting the instruction is sent back to the CS or MD who sent the instruction.

Formats for outside access to an IMD in relationship to IMD owner permission include:

1) Under all circumstances, no outside access without IMD-owner permission;

2) IMD access without requesting permission in the event of an emergency, emergency defined in advance, and IMD owner, in advance, grants emergency access rights [to one or more individuals or centers or to all centers or individuals];

3) IMD access without requesting permission if
   (a) emergency in progress;
   (b) person obtaining access knows one or more passwords and/or one or more encryption keys; or
   (c) both (a) and (b)

4) IMD access under all circumstances, if in judgment of medical professional access is warranted.

Figure 43:
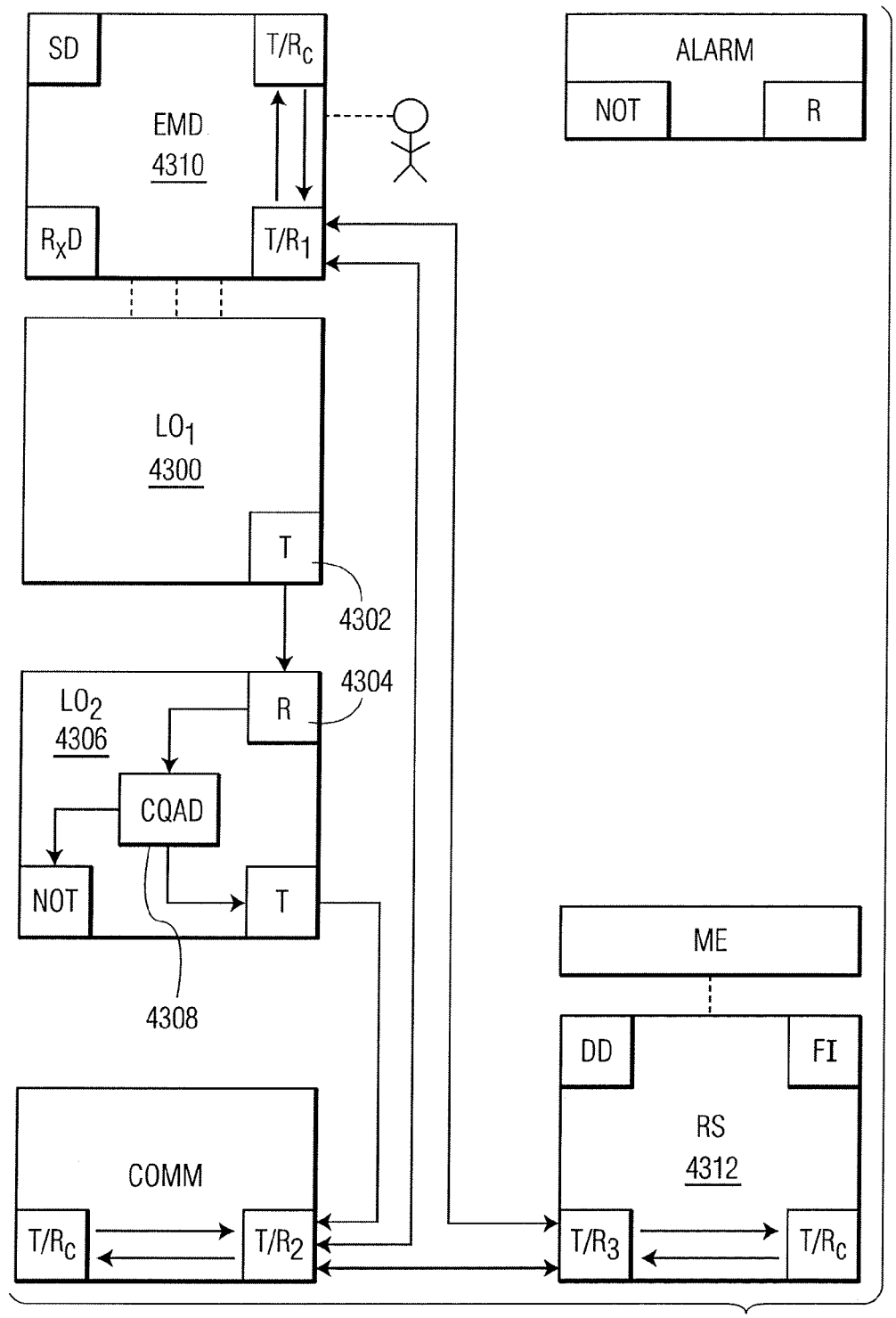
FIG. 43 is a block diagram illustrating a medical device system with locator units, with one type of locator configuration.

FIG. 43 shows a block diagram of one type of locator system. The aim of the locator system is to establish with a great degree of certainty where a patient with an implanted device is located, without using the battery of the implanted device. The purpose of locating the patient is to optimize communication between a remote station and the device with a high degree of certainty, for as great a fraction of the time as possible. The first locator is either attached to an implanted unit, is implanted in the patient, unattached to the unit, or is outside of the patient's body, but designed to be either worn or in reliably close proximity to the patient.

A first locator unit 4300 contains transmitter 4302 which emits locator signals for detection by a receiver 4304 in the second locator unit 4306. The presence and quality of the signals from 4302 are evaluated by assessment device 4308, and the assessment may be shared with other units in the system. The information may be used for (a) modifying the path and entities which communicate, (b) modifying the communication parameters (e.g. power output, sensitivity, signal compression, transmission rate, etc) of one or more of the communicating units, (c) producing an alarm or other means of notifying either a patient, a user of the medical device, a person who can contact the patient or someone in proximity to the patient. The goal is to optimize communications between the medical device 4310 and the remote station 4312.

Figure 44:
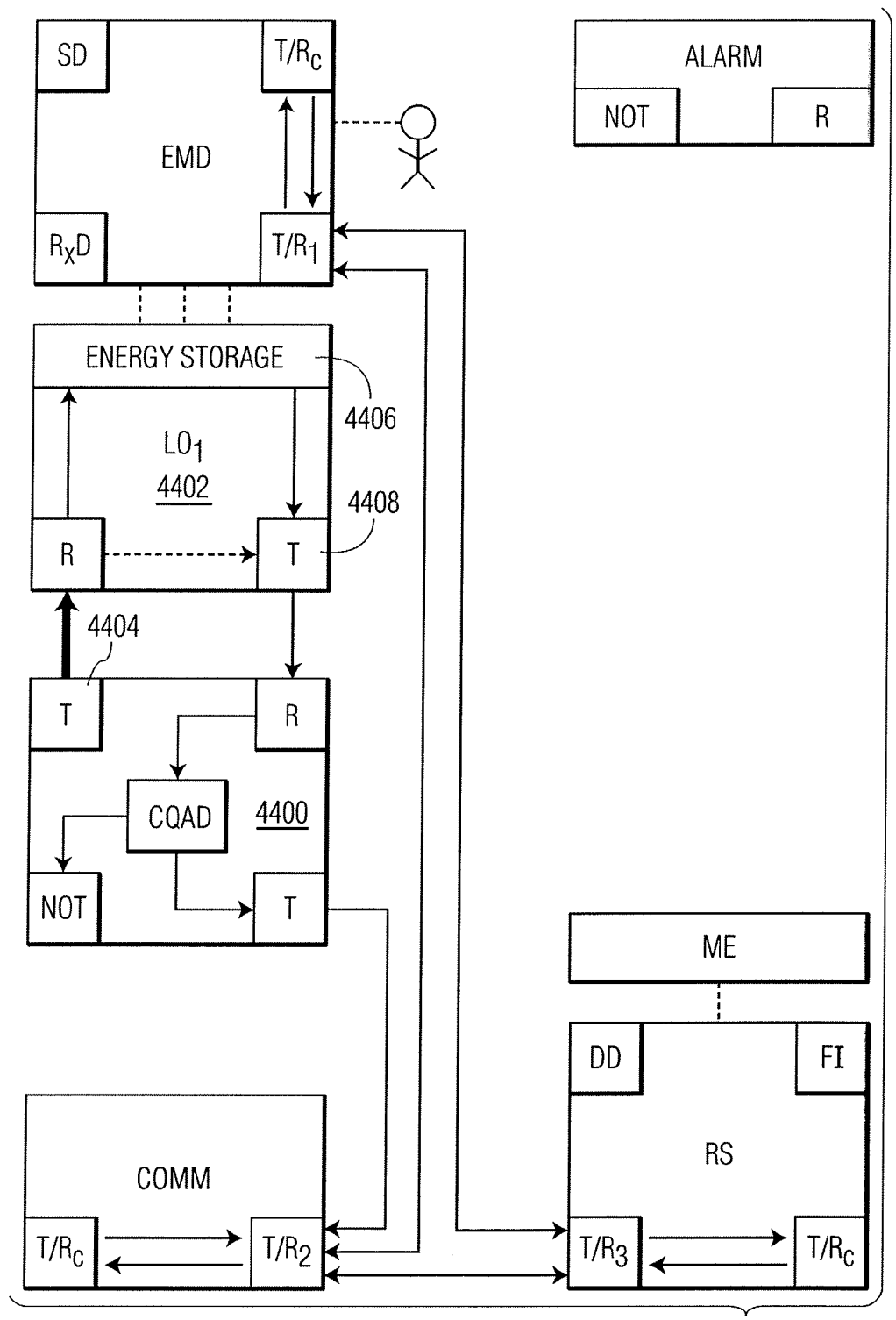
FIG. 44 is a block diagram illustrating a medical device system with locator units, with a second type of locator configuration.
Figure 45:
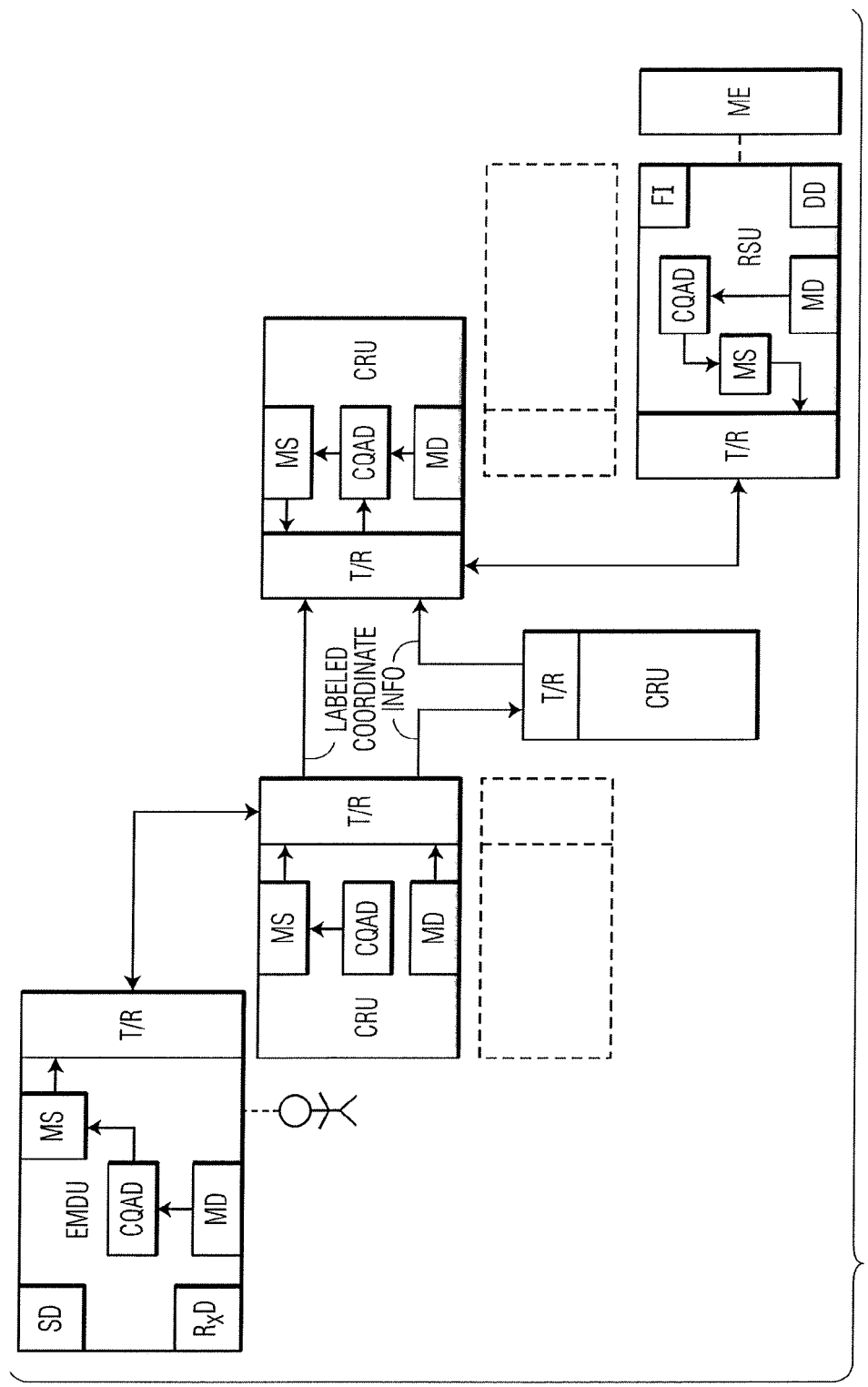
FIG. 45 is a block diagram of a medical device system with communication units which detect changes in spatial position, illustrating the propagation of coordinate information pertaining to such units.
Figure 46:
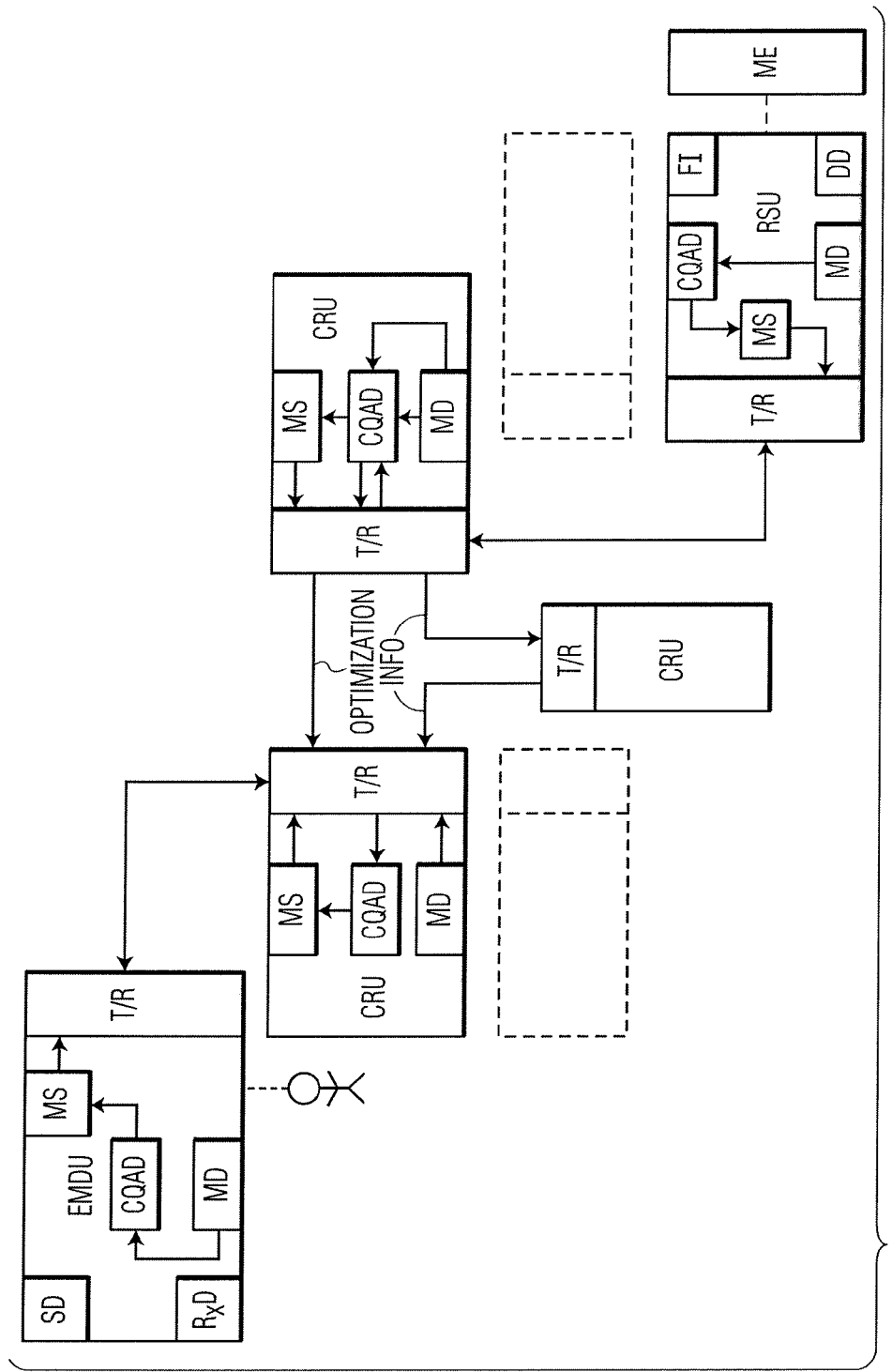
FIG. 46 is a block diagram of a medical device system with communication units which detect changes in spatial position, illustrating the propagation of communication optimization information pertaining to such units.

FIG. 44 shows a block diagram of a second type of locator system. The first locator in this system 4402 is designed not to require a battery, though it may use a backup one. It derives its energy from the transmitter 4404 of the second locator unit 4400. The energy is stored in storage device 4406 which may be a capacitor, a battery, or other energy storage device as is known in the art. The stored energy is used to power first locator transmitter 4408. FIGS. 45 and 46 show the architecture of a communication system which links a remote station with an electronic medical device via one or more relay units. The relay units may be stationary or mobile. The system shown in FIGS. 45 and 46 uses motion detecting apparatus in one or more of the relay units, electronic medical device and remote station to (a) generate location information for the units (FIG. 45) and to generate communication optimization information (FIG. 46).

Figure 47:
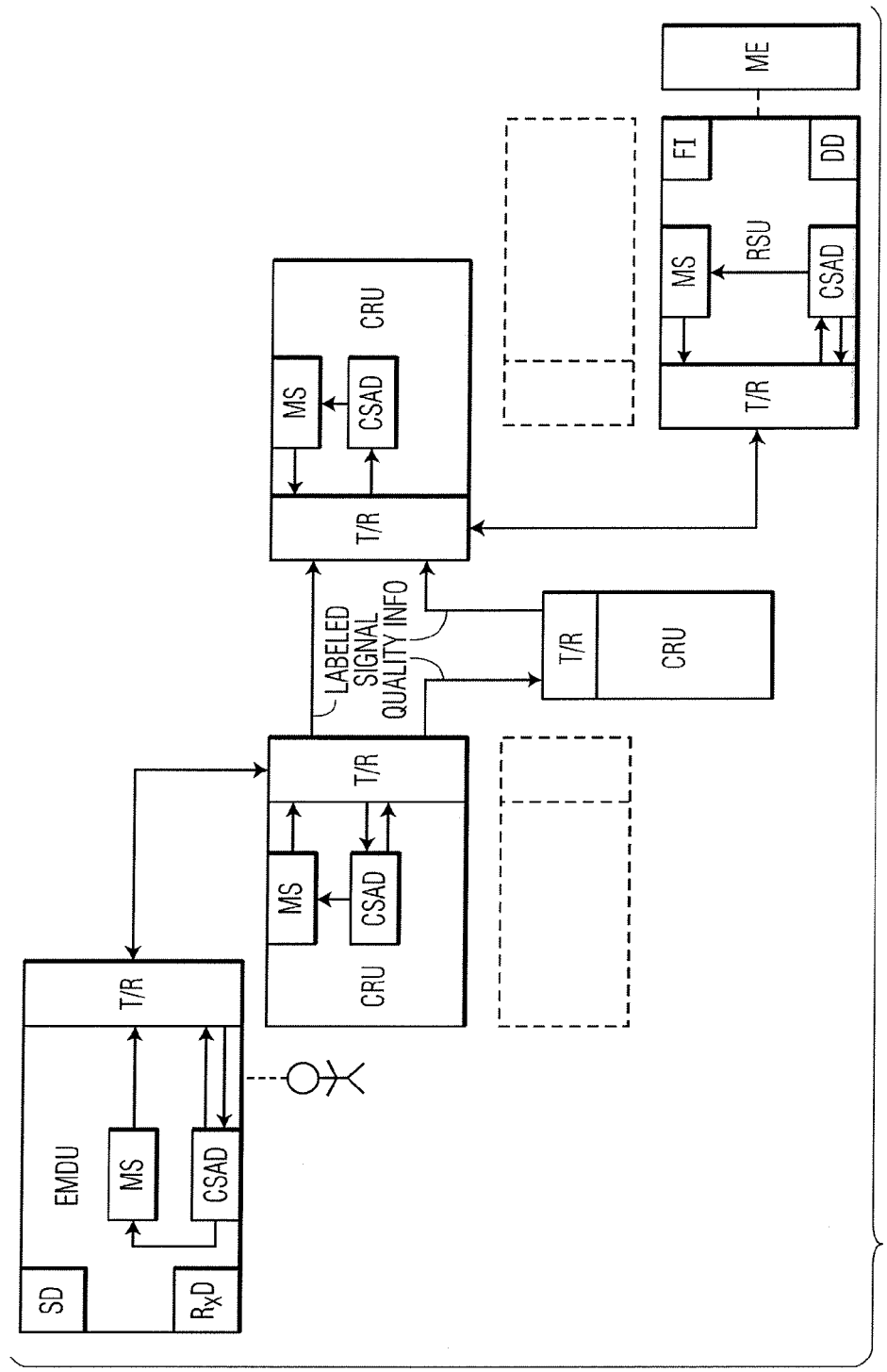
FIG. 47 is a block diagram of a medical device system with communication units which detect changes in signal quality, illustrating the propagation of signal quality information pertaining to such units.
Figure 48:
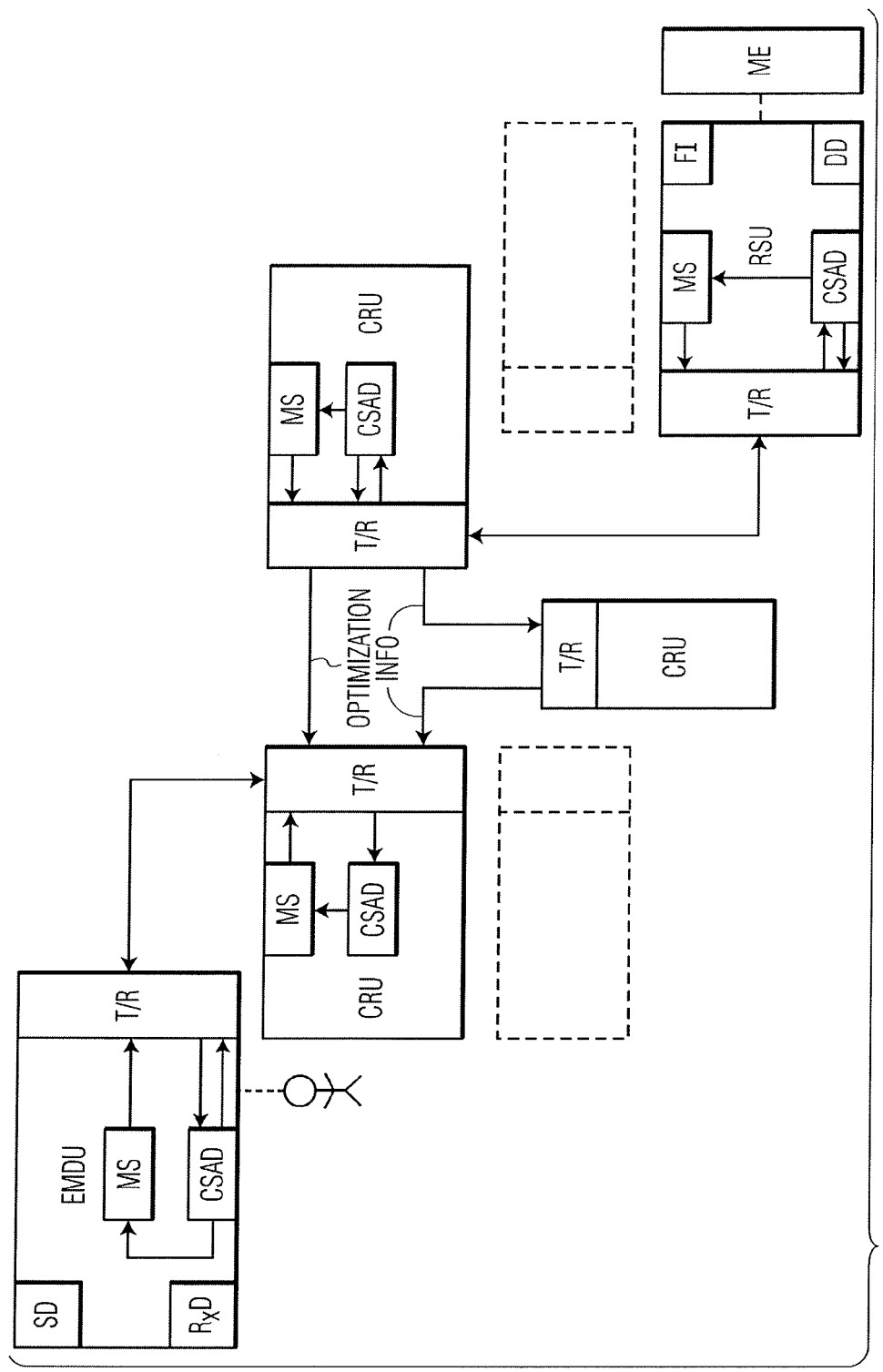
FIG. 48 is a block diagram of a medical device system with communication units which detect changes in signal quality, illustrating the propagation of communication optimization information pertaining to such units.

FIGS. 47 and 48 show another architecture of a communication system which links a remote station with an electronic medical device via one or more relay units. The relay units may be stationary or mobile. The system shown in FIGS. 47 and 48 uses the analysis of signal strength in one or more of the relay units, electronic medical device and remote station to generate communication optimization information, based on the strength and quality of received signals.

System architectures which use both signal strength and the detection of motion are possible, and various configurations will be determinable to those skilled in the art.

Figure 49:
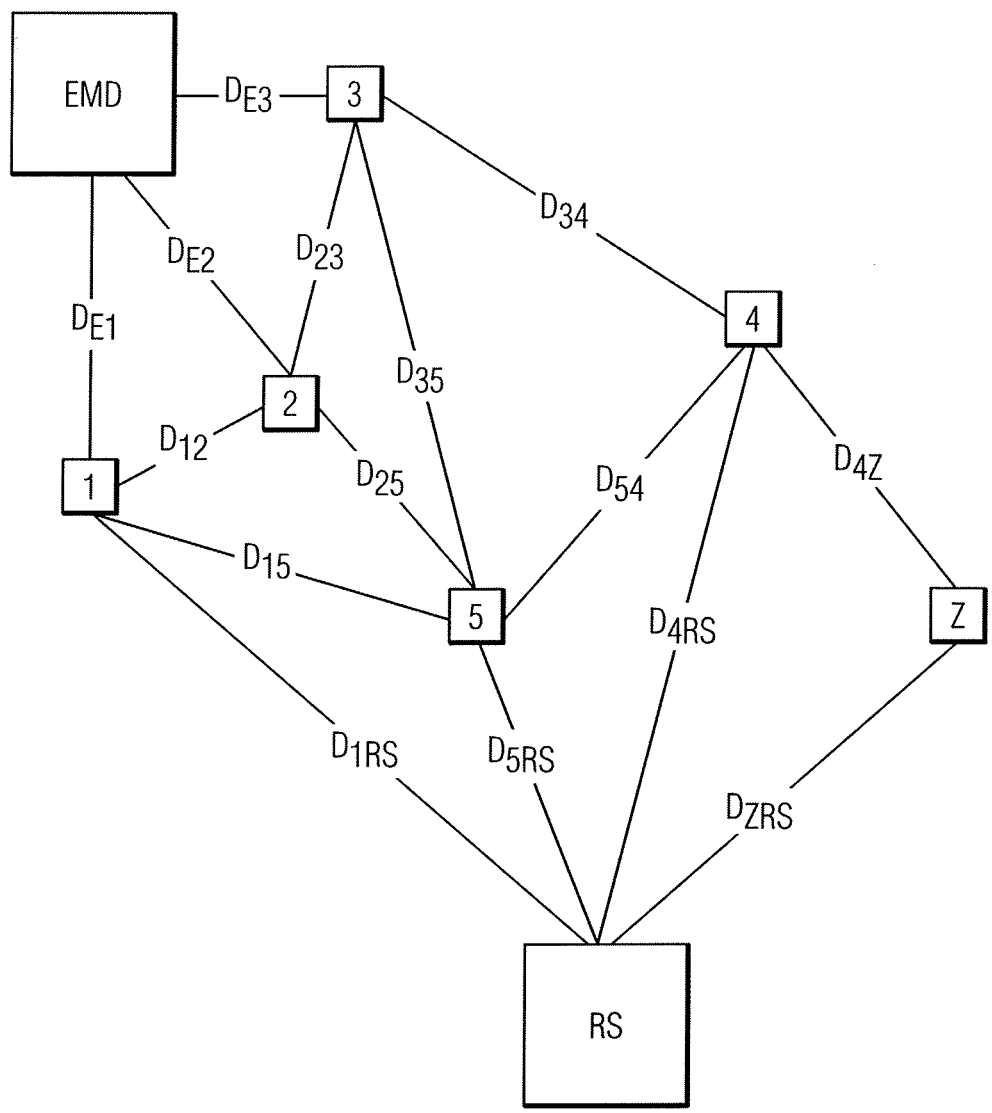
FIG. 49 is a block diagram illustrating the determination of an optimal communication route by a local or master communication control unit.

FIG. 49 shows a schematic view of the optimization of communication route involving communication relay units numbered 1 through z. In one approach, parameters related to each of the $0.5(z+1)(z+2)$ pairs of possible communication links (e.g. distance, power output, range, system use, and others), may be individually evaluated, or may be mathematically transformed and further evaluated. More complex mathematical transformations involving (a) multiple properties, and (b) multiple pairs of units (or all units) are possible.

There has thus been shown and described novel apparatus and methodology for controlling an implantable medical device which fulfills all the objects and advantages sought therefor. Many changes, modifications, variations and other uses and applications of the subject invention will, however, become apparent to those skilled in the art after considering this specification and the accompanying drawings which disclose the preferred embodiments thereof. All such changes, modifications, variations and other uses and applications which do not depart from the spirit and scope of the invention are deemed to be covered by the invention, which is to be limited only by the claims which follow.

What is claimed is:

1. A medical treatment system having an implantable medical device, which system provides location information pertaining to a person in whom the device is implanted, to facilitate communication between the device and a remote location, said system comprising:
   (1) electronic medical apparatus adapted to be implanted in a human, a so-called implantable medical device ("IMD"), comprising, in combination:
      (a) a first transmitting/receiving ("T/R") device for at least one of
         (i) transmitting information to, and
         (ii) receiving at least one control signal from, at least one remote location;
      (b) a medical treatment device, coupled to said first T/R device, for treating said patient;
   (2) a first locator device, adapted to be located in the close vicinity of said human in whom said device is implanted, comprising a wireless first locator transmitting device, operative to transmit first locator signals;
   (3) a plurality of second locator devices, each comprising:
      (a) a second locator receiving device, operative to receive said first locator signals;
      (b) a communication quality assessment device, coupled to said second locator receiving device, for assessing the quality of the received first locator signals, and for producing a communication quality signal in dependence upon the assessed quality of said first locator signals; and
      (c) a second locator transmitting device, coupled to said communication quality assessment device, for transmitting said communication quality signal;
   (4) a communication device, comprising
      (a) a second T/R device, for:
         (i) receiving said communication quality signals from each of the second locator transmitting devices, and
         (ii) transmitting a low communication quality signal;
      (b) a second T/R controlling device, coupled to said second T/R device, for (i) indicating a state in which the quality represented by each of said communication quality signals is less than an acceptable value, wherein said acceptable value corresponds to a minimum acceptable communication quality, and (ii) in response to said indication, causing said second T/R device to transmit a low communication quality signal;

wherein:
(a) each of said communication quality assessment devices determines information concerning the location of said first locator device based on at least one of:
  (i) the detection of said first locator signals by said second locator device,
  (ii) the absence of a detected first locator signal by said second locator device, and
  (iii) the quality of said detected first locator signals;
(b) each of said second locator devices is operative to transmit said information concerning the location of said first locator device to said communication device; and
(c) said second T/R controlling device is operative to provide said low communication quality signal indicating that none of the second locator devices is receiving a first locator signal with quality greater than or equal to said acceptable value;
whereby (1) said first locator device provides information about the location of said IMD, without electrical interaction with the IMD; and (2) said system indicates when said human in whom said IMD is implanted is out of communications range of said second T/R device.

2. The medical treatment system defined in claim 1, wherein said first locator device and said IMD are mechanically linked, such that both are adapted to be implanted in said human in whom both said devices continue to be mechanically linked.

3. The medical treatment system defined in claim 1, wherein said IMD and said first locator device are adapted to be implanted in said human, but are not mechanically linked.

4. The medical treatment system defined in claim 3, wherein said first locator device is adapted to be implanted subcutaneously in said human and said IMD is adapted to be implanted at a deeper level than the subcutaneous layer.

5. The medical treatment system defined in claim 1, wherein said IMD is adapted to be implanted in said human and said first locator device is adapted to be located outside of said human, touching the outer surface of the skin of said human.

6. The medical treatment system defined in claim 1, wherein said IMD is adapted to be implanted in said human and said first locator device is adapted to be located outside of said human, and is physically linked to an article worn by said human.

7. The medical treatment system defined in claim 6, wherein said article of clothing includes at least one of: a belt, a watch and jewelry.

8. The medical treatment system defined in claim 1, further comprising
(5) alarm apparatus, situated in proximity to at least one of (i) said person, and (ii) another person, comprising:
(a) a notification device for producing at least one output from the group consisting of a sound, a light and a vibration; and
(b) a receiving device, coupled to said notification device, for receiving said low communication quality signal;
wherein
  said receiving device causes said notification device to produce said at least one output upon receipt of a low communication quality signal indicating an unacceptable quality communication between said first and said second locator device;
thereby to notify at least one of (i) said person and) said other person that the location of said first locator device requires attention.

9. The medical treatment system defined in claim 1, wherein at least one of said second locator devices further comprises a notification device, coupled to a respective one of said communication quality assessment devices, for producing at least one output from the group consisting of: sound, a light and a vibration; and
wherein at least one of:
(i) the absence of a received first locator signal;
(ii) the receipt of an unacceptable quality first locator signal;
causes the production of said at least one output by said notification device;
thereby to notify at least one person that the location of said first locator device requires attention.

10. The medical treatment system defined in claim 1, wherein the IMD includes at least one sensor, coupled to said first T/R device for sensing a medical condition of said person and producing a sensor output signal in response to said medical condition, wherein said fir T/R device transmits a representation of said sensor output signal.

11. The medical treatment system defined in claim 10, wherein said sensor is further coupled to said medical treatment device and wherein said medical treatment device automatically applies an appropriate treatment to said patient in response thereto.

12. The medical treatment system defined in claim 1, wherein:
(a) at least one of said second locator transmitting devices is further operative to transmit a first assessment signal,
(b) said first locator device further comprises a first locator receiving device, coupled to said first locator transmitting device, for receiving said first assessment signal, and
(c) said first locator transmitting device is further operative to transmit a second assessment signal in response to receipt of said first assessment signal;
(d) said communication quality assessment device is operative to determine at least one of the receipt and the quality of the received second assessment signal, and to produce said communication quality signal in dependence upon the assessed quality of said second assessment signal;
wherein
  (i) said second or device transmits said first assessment signal to said first locator device;
  (ii) upon receipt of said first assessment signal, said first locator device transmits a second assessment signal to said second locator device; and
  (iii) said communication quality assessment device assesses said second assessment signal;
  thereby to assess the quality of communication between the two locator devices.

13. The medical treatment system defined in claim 1, wherein:
(a) said first T/R device is further operative to communicate with said second T/R device; and
(b) said communications device is adapted to be located in the close vicinity of at least one of said plurality of second locator devices;
whereby said communication quality signal, representing the quality of the first locator signal received by said second locator device, provides information concerning the expected quality of communication between said first T/R device and said second T/R device, without directly utilizing said first T/R device to provide said quality information.

14. The medical treatment system defined in claim 13, wherein, based on the quality of each respective communication quality signal, said second T/R controlling device is operative to control a feature of communication with said first T/R device selected from the group consisting of:
(i) a power output for said second T/R device;
(ii) a signal sensitivity for said second T/R device;
(iii) at least one transmission frequency for said second T/R device;
(iv) an output signal modulation type for said second T/R device;
(v) a selection of a connection mode from the group consisting of (a) a radiofrequency link, (b) the Internet, (c) a hard wire connection, for said second T/R device;
(vi) a rate of information transfer by said second T/R device
(vii) a method of signal encoding by said second T/R device;
(viii) a message repetition frequency, for said second T/R device; and
(ix) a selection of at least one other communication device with which said second T/R device communicates.

15. The medical treatment system defined in claim 13, wherein said communication device is located at said remote location and further comprises:
(c) a first input device, coupled to said second T/R device, responsive to a technical expert, for producing at least one real time remote control signal for controlling said IMD;
and wherein (i) said communication device is further operative to transmit said control signal to said IMD in response to a command inputted by said technical expert, said first T/R device is operative to receive said control signal, and (iii) said medical treatment device is responsive to said control signal for applying a treatment represented by said signal.

16. The medical treatment system defined in claim 13, further comprising a remote station (RS) at said
(a) a first input device, responsive to a medical expert, for producing at least one real time remote control signal for controlling said IMD, wherein said first T/R device is operative to receive said control signal, and said medical treatment device is responsive to said control signal for applying a treatment represented by said signal; and
(b) a third transmitting/receiving (T/R) device, coupled to said input device, for electronic communication with a T/R device selected from the group consisting of (i) the first T/R device of said remotely located IMD, and (ii) the second T/R device of said communication device, wherein said second T/R device is operative receive said control signal and re-transmit it to said first T/R device.

17. The medical treatment system defined in claim 16, wherein:
(a) said third T/R device is operative to receive said low communication quality signal from said second T/R device; and
(b) said remote station further comprises a third T/R controlling device, coupled to said third T/R device, for controlling a feature of communication between said third T/R device and said first T/R device;
thereby to permit said third T/R device to improve its communications with said first T/R device.

18. The medical treatment system defined in claim 16, wherein said third T/R device is operative to notify at least one of:
(a) said person;
(b) another person in the vicinity of said person;
of a received communication quality signal indication an unacceptable quality communication between said first, and said second locator device.

19. The medical treatment system defined in claim 18 further comprising:
alarm apparatus, situated in proximity to at least one of (i) said person, and (ii) another person, comprising:
(a) a notification device for producing at least one of a sound, a light and a vibration; and
(b) a receiving device, coupled to said notification device; wherein
said medical expert inputs an alarm signal to said first input device, for transmission by said third T/R device to said alarm apparatus;
thereby to notify at least one of (i) said person, and (ii) another person, of said unacceptable quality communication.

20. The medical treatment system defined in claim 13, wherein:
(a) said first T/R device is operative to receive said low communication quality signal from said second T/R device; and
(b) said IMD further comprises a first T/R controlling device, coupled to said first T/R device, for controlling a feature of communication between said first T/R device and said second T/R device;
thereby to cause said first T/R device to improve its communications with said second T/R device.

21. The medical treatment system defined in claim 1, further comprising:
(1) at least one supplemental plurality of second locator devices, each comprising:
(a) a supplemental second locator receiving device, operative to receive said first locator signals;
(b) a supplemental communication quality assessment device, coupled to said supplemental second locator receiving device, for assessing the quality of the received first locator signals, and for producing a supplemental communication quality signal in dependence upon the assessed quality of said first locator signals; and
(c) a supplemental second locator transmitting device, coupled to said supplemental communication quality assessment device, for transmitting said supplemental communication quality signal;
(2) at least one supplemental communication device for assessing the quality of signals received by one respective supplemental plurality of second locator devices, each of said supplemental communication devices comprising
(a) a supplemental second T/R device, for:
(i) for receiving said communication quality signals from each of the supplemental second locator transmitting devices among the respective plurality, and
(ii) for transmitting a supplemental low quality signal;
(b) a supplemental second T/R controlling device, coupled to said supplemental second T/R device, for (i) indicating a state in which the quality represented by each of said communication quality signals is less than a supplemental acceptable value, wherein said supplemental acceptable value corresponds to a supplemental minimum acceptable communication quality, and in response to said indication, causing said supplemental second T/R device to transmit a supplemental low communication quality signal;
(3) an additional communications device, comprising an additional T/R device coupled to an additional T/R controlling device, for;
receiving said low communication quality signal;
receiving said at least one supplemental low communication quality signals; and
producing a global alarm signal upon receipt of low communication quality signals from each of (i) said communication device and (ii) each of said at least one supplemental communication devices.

22. The medical treatment system defined in claim 21, wherein:
(a) said first T/R device is further operative to communicate with each of said supplemental second T/R devices; and
(b) each of said supplemental communications devices is adapted to be located in the close vicinity of at least one of said plurality of respective supplemental second locator devices;
whereby each of said supplemental communication quality signals, representing the quality of the first locator signal received by said respective second locator device, provides information concerning the expected quality of communication between said first T/R device and said respective supplemental second T/R device, without directly utilizing said first T/R device to provide said quality information.

23. The medical treatment system defined in claim 22, wherein
(A) each of at least two of said T/R controlling devices is further operative to cause said respective second T/R device to transmit a numerical value representing the quality of said respective received communication quality signals and supplemental communication quality signals; and
(B) said additional communications device is operative to receive signals representing said numerical values and
(C) said additional T/R controlling device is operative to determine which one of the plurality of communication devices is associated with the greatest numerical value, and to cause said additional T/R device to transmit an optimization signal representing the identity of an optimum communications device representing said one communications device associated with said greatest value;
whereby said system is operative to determine
(A) the identity of one specific communications device among (i) said communications device and (ii) said at least one supplemental communications device with the highest quality first locator signal; and
(B) the identity of one optimum second T/R device, associated with said one specific communications device;
thereby to determine, for said human situated at a given location, the optimum choice of second T/R device for communicating with said first T/R device.

24. The medical treatment system defined in claim 23, wherein at least one of said second T/R device and said supplemental T/R devices indicated by said optimization signal is operative to receive said optimization signal, and said respective second T/R controlling device is further operative to cause said selected second T/R device to communicate with said first T/R device.

25. The medical treatment system defined in claim 23, wherein at least one of said second T/R devices is operative to receive said optimization signal and to cause said respective second T/R controlling device to control a feature of communication with said first T/R device, selected from the group consisting of:
(i) a power output for said second T/R device;
(ii) a signal sensitivity for said second T/R device;
(iii) at least one transmission frequency for said second device;
(iv) an output signal modulation type said second T device;
(v) a selection of a connection mode from the group consisting of (a) a radiofrequency link, (b) the Internet, (c) a hard wire connection, for said second T/R device;
(vi) a rate of information transfer by said second T/R device
(vii) a method of signal encoding by said second T/R device:
(viii) a message repetition frequency, for said second T/R device; and
(ix) a selection of at least one other communication device with which said second T/R device communicates.

26. The medical treatment system defined in claim 23, wherein:
(a) said first T/R device is operative to receive said optimization signal from said additional T/R device;
(b) said IMD further comprises a first T/R controlling device, coupled to said first T/R device, for controlling the features of communication between said first T/R device and said second T/R device; and
(c) based on said received optimization signal, said first T/R controlling device is operative to cause said first T/R device to communicate with a particular second T/R device;
thereby to cause said first T/R device to optimize communications with the plurality of second T/R devices, based on the locations of each of the human and of the second T/R devices.

27. A medical treatment system having an implantable medical device, which system provides location information pertaining to a person in whom the device is implanted, to facilitate communication between the device and a remote location, said system comprising:
(1) electronic medical apparatus adapted to be implanted in a human, a so-called implantable medical device ("IMD"), comprising, in combination:
(a) a first transmitting/receiving ("T/R") device for at least one of
(i) transmitting information to, and
(ii) receiving at least one control signal from, at least one remote location;
(b) a medical treatment device, coupled to said first T/R device, for treating said patient;
(2) a first locator device, adapted to be located in the close vicinity of said human, comprising:
(a) a first locator receiving device, operative to receive second locator signals;
(b) an energy storage device, coupled to said first locator receiving device, for storing energy;
(c) a first locator transmitting device, coupled to said energy storage device, operative to transmit first locator signals;
(3) a plurality of second locator devices, each comprising:
(a) a second locator transmitting device, operative to transmit second locator signals, for receipt by said first locator receiving device;
(b) a second locator receiving device, operative to receive said first locator signals;

(c) a communication quality assessment device, coupled to said second locator receiving device, for assessing the quality of said received first locator signals, and for producing a communication quality signal in dependence upon the assessed quality of said first locator signals; and (d) a second locator quality signal transmitting device, coupled to said communication quality assessment device, for transmitting said communication quality signal;

(4) a communication device, comprising (a) a second T/R device, for:
(i) receiving said communication quality signals from each of the second locator transmitting devices and
(ii) transmitting a low communication quality signal;

(b) a second T/R controlling device, coupled to said second T/R device, for (i) indicating a state in which the quality represented by each of said communication quality signals is less than an acceptable value, wherein said acceptable value corresponds to a minimum acceptable communication quality, and (ii) in response to said indication, causing said second T/R device to transmit a low communication quality signal;

wherein:

(a) each of said communication quality assessment devices determines information concerning the location of said first locator device based on at least one of:
(i) the detection of said first locator signals by said second locator device,
(ii) the absence of a detected first locator signal by said second locator device, and
(iii) the quality of said detected first locator signals;

(b) each of said second locator devices is operative to transmit said information concerning the location of said first locator to said communication device; and (c) said second T/R controlling device is operative to provide said low communication quality signal indicating that none of the second locator devices is receiving a first locator signal with quality greater than or equal to said acceptable value;

whereby (1) said first locator device provides information about the location of said IMD, without electrical interaction with the IMD; and (2) said system indicates when said human in whom said IMD is implanted is out of communications range of said second T/R device.

28. The medical treatment system defined in claim 27, wherein said first locator device and said IMD are mechanically linked, such that both are adapted to be implanted in said human in whom both said devices continue to be mechanically linked.

29. The medical treatment system defined in claim 27, wherein said IMD and said first locator device are adapted to be implanted in said human, but are not mechanically linked.

30. The medical treatment system defined in claim 29, wherein said first locator device is adapted to be implanted subcutaneously in said human and said IMD is adapted to be implanted at a deeper level than the subcutaneous layer.

31. The medical treatment system defined in claim 27, wherein said IMD is adapted to be implanted in said human and said first locator device is adapted to be located outside of said human, touching the outer surface of the skin of said human.

32. The medical treatment system defined in claim 27, wherein said IMD is adapted to be implanted in said human and said first locator device is adapted to be located outside of said human, and is physically linked to an article worn by said human.

33. The medical treatment system defined in claim 32, wherein said article of clothing includes at least one of: a belt, a watch and jewelry.

34. The medical treatment system defined in claim 27, further comprising:

(5) alarm apparatus, situated in proximity to at least one of (i) said person, and another person, comprising:
(a) a notification device for producing at least one output from the group consisting of a sound, a light and a vibration; and
(b) a receiving device, coupled to said notification device, for receiving said low communication quality signal;

wherein
said receiving device causes said notification device to produce said at least one output upon receipt of a communication quality signal indicating an unacceptable quality communication between said first and said second locator device;

thereby to notify at least one of (i) said person and said other person that the location of said first locator device requires attention.

35. The medical treatment system defined in claim 27, wherein at least one of said second locator devices further comprises a notification device, coupled to a respective one of said communication quality assessment devices, for producing at least one output from the group consisting of: a sound, a light, and a vibration; and wherein at least one of:
(i) the absence of a received first locator signal;
(ii) the receipt of an unacceptable quality first locator signal;
causes the production of said at least one output by said notification device;
thereby to notify at least one person that the location of said first locator device requires attention.

36. The medical treatment system defined in claim 27, wherein the IMD includes at least one sensor, coupled to said first T/R device for sensing a medical condition of said person and producing a sensor output signal in response to said medical condition, wherein said first T/R device transmits a representation of said sensor output signal.

37. The medical treatment system defined in claim 36, wherein said sensor is further coupled to said medical treatment device and wherein said medical treatment device automatically applies an appropriate treatment to said patient in response thereto.

38. The medical treatment system defined in claim 27, wherein:

(a) said first locator device further comprises a first locator communication quality assessment device, coupled to said first locator receiving device and to said first locator transmitting device, for assessing the quality of the received second locator signals and for producing first locator communication quality signals in dependence upon the assessed quality of said second locator signals;

(b) said first locator transmitting device is operative to transmit said first locator transmitting device is operative to said second locator devices;

(c) each of said second locator devices further comprise a second locator transmitting device controller, coupled to said respective second, locator receiving device, for receipt of said first locator communication quality signals, and coupled to at least one of:

(I) said respective second locator transmitting device, for controlling at least one of:
  (i) the power output of said respective second locator transmitting device;
  (ii) the transmitter frequency of said respective second locator transmitting device;
  (iii) the repetition rate of said respective second locator transmitting device; and
  (iv) the direction of transmission of said respective second locator transmitting device; and
(II) said respective second locator quality signal transmitting device, to control a feature of communication selected from the group consisting of:
  (i) a power output for said respective second locator quality signal transmitting device;
  (ii) at least one transmission frequency for said respective second locator quality signal transmitting device;
  (iii) an output signal modulation type for said respective second locator quality signal transmitting device;
  (iv) a selection of a connection mode from the group consisting of (a) a radiofrequency link, (b) the Internet, (c) a hard wire connection, for said respective second locator quality signal transmitting device;
  (v) a rate of information transfer by said respective second locator quality signal transmitting device;
  (vi) a method of signal encoding by said respective second locator quality signal transmitting device;
  (vii) a message repetition frequency, for said respective second locator quality signal transmitting device; and
  (viii) a selection of at least one other communication device with which said respective second locator quality signal transmitting device communicates;
thereby to improve communication between (i) said second locator devices and (ii) at least one of said first locator device and another device.

39. The medical treatment system defined in claim 27, wherein:
(a) said first locator device further comprises a first locator communication quality assessment device coupled to said first locator receiving device and to said first locator transmitting device for assessing the quality of the received second locator signals, and for producing first locator communication quality signals, in dependence upon the assessed quality of said second locator signals;
(b) said first locator transmitting device is operative to transmit said first locator communication quality signals to said second locator device;
(c) said second locator receiving device is further coupled to said second locator quality signal transmitting device, to re-transmit said first locator communication quality signals;
(d) said second T/R devices is operative to receive said re-transmitted first locator communication quality signals; and
(e) said second T/R controlling device is operative to control a mode of communication between said second T/R device and said first R device, in dependence upon said first locator communication quality signals;
thereby to improve communication to said IMD.

40. The medical treatment system defined in claim 39, wherein:
(a) said second T/R device is operative to re-transmit said received first locator communication quality signals;
(b) said first T/R device is operative to receive said re-transmitted first locator communication quality signals;
(c) said IMD further comprises a first T/R controlling device, coupled to said first T/R device, for controlling the mode of communication between said first T/R device and said second T/R device;
thereby to cause said first T/R device to improve communication with said second T/R device.

41. The medical treatment system defined in claim 39, further comprising a remote station (RS) at said remote location comprising:
(a) a first input device, responsive to a technical expert, for producing at least one real time remote control signal for controlling said IMD;
(b) a third transmitting/receiving (T/R) device, coupled to said input, device, for electronic, communication with at least one of (i) the first T/R device of said remotely located IMD, and (ii) the second T/R device of said communication device;
(c) a third T/R controlling device, coupled to said third T/R device, for controlling a feature of communication between said third T/R device and at least one of said first T/R device and said second T/R device; and
(d) said second T/R device is operative to re-transmit said received first locator communication quality signals;
wherein:
  (i) said third T/R device receives said re-transmitted first locator communication quality signals; and
  (ii) said third T/R controlling device controls a feature of communication of said third T/R device based on said first locator communication quality signals;
thereby to cause said third T/R device to improve its communications.

42. The system defined in claim 27, wherein said energy storage device is adapted to store energy contained in said incoming electrical signals, and wherein said transmitted second locator signals, received by said first locator receiver, supply energy for powering said first locator device.

43. The medical treatment system defined in claim 27, wherein:
(a) said first T/R device is further operative to communicate with said second T/R device; and
(b) said communications device is adapted to be located in the close vicinity of at least one of said plurality of second locator devices;
whereby said communication quality signal, representing the quality of the first locator signal received by said second locator device, provides information concerning the expected quality of communication between said first T/R device and said second T/R device, without directly utilizing said first T/R device to provide said quality information.

44. The medical treatment system defined in claim 43, wherein said communication device is located at said remote location and further comprise:
(c) a first input device, coupled to said second T/R device, responsive to a technical expert, for producing at least one real time remote control signal for controlling said IMD;
and wherein (i) said communication device is further operative to transmit said control signal to said IMD in response to a command inputted by said technical expert, (ii) said first T/R device is operative to receive said control signal, and (iii) said medical treatment device is responsive to said control signal for applying a treatment represented by said signal.

45. The medical treatment system defined in claim 43, wherein, based on the quality of each respective communication quality signal, said second T/R controlling device is operative to control a feature of communication with said first T/R device selected from the group consisting of:
   (i) a power output for said second T/R device;
   (ii) a signal sensitivity for said second device;
   (iii) at least one transmission frequency for said second T/R device;
   (iv) an output signal modulation type for said second T/R device;
   (v) a selection of a connection mode from the group consisting of (a) a radiofrequency link, (b) the Internet, (c) a hard wire connection, for said second T/R device;
   (vi) a rate of information transfer by said second T/R device
   (vii) a method of signal encoding by said second T/R device;
   (viii) a message repetition frequency, for said second T/R device; and
   (ix) a selection of at least one other communication device with which said second T/R device communicates.

46. The medical treatment system defined in claim 43, further comprising a remote station (RS) at said remote location including:
   (a) a first input device, responsive to a medical expert, for producing at least one real time remote control signal for controlling said IMD, wherein said first T/R device is operative to receive said control signal, and said medical treatment device is responsive to said control signal for applying a treatment represented by said signal; and
   (b) a third transmitting/receiving (T/R) device, coupled to said input device, for electronic communication with a T/R device selected from the group consisting of (i) the first T/R device of said remotely located IMD, and (ii) the second T/R device of said communication device, wherein said second T/R device is operative receive said control signal and re-transmit it to said first T/R device.

47. The medical treatment system defined in claim 46, wherein: (a) said third T/R device is operative receive said low communication quality signal from said second T/R device; and
   (b) said remote station further comprises a third T/R controlling device, coupled to said third T/R device, for controlling a feature of communication between said third T/R device and said first T/R device;
   thereby to permit said third T/R device to improve its communications with said first T/R device.

48. The medical treatment system defined in claim 46, wherein said third T/R device is operative to notify at least one of:
   (a) said person;
   (b) another person in the vicinity of said person;
   of a received communication quality signal indicating an unacceptable quality communication between said first and said second locator device.

49. The medical treatment system defined in claim 48 further comprising:
   alarm apparatus, situated in proximity to at least one of (i) said person, and (ii) another person, comprising:
   (a) a notification device for producing at least one of a sound, a light and a vibration; and
   (b) a receiving device, coupled to said notification device; wherein
   said medical expert inputs an alarm signal to said first input device, for transmission by said third T/R device to said alarm apparatus;
   thereby to notify at least one of (i) said person, and (ii) another person, of said unacceptable quality communication.

50. The medical treatment system defined in claim 43, wherein:
   (a) said first T/R device is operative to receive said low communication quality signal from said second T/R device; and
   (b) said IMD further comprises a first T/R controlling device, coupled to said first T/R device, for controlling a feature of communication between said first T/R device and said second T/R device;
   thereby to permit said first T/R device to improve its communications with said second T/R device.

51. The medical treatment system defined in claim 27, further comprising:
   (1) at least one supplemental plurality of second locator devices, each comprising:
      (a) a supplemental second locator transmitting device, operative to transmit second locator signals, for receipt by said first locator receiving device;
      (b) a supplemental second locator receiving device, operative to receive said first locator signals;
      (c) a supplemental communication quality assessment device, coupled to said supplemental second locator receiving device, for assessing the Quality of the received first locator signals, and for producing a supplemental communication quality signal in dependence upon the assessed quality of said first locator signals; and
      (d) a supplemental second locator quality signal transmitting device, coupled to said supplemental communication quality assessment device, for transmitting said supplemental communication quality signal;
   (2) at least one supplemental communication device for assessing the quality of signals received by one respective supplemental plurality of second locator devices, each of said supplemental communication devices comprising
      (a) a supplemental second T/R device, for:
         (i) for receiving said communication quality signals from each of the supplemental second locator quality signal transmitting devices among the respective plurality, and
         (ii) for transmitting a supplemental low quality signal;
      (b) a supplemental second T/R controlling device, coupled to said supplemental second T/R device, for (i) indicating a state in which the quality represented by each of said communication quality signals is less than a supplemental acceptable value, wherein said supplemental acceptable value corresponds to a supplemental minimum acceptable communication quality, and (ii) in response to said indication, causing said supplemental second T/R device to transmit a supplemental low communication quality signal;
   (3) an additional communications device, comprising an Additional T/R device coupled to an additional T/R controlling device, for;
      receiving said low communication quality signal;
      receiving said at least one supplemental low communication quality signals; and producing a global alarm signal upon receipt of low communication quality signals from each of (i) said communication device and (ii) each of said at least one supplemental communication devices.

52. The medical treatment system defined in claim 51, wherein:
  (a) said first T/R device is further operative to communicate with each of said supplemental second T/R devices; and
  (b) each of said supplemental communications devices is adapted to be located in the close vicinity of at least one of said plurality of respective supplemental second locator devices;
  whereby each of said supplemental communication quality signals, representing the quality of the first locator signal received by said respective second locator device, provides information concerning the expected quality of communication between said first T/R device and said respective supplemental second T/R device, without directly utilizing said first T/R device to provide said quality information.

53. The medical treatment system defined in claim 52, wherein
  (A) each of at least two of said T/R controlling devices is further operative to cause said respective second T/R device to transmit a numerical value representing the quality of said respective received communication quality signals and supplemental communication quality signals; and
  (B) said additional communications device is operative to receive signals representing said numerical values and
  (C) said additional T/R controlling device is operative to determine which one of the plurality of communication devices is associated with the greatest numerical value, and to cause said additional T/R device to transmit an optimization signal representing the identity of an optimum communications device representing said one communications device associated with said greatest value;
whereby said system is operative to determine
  (A) the identity of one specific communications device among (i) said communications device and (ii) said at least one supplemental communications device with the highest quality first locator signal; and
  (B) the identity of one optimum second T/R device, associated with said one specific communications device;
thereby to determine, for said human situated at a given location, the optimum choice of second T/R device for communicating with said first T/R device.

54. The medical treatment system defined in claim 53, wherein at least one of said second T/R device and said supplemental T/R devices indicated by said optimization signal is operative to receive said optimization signal, and said respective second T/R controlling device is further operative to cause said selected second T/R device to communicate with said first T/R device.

55. The medical treatment system defined in claim 53, wherein at least one of said second T/R devices is operative to receive said optimization signal and to cause said respective second T/R controlling device to control a feature of communication with said first T/R device, selected from the group consisting of:
  (i) a power output for said second T/R device;
  (ii) a signal sensitivity for said second T/R device;
  (iii) at least one transmission frequency for said second T/R device;
  (iv) an output signal modulation type for said second T/R device;
  (v) a selection of a connection mode from the group consisting of (a) a radiofrequency link, (b) the Internet, (c) a hard wire connection, for said second T/R device;
  (vi) a rate of information transfer by said second T/R device
  (vii) a method of signal encoding by said second T/R device;
  (viii) a message repetition frequency, for said second T/R device; and
  (ix) a selection of at least one other communication device with which said second T/R device communicates.

56. The medical treatment system defined in claim 53, wherein:
  (a) said first T/R device is operative to receive said optimization signal from said additional T/R device;
  (b) said IMD further comprises a first T/R controlling device, coupled to said first T/R device, for controlling the features of communication between said first T/R device and said second T/R device; and
  (c) based on said received optimization signal, said first T/R controlling device is operative to cause said first T/R device to communicate with a particular second T/R device;
thereby to cause said first T/R device to optimize communications with the plurality of second T/R devices, based on the locations of each of the human and of the second T/R devices.

* * * * *